(12) United States Patent
Notari et al.

(10) Patent No.: US 10,807,939 B2
(45) Date of Patent: Oct. 20, 2020

(54) METAL COMPOUNDS OF CALIXARENES, DETERGENT COMPOSITIONS CONTAINING THEM AND USE THEREOF IN LUBRICANT COMPOSITIONS

(71) Applicant: Eni S.p.A., Rome (IT)

(72) Inventors: Marcello Notari, San Donato Milanese (IT); Alberto Roselli, Paullo (IT); Alessandro Casnati, Parma (IT); Francesco Sansone, Parma (IT); Alessandro Burlini, Calvisano (IT)

(73) Assignee: Eni S.P.A., Rome (IT)

( * ) Notice: Subject to any disclaimer, the term of this patent is extended or adjusted under 35 U.S.C. 154(b) by 69 days.

(21) Appl. No.: 15/751,506

(22) PCT Filed: Aug. 10, 2016

(86) PCT No.: PCT/IB2016/054803
§ 371 (c)(1),
(2) Date: Feb. 9, 2018

(87) PCT Pub. No.: WO2017/025900
PCT Pub. Date: Feb. 16, 2017

(65) Prior Publication Data
US 2018/0237375 A1    Aug. 23, 2018

(30) Foreign Application Priority Data
Aug. 10, 2015  (IT) ................ 102015000043668

(51) Int. Cl.
*C07C 65/01*   (2006.01)
*C11D 3/16*   (2006.01)
(Continued)

(52) U.S. Cl.
CPC ......... *C07C 65/01* (2013.01); *C10M 107/28* (2013.01); *C10M 159/22* (2013.01); *C10M 175/0033* (2013.01); *C10M 177/00* (2013.01); *C11C 3/04* (2013.01); *C11D 3/168* (2013.01); *C11D 3/187* (2013.01); *C11D 3/2065* (2013.01);
(Continued)

(58) Field of Classification Search
CPC ...... C10M 159/22; C07C 65/01; C11D 3/187; C11D 3/2082; C10N 2030/04
See application file for complete search history.

(56) References Cited

U.S. PATENT DOCUMENTS 5,114,601 A * 5/1992 Cook .................. C07C 59/235
508/398
5,205,946 A * 4/1993 Cook .................. C07C 59/235
508/460

(Continued)

FOREIGN PATENT DOCUMENTS

EP        A-0450874    *  9/1991
EP        0450874 A2     10/1991
(Continued)

OTHER PUBLICATIONS

International Search Report & Written Opinion for PCT/IB2016/054803 dated Nov. 11, 2016, 10 pages.
(Continued)

*Primary Examiner* — Ellen M McAvoy
(74) *Attorney, Agent, or Firm* — Praedcere Law

(57) ABSTRACT

The present invention relates to a metal compound of calixarene not containing sulfur and dispersible in oil, which can be partially salified, or neutral, or basic or overbased, said calixarene having general formula (I) in which: a) $R_1$, $R_2$, $R_3$ and $R_4$ are independently selected from hydrogen, or a group containing carbon and hydrogen, or a group containing in addition to carbon and hydrogen also heteroatoms, provided that said heteroatoms are not sulfur; b) one of the two substituents $R_5$ and $R_6$ is hydrogen, while the other may be selected from hydrogen, or a linear or branched alkyl with a number of carbon atoms between 1 and 6, preferably methyl, ethyl, 1-propyl, 2-propyl, n-butyl, sec-butyl, more preferably methyl or ethyl; c) n is the number of units of the calixarene ring and is comprised in the range between 4 and 16, preferably between 5 and 12; said calixarene being characterized in that in at least one of the n units of the calixarene ring, at least one of the substituents $R_1$, $R_2$, $R_3$ and $R_4$ contains at least one acid group of carboxylic type available for the reaction with a metal base, with the proviso that said acid group of carboxylic type is not contained in a unit of the calixarene ring derived from salicylic acid.

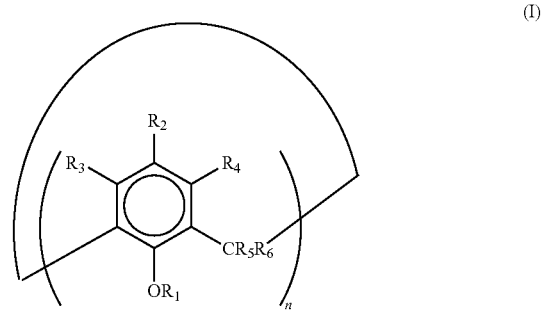

(I)

34 Claims, No Drawings

(51) Int. Cl.
 *C11D 3/18* (2006.01)
 *C10M 107/28* (2006.01)
 *C11C 3/04* (2006.01)
 *C11D 3/20* (2006.01)
 *C10M 159/22* (2006.01)
 *C10M 175/00* (2006.01)
 *C10M 177/00* (2006.01)
 *C10N 30/04* (2006.01)

(52) U.S. Cl.
 CPC .......... *C11D 3/2068* (2013.01); *C11D 3/2082* (2013.01); *C10M 2207/262* (2013.01); *C10N 2030/04* (2013.01)

(56) References Cited

U.S. PATENT DOCUMENTS

| | | | | |
|---|---|---|---|---|
| 5,602,084 | A | * | 2/1997 | Moreton ............ C10M 159/20 508/391 |
| 5,780,403 | A | * | 7/1998 | Moreton ............ C07C 43/21 508/580 |
| 5,840,814 | A | | 11/1998 | Majoros et al. |
| 6,174,844 | B1 | * | 1/2001 | Moreton ............ C07G 17/008 508/585 |
| 6,200,936 | B1 | * | 3/2001 | Moreton ............ C07C 65/17 508/479 |
| 6,268,320 | B1 | * | 7/2001 | Crawford ............ C10M 159/22 508/572 |
| 6,399,549 | B1 | * | 6/2002 | Taylor ............ B01D 17/045 508/479 |
| 6,596,038 | B1 | * | 7/2003 | Moreton ............ C07C 65/105 44/386 |
| 2004/0186027 | A1 | * | 9/2004 | Moreton ............ C07C 65/105 508/186 |

FOREIGN PATENT DOCUMENTS

| | | |
|---|---|---|
| EP | 0685553 A2 | 12/1995 |
| EP | 0755998 A1 | 1/1997 |
| EP | 0954517 B1 | 3/2003 |
| WO | WO20150159249 A1 | 10/2015 |

OTHER PUBLICATIONS

Cunningham, et al., "Colloids and Surfaces A: Physicochem. Eng. Aspects 229 (2003) pp. 137-147".
Gutsche, et al. Org. Synth. 1990, vol. 68, pp. 234-246.
Bew et al. Chem. Commun. 2007, pp. 975-977.
Bew et al. J. Org. Chem. 2011, vol. 76, pp. 7076-7083.
Gutsche et al, Org. Prep. Proced. Int. 1992, vol. 25, pp. 137-139.
Bocchi et al., Tetrahedron 1982, 38, 3, pp. 373-378.
Cornforth et al., J. Pharmacol. 1955, 10, p. 73.
Ungaro et al., J. Org. Chem. 1997, 62, pp. 6236-6239.
Gutsche et al., J. Org. Chem., 1985, 50, pp. 5802-5806.
American Petroleum Institute (API) publication "Engine Oil Licensing and Certification System" (API EOLCS, 1507—Industry Services Department, Fourteenth Edition, Dec. 1996, Addendum 1, Dec. 1998.

* cited by examiner

METAL COMPOUNDS OF CALIXARENES, DETERGENT COMPOSITIONS CONTAINING THEM AND USE THEREOF IN LUBRICANT COMPOSITIONS

The present invention relates to metal compounds of calixarenes that do not contain sulfur and are dispersible in oil, and that may be partially salified, neutral, basic and overbased.

Moreover, the present invention relates to detergent compositions comprising said metal compounds of calixarenes, and to the process for preparing them.

Moreover, the present invention relates to the use, in lubricant formulations, of said detergent compositions, as detergent additives, capable of consistently reducing the formation of deposits, and to the lubricant formulations themselves.

In the present patent application, all the operating conditions given in the text are to be understood as preferred conditions, even if not expressly so stated.

For the purposes of the present text the term "comprise" or "include" also comprises the term "consist of" or "consisting essentially of".

For the purposes of the present text the definitions of ranges always include the limits of the range, unless specified otherwise.

One of the most critical properties of engine lubricants is their capacity to maintain in suspension the products derived from thermal and oxidative degradation of the lubricant. Oxidation, which is the main cause of degradation of the lubricant, is the result of interaction of the components of the lubricant with oxygen and with the by-products of combustion of the fuel. The components of the lubricant, at the operating temperatures of the engine, are involved in a complex series of radical reactions that give rise to products that are highly polar and acidic. These oxidation products, being insoluble in the lubricant, tend to separate and be deposited on metallic surfaces, for example in the cylinder/piston zone, leading to phenomena of wear.

In order to reduce the consequences of the phenomena of thermal and oxidative degradation it is known to add detergent additives to lubricants.

These detergent additives have two functions:
to keep the polar oxidation products in suspension,
to neutralize the inorganic and organic acidity derived both from the blow-by gases from combustion of the fuel, and from decomposition of the lubricant,
thus controlling the phenomena of formation of deposits, wear and corrosion.

The first function is performed by the metal salts of organic acids contained in the detergents, mainly salts of alkaline-earth metals, such as calcium and magnesium, commonly called soaps.

The second function is performed by the reserve of basicity, mainly in the form of carbonate of an alkaline-earth metal, such as calcium and magnesium, contained in some types of so-called "overbased" detergents.

Detergents may contain metal salts characterized by a stoichiometric amount of metal relative to the acid moiety and in this case they are called "neutral"; or they may contain metal compounds, partially salified, characterized by an amount of metal less than the stoichiometric amount of acid; or they may contain "basic" or "overbased" metal salts, characterized by an amount of metal in excess, with a ratio between the metal equivalents and those relating to the acid moiety greater than unity.

In the present patent application, "basic metal salts" are defined as those salts that contain the excess of metal, relative to the acid moiety, in the form of hydroxide of the metal; while "overbased metal salts" are defined as those salts that contain the excess of metal mainly in the form of carbonate of the metal.

Detergents based on overbased metal salts are characterized by a ratio between the metal equivalents and those relating to the acid moiety generally greater than 2.5 and contain a high level of carbonate of the metal in colloidal form, able to neutralize the acidity that forms while the lubricant is in service.

The alkalinity of a detergent is determined by method ASTM D2896, which allows measurement of the value of TBN (Total Base Number) expressed in mg KOH/g.

For detergents containing metal salts of strong organic acids, such as alkylbenzene sulfonic acids, only the carbonates and/or hydroxides of the metals optionally present in colloidal form in the detergent contribute to the TBN value.

For detergents containing metal salts of weak organic acids, such as those containing functional groups of phenolic or carboxylic type, the metal salts of the organic acids as well as the carbonates and/or hydroxides of the metals, optionally present in colloidal form in the detergent, contribute to the TBN value.

The commonest detergents are those based on salts of alkaline-earth metals, neutral, or basic, or overbased, derived from organic acids containing sulfur atoms, for example the alkylbenzene sulfonates of calcium or magnesium, the alkylnaphthalene sulfonates of calcium or magnesium, the sulfurized alkylphenates of calcium or magnesium and the sulfurized alkylnaphthenates of calcium or magnesium.

One of the main problems relating to the use of these types of detergents in engine lubricants is the high sulfur content.

Sulfur is a source of air pollution, but also has an adverse effect on systems of after-treatment of exhaust gases, which were introduced on vehicles with the aim of reducing emissions of pollutants, allowing to satisfy the recent legislation in this area.

There is therefore a need for detergents based on metal salts of organic acids not containing sulfur.

In response to this need, patent EP 450874 describes a class of overbased calixarene metal salts not containing sulfur, having as substituents the hydroxyl group or groups able to react with a metal base.

In patent EP 450874, the overbased metal salts described are salts of alkaline-earth metals, such as calcium, magnesium and barium, of a calix[n]arene of formula (Z):

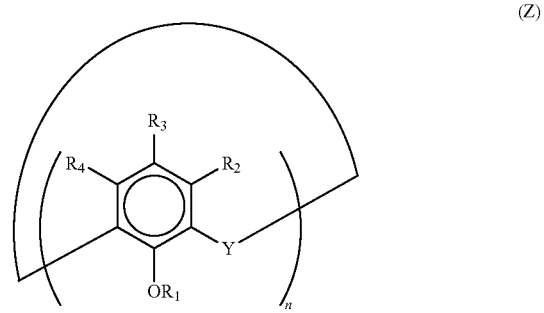

(Z)

in which Y is a divalent bridge group; $R^3$ is a group containing carbon and hydrogen or a group containing in addition to carbon and hydrogen also heteroatoms; n is an integer between 3 and 9, and alternatively either $R^1$ is hydroxyl and $R^2$ and $R^4$ are independently hydrogen, or a group containing carbon and hydrogen, or a group containing in addition to carbon and hydrogen also heteroatoms, or $R^2$ and $R^4$ are hydroxyl and $R^1$ is independently hydrogen, or a group containing carbon and hydrogen, or a group containing in addition to carbon and hydrogen also heteroatoms.

Furthermore, in patent EP 450874, a process is described for the production of these overbased metal salts, which comprises reaction of a metal base, preferably calcium hydroxide and/or calcium oxide, with a calixarene of formula (Z), or with a metal salt of the calixarene of formula (Z), in which the amount of metal is less than the stoichiometric amount of acid; or with the neutral or overbased metal salt of the calixarene of formula (Z).

The metal base may be supplied to the reaction mixture with a single addition or with multiple additions at various times during the reaction. After each addition of the metal base, carbon dioxide is added, which transforms the calcium hydroxide into calcium carbonate. The process is carried out in the presence of solvents.

As noted in the article "Colloids and Surfaces A: Physicochem. Eng. Aspects 229 (2003) 137-147, I.D. Cunningham et al.", the calixarenes, for example p-tert-butyl calix[8]arene, having unfunctionalized phenolic hydroxyls, as a result of reaction with calcium hydroxide are only partially neutralized (salified) to approx. 25%. This means that if only these calixarenes are used in the preparation of the overbased calcium salts, products would be obtained with a low content of salified phenolic units (low soap content) and hence with a low capacity for reducing the formation of deposits (low detergent capacity).

To overcome these drawbacks, as stated in patent EP 450874, preparation of the overbased salts of calixarenes is carried out using, together with the calixarenes, also alkyl carboxylic acids, such as stearic acid, which are fully salified in the reaction with calcium hydroxide.

Nevertheless, the products described in EP 450874 still do not have an optimum capacity for containing the formation of deposits. This characteristic was evaluated by the TEOST MHT method (ASTM D7097) and is highlighted in the comparative examples of the present patent application.

Moreover, the detergent products as described in EP 450874 do not have a high degree of incorporation of calcium carbonate and therefore have a not very high alkalinity value, determined by method ASTM D2897, as demonstrated in the comparative examples of the present patent application.

In response to the need for overbased salts of calixarenes with higher alkalinity value, patent EP 755998 describes calixarenes containing hydroxyl substituents of the phenolic type which, in contrast to those described in patent EP 450874, have a molecular weight of at least 1880 Da, obtained with longer-chain alkyl substituents.

However, these products also have a non-optimum detergent capacity, which does not depend on the molecular weight of the calixarenes, but on the type of functionalization.

The use of the calixarenes claimed in patents EP 450874 and EP 755998 makes it impossible, moreover, to prepare neutral and basic detergents with high soap content, types of detergents frequently used in the formulation of automotive lubricants.

Patent EP 954517 describes a class of calixarene compounds without sulfur, which contain in the calixarene ring at least one unit of salicylic acid, whose carboxyl group, having an acidity greater than that of phenol, is readily salifiable by a metal base. The metal salts of such compounds, whose methods of synthesis are similar to those given in the patents cited above, are used as detergents or dispersants mainly in lubricants for low-speed or medium-speed marine diesel engines.

The problem with the calixarenes described in EP 954517 is that the number of salicylic acid units contained in the calixarene ring must be low to guarantee that the overbased metal salts derived from such products are soluble in lubricating oil. In fact, in the case of a calixarene consisting of 8 units, generally just one salicylic acid unit is present (see example 1 of patent EP 954517). Therefore, even in the case of the calixarenes described in patent EP 954517, the number of salifiable units is still low, also making it impossible in this case to prepare neutral and basic detergents with high soap content.

The applicant has found, surprisingly, novel metal compounds of calixarenes not containing sulfur and dispersible in oil, which are able to overcome the disadvantages of the detergent additives of the prior art.

These metal compounds may form part of detergent compositions to be used, as detergent additives, in the preparation of lubricant compositions.

Thus, the present invention relates to a metal compound of calixarene not containing sulfur and dispersible in oil, which can be partially salified, or neutral, or basic or overbased; said calixarene having general formula (I)

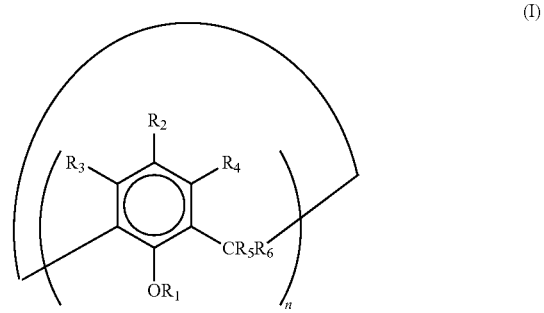

in which:
a) $R_1$, $R_2$, $R_3$ and $R_4$ are independently selected from hydrogen, or a group containing carbon and hydrogen, or a group containing in addition to carbon and hydrogen also heteroatoms, provided that said heteroatoms are not sulfur;
b) one of the two substituents $R_5$ and $R_6$ is hydrogen, while the other may be selected from hydrogen, or a linear or branched alkyl with a number of carbon atoms between 1 and 6;
c) n is the number of units of the calixarene ring and is comprised in the range between 4 and 16;
said calixarene being characterized in that in at least one of the n units of the calixarene ring, preferably in at least two of the n units, at least one of the substituents $R_1$, $R_2$, $R_3$ and $R_4$ contains at least one acid group of carboxylic type available for the reaction with a metal base, with the proviso that said acid group of carboxylic type is not contained in a unit of the calixarene ring derived from salicylic acid.

The present invention further relates to a detergent composition comprising the metal compounds of calixarenes described and claimed in the present patent application.

The present invention further relates to the use of said detergent compositions in lubricant compositions, also called lubricant formulations, and the lubricant compositions themselves, allowing control of the formation of deposits to be obtained that is greater than that obtained with the calixarene detergents of the prior art.

The use of said metal compounds of calixarenes, which contain, relative to the calixarenes of the prior art, a larger number of functional groups fully salifiable by a metal base, makes it possible to obtain detergent compositions with a higher soap content relative to that of the detergent compositions based on calixarenes of the prior art.

In particular, the use of said metal compounds of calixarenes makes it possible to obtain overbased detergent compositions of high alkalinity and with a higher soap content than that of the detergent compositions based on calixarenes of the prior art, while maintaining viscosity values and a sufficiently low level of sediments, such as to make them obtainable with the process for preparing detergent compositions described and claimed in the present patent application.

The detergent compositions comprising the basic, or neutral, or partially salified metal compounds of calixarenes, described and claimed, have excellent detergent properties and are therefore capable of consistently reducing the formation of deposits on the metallic surfaces of the engine, for example in the cylinder/piston zone.

The detergent compositions comprising the overbased metal compounds of calixarenes, described and claimed, as well as having excellent detergent properties, are characterized by a high degree of incorporation of the metal carbonate, preferably calcium carbonate, and therefore by an alkalinity value able to guarantee effective neutralization of the acidity that forms in a lubricant.

DETAILED DESCRIPTION

The present patent application relates to a metal compound of calixarene not containing sulfur and dispersible in oil, which can be partially salified, or neutral, or basic or overbased; said calixarene having general formula (I)

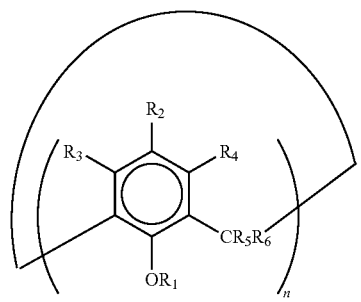

(I)

in which:
a) $R_1$, $R_2$, $R_3$ and $R_4$ are independently selected from hydrogen, or a group containing carbon and hydrogen, or a group containing in addition to carbon and hydrogen also heteroatoms, provided that said heteroatoms are not sulfur;

b) one of the two substituents $R_5$ and $R_6$ is hydrogen, while the other may be selected from hydrogen, or a linear or branched alkyl with a number of carbon atoms between 1 and 6, preferably methyl, ethyl, 1-propyl, 2-propyl, n-butyl, sec-butyl, more preferably methyl or ethyl;

c) n is the number of units of the calixarene ring and is comprised in the range between 4 and 16, preferably between 5 and 12;

said calixarene being characterized in that in at least one of the n units of the calixarene ring, at least one of the substituents $R_1$, $R_2$, $R_3$ and $R_4$ contains at least one acid group of carboxylic type available for the reaction with a metal base, with the proviso that said acid group of carboxylic type is not contained in a unit of the calixarene ring derived from salicylic acid.

In a preferred embodiment the calixarene may comprise at least two units of the n units of the calixarene ring in which at least one of the substituents $R_1$, $R_2$, $R_3$ and $R_4$ contains at least one acid group of carboxylic type, with the proviso that said acid group of carboxylic type is not part of a unit of the calixarene ring derived from salicylic acid.

More preferably, the calixarene may comprise a number of units of the ring, comprised between 2 and n, in which one of the substituents $R_1$ and $R_2$ contains an acid group of carboxylic type, with the proviso that said acid group of carboxylic type is not part of a unit of the calixarene ring derived from salicylic acid.

The heteroatoms present in the metal compounds of calixarenes, described and claimed in the present patent application, are selected from oxygen, nitrogen, phosphorus, boron, and halogens, provided that sulfur is never present. Oxygen is the most preferred among the heteroatoms.

In the metal compounds described and claimed in the present patent application, $R_1$ may preferably be selected from:
  hydrogen; or
  a group containing in addition to carbon and hydrogen also heteroatoms and having a number of carbon atoms between 2 and 24, preferably between 2 and 18, more preferably between 2 and 10, provided that said heteroatoms are not sulfur, in which said group may contain one or more acid groups of carboxylic type available for the reaction with a metal base, more preferably may contain an acid group of carboxylic type; or
  a linear or branched alkyl having a number of carbon atoms between 1 and 40, preferably between 4 and 24, more preferably between 6 and 18.

In the metal compounds described and claimed in the present patent application, more preferably $R_1$ may be selected from:
  hydrogen; or
  a group containing an acid functionality of carboxylic type of formula (II)

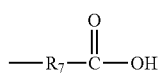

(II)

where $R_7$ may be selected from a divalent group containing carbon and hydrogen, derived from an aliphatic or aromatic hydrocarbon, saturated or unsaturated, having a number of carbon atoms between 1 and 23, preferably between 1 and 17, more preferably between 1 and 9; preferably $R_7$ may be selected from the groups:

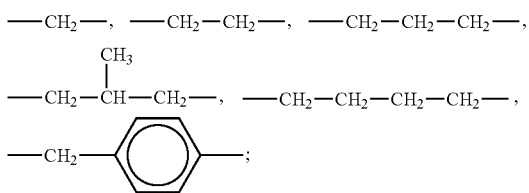

or a linear or branched alkyl having a number of carbon atoms between 4 and 24, preferably between 6 and 18. Even more preferably $R_1$ may be selected from:

hydrogen, or

—$CH_2$—COOH, or

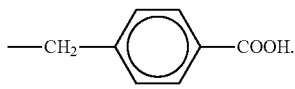

In the metal compounds described and claimed in the present patent application, $R_2$ may preferably be selected from:
- a linear or branched alkyl having a number of carbon atoms between 1 and 40, more preferably between 4 and 24, even more preferably between 6 and 18; or
- a group containing in addition to carbon and hydrogen also heteroatoms and having a number of carbon atoms between 1 and 24, preferably between 1 and 18, more preferably between 1 and 10, provided that said heteroatoms are not sulfur, in which said group may contain one or more acid groups of carboxylic type available for the reaction with a metal base, more preferably may contain an acid group of carboxylic type.

In the metal compounds described and claimed in the present patent application, $R_2$ may preferably be selected from an alkyl having a number of carbon atoms between 6 and 18; or a group of formula —$CH_2COOH$; or a group of formula —$OCH_2COOH$; or a group with formula (III):

(III)

in which $R_8$ is a divalent group containing carbon and hydrogen, derived from a saturated or unsaturated aliphatic hydrocarbon with a number of carbon atoms between 1 and 6, preferably the group —$CH_2$—.

Even more preferably $R_2$ is the tert-octyl group of formula —$C(CH_3)_2CH_2C(CH_3)_3$, or the dodecyl group.

In the metal compounds described and claimed in the present patent application, preferably $R_3$, $R_4$, $R_5$ and $R_6$ are hydrogen simultaneously.

The metal of the metal compounds of calixarenes according to the present invention is derived from the acid-base reaction of the calixarene with a metal base and is selected from the alkali metals, the alkaline-earth metals and any other metal whose basic compounds are capable of forming salts with calixarenes. For the purposes of the present invention, the alkali metals that may be used are selected from Li, Na, K, Rb and Cs; the alkaline-earth metals that may be used are selected from Be, Mg, Ca, Sr and Ba. The preferred metals are the alkaline-earth metals; magnesium and calcium are particularly preferred, and calcium is even more preferred.

The metal content of the metal compounds corresponds to a ratio between the metal equivalents and acid ones of the calixarene from which they are derived between 0.15 and 15, preferably between 0.5 and 10, even more preferably between 0.9 and 8.

Preferred metal compounds according to the present invention are metal compounds of calixarenes not containing sulfur and dispersible in oil, which can be partially salified, neutral, basic or overbased; said calixarene having general formula (I), in which:

1) $R_1$ may preferably be selected from:

hydrogen; or a group containing an acid functionality of carboxylic type of formula (II):

(II)

where $R_7$ may be selected from a divalent group containing carbon and hydrogen, derived from an aliphatic or aromatic hydrocarbon, saturated or unsaturated, having a number of carbon atoms between 1 and 23, preferably between 1 and 17, more preferably between 1 and 9; preferably $R_7$ may be selected from the groups:

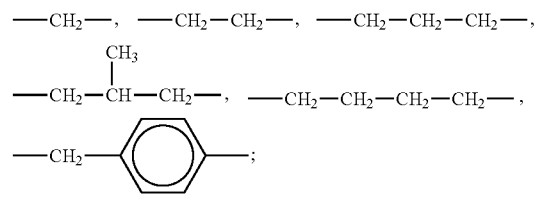

2) $R_2$ may preferably be selected from an alkyl having a number of carbon atoms between 1 and 40, more preferably between 4 and 24, even more preferably between 6 and 18;

3) $R_3$, $R_4$, $R_5$ and $R_6$ are simultaneously hydrogen;

4) n is the number of units of the calixarene ring and is comprised in the range between 4 and 16, preferably between 5 and 12;

5) the number of units of the calixarene ring in which $R_1$ contains an acid group of carboxylic type is between 2 and n.

Further metal compounds that are preferred according to the present invention are metal compounds of calixarenes that are partially salified, neutral, basic or overbased; said calixarene having general formula (I), in which:

1) $R_1$ may preferably be selected from:

hydrogen; or a linear or branched alkyl having a number of carbon atoms between 4 and 24, preferably between 6 and 18;

2) $R_2$ may preferably be selected from a group of formula —$CH_2COOH$; or a group of formula —$OCH_2COOH$; or a group with formula (III):

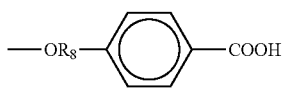

(III)

in which $R_8$ is a divalent group containing carbon and hydrogen, derived from a saturated or unsaturated aliphatic hydrocarbon with a number of carbon atoms between 1 and 6, preferably the group —$CH_2$—;

3) $R_3$, $R_4$, $R_5$ and $R_6$ are simultaneously hydrogen;

4) n is the number of units of the calixarene ring and is comprised in the range between 4 and 16, preferably between 5 and 12;

5) the number of units of the calixarene ring in which $R_2$ contains an acid group of carboxylic type is equal to n.

The calixarenes are well-known cyclic compounds that are derived from the condensation of p-substituted phenols and formaldehyde. Conventionally, the size of the macrocycle of the calixarenes is identified in their nomenclature, indicating such products as calix[n]arenes, in which n denotes the number of aromatic units present in the cyclic product.

The synthesis of calixarenes of formula (I) in which $R_1$=H; $R_3$, $R_4$, $R_5$, $R_6$=H; $R_3$=tert-$C_4H_9$, tert-$C_8H_{17}$, Ph, OPh is known in the prior art and is typically carried out by condensation between p-substituted phenols, preferably with alkyl groups, and formaldehyde at high temperature, as given in the following scheme 1:

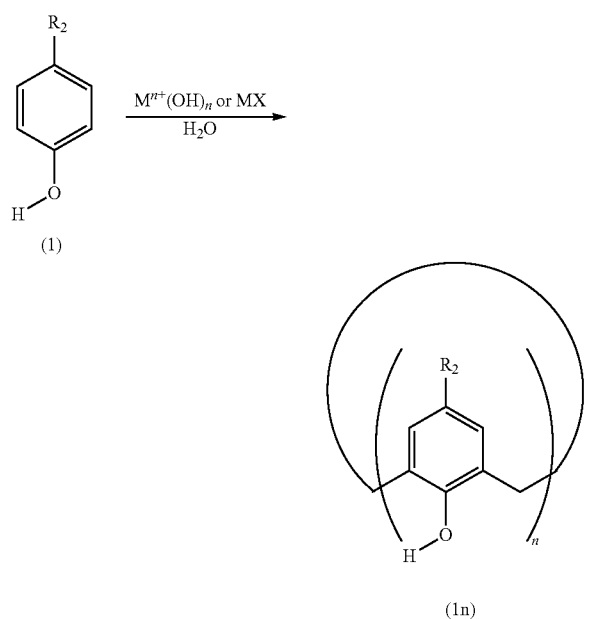

Hydroxides of metals, preferably alkali metals or alkaline-earth metals, as given, for example, in "Gutsche, C. D. et al. Org. Synth. 1990, 68, 234-246", are usually employed as catalysts. Recently, Lewis acids have also been used with good yields, also with the aid of irradiation with microwaves, as given in "Bew, S. P. et al. Chem. Commun. 2007, 975-977; Bew, S. P. et al. J. Org. Chem. 2011, 76, 7076-7083". Typically, the size of the macrocycle may be suitably modulated by changing the cation of the base, the solvent and the temperature of heating. In the case of some phenols, typically p-tert-butylphenol, well-established experimental procedures (for example in "Gutsche, C. D. et al. Org. Synth. 1990, 68, 234-246 and Gutsche, C. D. Org. Prep. Proced. Int. 1992, 25, 137-139") allow the synthesis to be directed with excellent yields (60-90%) towards the products of formula (I) with $R_1$=H; $R_3$, $R_4$, $R_5$, $R_6$=H; $R_2$=tert-$C_4H_9$ and having n=4, 5, 6 or 8.

The calixarenes derived from condensation between formaldehyde and phenols containing long-chain branched alkyl groups ($R_2$=tert-$C_8H_{17}$ or $C_{12}H_{25}$) are particularly interesting for the purpose of the present invention.

These in fact impart excellent oil-solubility to the metal salts derived from them. Therefore p-dodecyl phenol (4-tetrapropylene phenol) is used, which is found to consist of a mixture of phenols mainly para-substituted with branched alkyl groups and corresponding to molecular formulae between $C_{11}H_{23}$ and $C_{14}H_{29}$.

Scheme 2

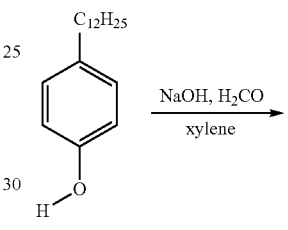

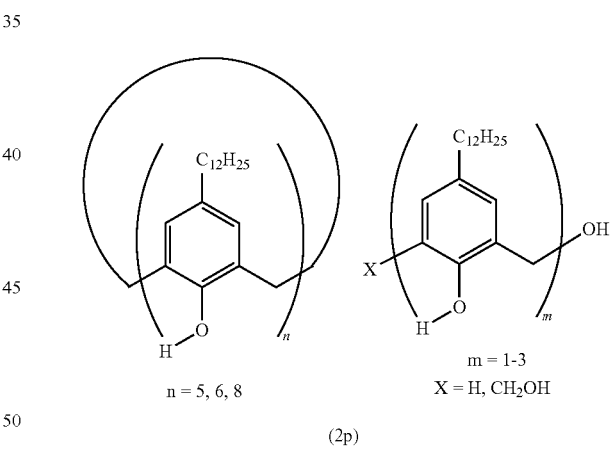

Referring to Scheme 2, p-dodecyl phenol, is reacted in xylene solution with 37 wt. % formaldehyde and NaOH in an inert atmosphere at 120°. After removing the water in the first two hours, it is heated under reflux for a further 4 hours. Then the organic phase is washed with water and the organic solution is concentrated, arriving at a concentration of 77.5 wt % of phenolic products (2p). The products thus obtained consist of 60 wt % of the active part of calix[n]arenes (with n mainly 5, 6, 8) and 40% of linear oligomers (Example 1). In an alternative route of preparation, the xylene may be removed completely at reduced pressure, obtaining a mixture of phenolic products with the same relative composition of cyclic and linear products (Example 2).

The use of p-tert-octyl calix[n]arenes is also interesting. They are synthesized (Example 7) (Scheme 1, $R_2$=tert-$C_8H_{17}$) similarly to the procedure given for p-dodecylphenol, but using p-tert-octylphenol, as reported in the literature (Bocchi V. et al. Tetrahedron 1982, 38, 3, 373-378; Cornforth J. W. et al. J. Pharmacol. 1955, 10, 73).

After removing about 75% of the xylene, addition of 2-propanol leads to the precipitation of the cyclic products alone, corresponding to p-tert-octyl calix[6]- and [8]arenes (relative proportions 2:3), as a white powdery solid (yield=50%), which can thus be isolated from the linear oligomers that remain in the recrystallization water together with small percentages of lower calixarene homologues.

The p-benzyloxycalix[n]arenes (Scheme 1, $R_2$=$OCH_2Ph$) may also be used profitably for the synthesis of acid derivatives suitable for the preparation of detergents. As noted in the literature (Ungaro R. et al. J. Org. Chem. 1997, 62, 6236-6239), p-benzyloxyphenol (1: $R_2$=$OCH_2Ph$, Scheme 1) is reacted with 2M NaOH under reflux in xylene. After removing the water with a Dean-Stark trap and cooling the solution, a solid can be filtered which, on washing with water and then with ethyl ether, leads to the isolation, with 48% yield, of a mixture of p-benzyloxycalix[6]-, -[7]- and -[8]arene in the relative proportions 10:6:84. This mixture of macrocycles alone can be used as it is in subsequent preparation of the acid derivatives or suspended in dichloromethane, refluxed and filtered hot, thus allowing a white solid to be separated consisting only of p-benzyloxycalix[8]arene (in: n=8, $R_2$=$OCH_2Ph$, in Scheme 1).

Once obtained, the condensation products (2p) and (1n) may be functionalized with groups containing carboxyl functionalities (—COOH) capable of forming metal salts.

The general methods for preparing the preferred functionalized calixarenes of the present invention are presented below, as examples.

For the preparation of calixarene derivatives with functionalities of the carboxylic acid type, the calixarene (2p) is alkylated at the phenolic oxygens by reaction with halogen esters, preferably with 2-bromoethyl acetate, after salification of the mixture (2p) of calixarenes and linear products. The mixture of phenolic products (2p) at 77.5 wt % in xylene, further diluted with xylene, is salified with KOH following the removal of water with a Dean-Stark trap. After heating for 12 hours at 130° C. with 1.75 equivalents of 2-bromoethyl acetate, complete functionalization of the phenolic oxygens is obtained. Addition of aqueous KOH and PEG 400 (polyethylene glycol with molecular weight equal to 400), followed by refluxing for 13 hours, leads, as a result of saponification of the carboxyl functions, to potassium carboxylates, which are then acidified with 37 wt % HCl (scheme 3). The product, in the form of acid (3p), is isolated and suitably stored in xylene solution at a concentration of 53 wt % (Example 3).

Scheme 3

2p $\xrightarrow{\begin{array}{l}\text{1. KOH, xylene}\\\text{2. BrCH}_2\text{COOEt}\\\text{3. KOH, H}_2\text{O, PEG400}\\\text{4. HCl}\end{array}}$

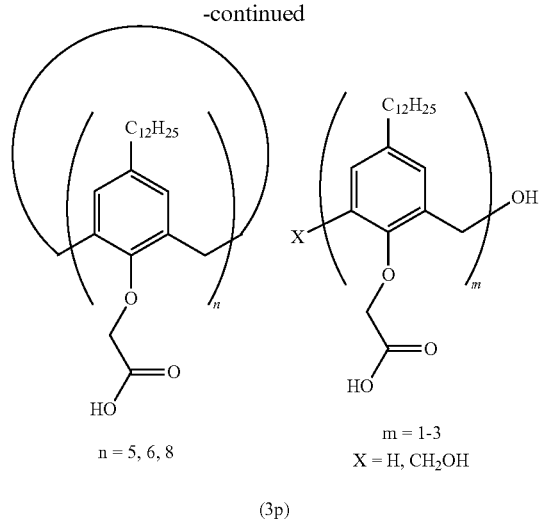

n = 5, 6, 8 m = 1-3
X = H, $CH_2OH$ (3p)

Alternatively, the products 3p may also be obtained by treating the phenolic compounds (2p), as a mixture of cyclic and linear products, with 1.4 equivalents of $K_2CO_3$ and 1.25 equivalents of 2-bromoethyl acetate under reflux in xylene. Reactions similar to those already described of saponification with KOH and PEG 400 and subsequent acidification with HCl give the phenoxy-acetic acids 3p with 95% yield (Example 4).

Using, instead, p-tert-octyl calix[6,8]arene as substrate in the alkylation process (1.30 equivalents of bromoethyl acetate relative to the phenolic groups present and KOH as base), we obtain (Example 8), as a result of saponification and acidification, product (3) (95% yield) fully functionalized with carboxylic acid groups (Scheme 4).

Scheme 4

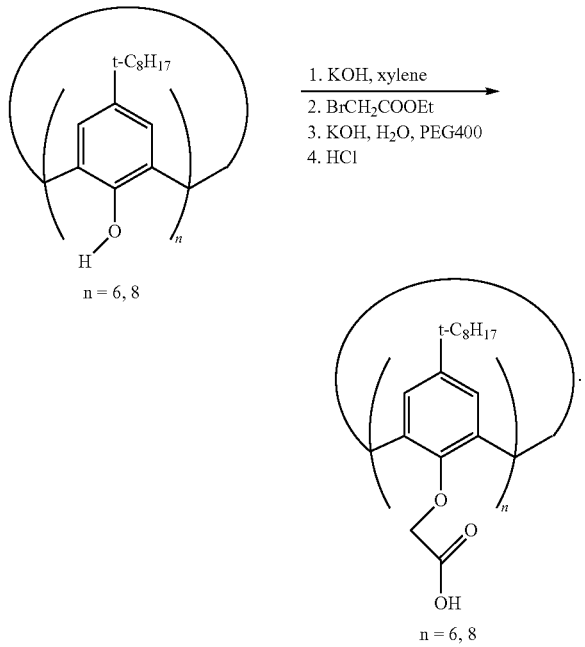

(3)

Using instead, in the alkylation process of the mixture of cyclic and linear phenolic products (2p), a slight excess of 4-(bromomethyl)methyl benzoate (1.30 equivalents relative to the phenolic groups present), we obtain (Example 6), after saponification and acidification, a mixture of compounds (4p) fully functionalized with —OCH$_2$PhCOOH groups (Scheme 5).

Scheme 5

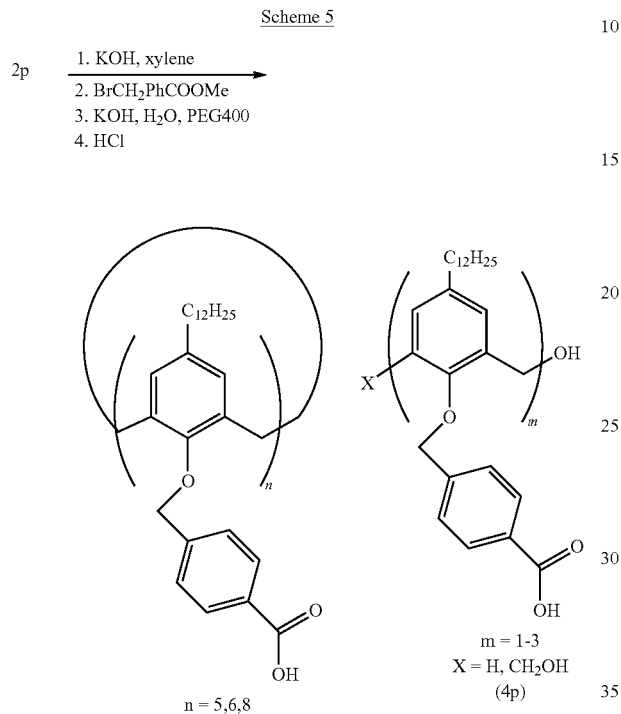

Calixarene derivatives containing carboxylic acid groups, useful for the synthesis of detergents, may also be prepared starting from the p-benzyloxycalix[n]arenes, according to scheme 6 (Bn=CH$_2$Ph).

Scheme 6

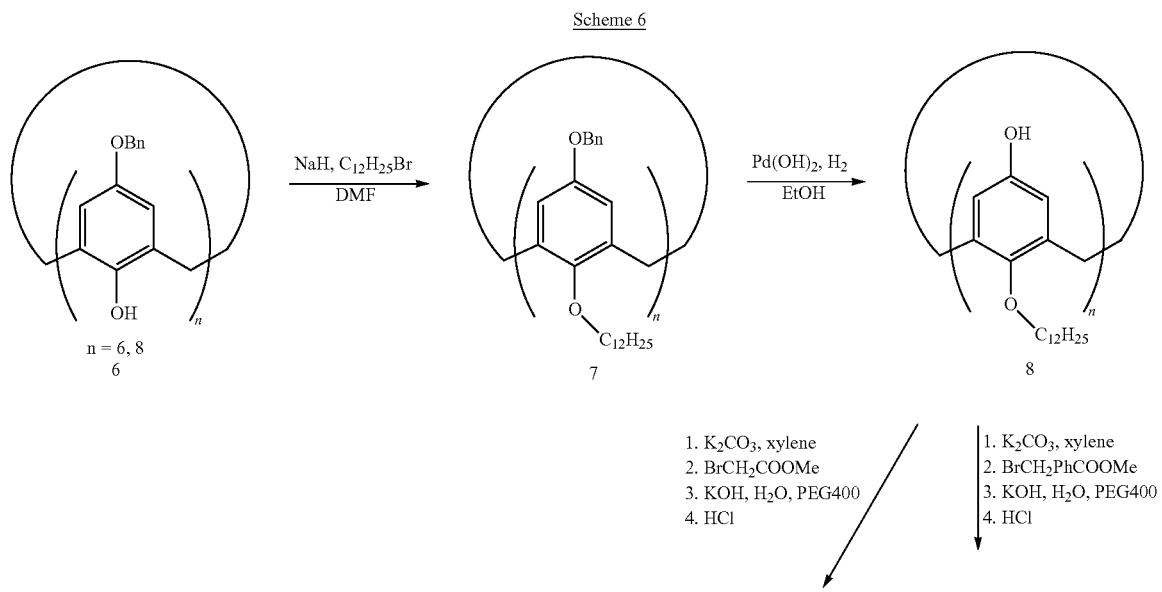

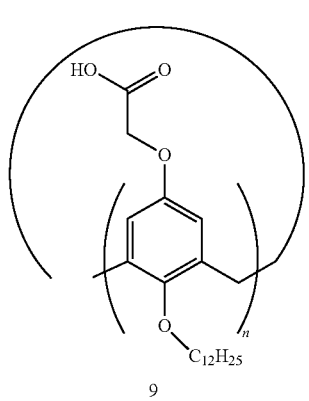

(9)

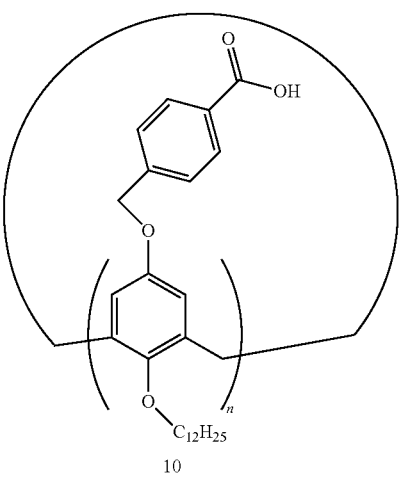

(10)

The mixture of p-benzyloxycalix[n]arenes (6) is treated with NaH and dodecylbromide in DMF at 90° for 12 hours. After stopping the reaction, the alkylated products with dodecyl groups (7) are isolated. These are debenzylated quantitatively to (8) by catalytic hydrogenation in the presence of Pearlman catalyst Pd(OH)2, as reported by Ungaro R. et al. J. Org. Chem. 1997, 62, 6236-6239. Subsequent alkylation with K$_2$CO$_3$ as base and bromoethyl acetate or 4-(bromomethyl)methyl benzoate, followed by saponification and acidification, leads to the acid derivatives (9) or (10), respectively.

Alternatively, chains containing carboxylic acid groups may be inserted following the synthesis pathway given in Scheme 7. p-tert-Butylcalix[8]arene, treated with AlCl$_3$ (0.25 equivalents for each phenol nucleus) for 2 hours at 60° C., in an inert atmosphere, gives the derivative (11), which by subsequent alkylation in phase transfer conditions (PEG 600), with allyl bromide (3 equivalents for each phenol nucleus), allows octa-allyl ether (12) to be obtained.

Derivative (12), treated with N,N-diethylaniline (12 equivalents for each phenol nucleus), leads to derivative (13) as a result of Claisen rearrangement, which is also well known for calixarenes (Gutsche, C. D. et al. J. Org. Chem., 1985, 50, 5802-5806). Compound (13), reacted in the phase transfer conditions described above with KOH and dodecyl bromide, allows the dodecyl ether of p-allylcalix[8]arene (14) to be isolated. Ozonolysis, followed by treatment with hydrogen peroxide, gives the octa-acid 15.

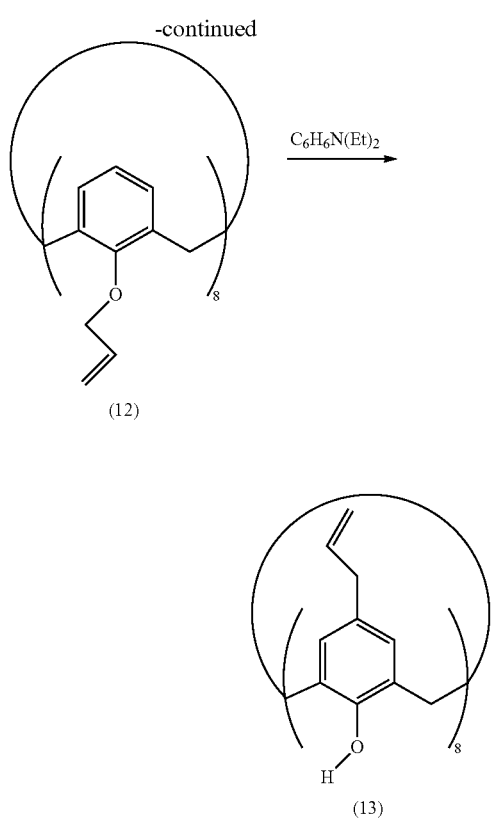

Scheme 7

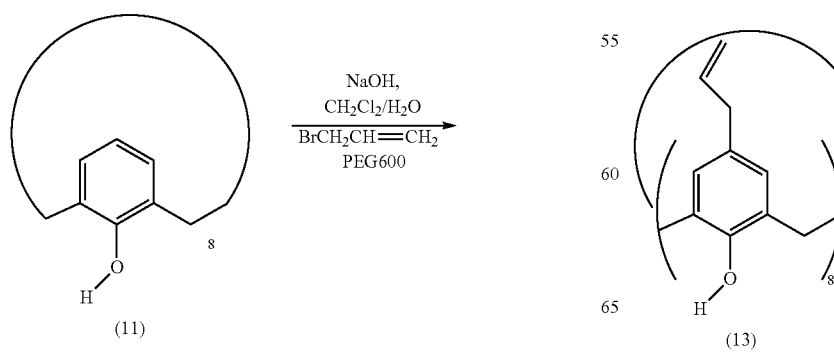

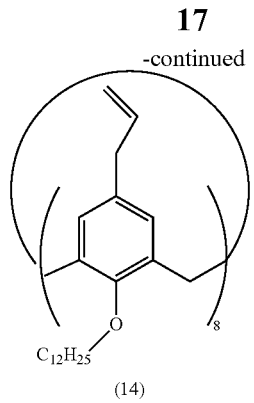

(14)

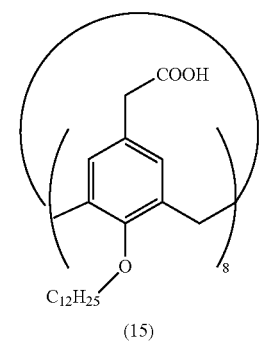

(15)

The synthesis of calixarene derivatives partially functionalized with groups containing the carboxylic acid function is described below.

Using a shortfall of 2-bromoethyl acetate (0.35 equivalents relative to the phenolic groups present) during the alkylation process of the mixture of cyclic and linear phenolic products (2p) and the subsequent saponification, described above, a mixture of compounds (5p) partially functionalized with —OCH$_2$COOH and —OH groups and having an average degree of functionalization (n/3 and m/3) with —OCH$_2$COOH groups equal to about 33% (Scheme 8), is obtained (Example 5). The —OCH$_2$COOH groups are distributed randomly in the various units of the macrocycle.

Scheme 8

2p  1. KOH, xylene
    2. BrCH$_2$COOEt
    3. KOH, H$_2$O, PEG400
    4. HCl

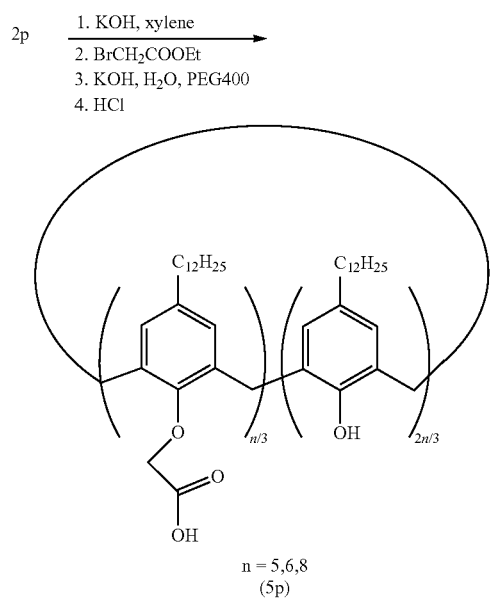

n = 5,6,8
(5p)

+

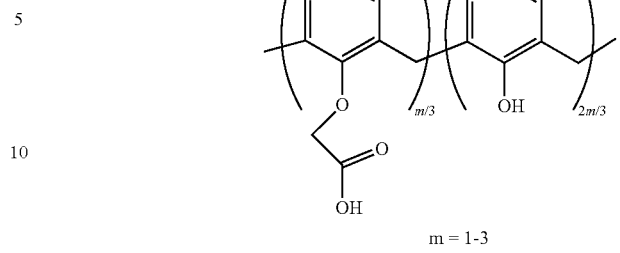

m = 1-3

Similarly, by treating p-tert-octyl calix[6,8]arene (Scheme 9) with 0.52 equivalents of bromoethyl acetate per phenolic hydroxyl in xylene, using K$_2$CO$_3$ as base, followed by saponification and acidification, we obtain a mixture of partially functionalized p-tert-octyl calix[6,8]arenes, with an average degree of functionalization with hydroxycarbonylmethyl groups equal to 50% (example 9).

Scheme 9

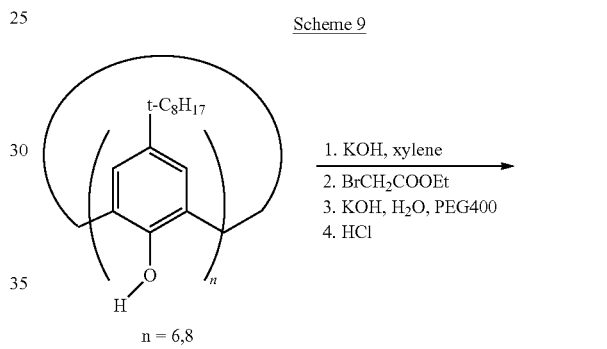

n = 6,8

1. KOH, xylene
2. BrCH$_2$COOEt
3. KOH, H$_2$O, PEG400
4. HCl m = 3-5

The present invention further relates to a detergent composition comprising the metal compounds of calixarenes described and claimed in the present patent application.

The metal compounds described and claimed in the present patent application are formed during preparation of said compositions, by a method that will be described hereunder.

These detergent compositions comprise the metal compounds described and claimed in the present text at a concentration, expressed as the percentage by weight of said metal compounds of calixarenes of formula (I) with respect to the detergent composition, between 5% and 100%, preferably between 15% and 70%.

In a preferred embodiment the detergent compositions may comprise one or more lubricant base oils at a concentration, expressed as percentage of the base oil with respect to the detergent composition, between 10% and 90%, preferably between 20% and 70%.

The base oils used in the present invention may be selected from base oils of mineral, synthetic, vegetable, and animal origin and mixtures thereof.

The oils of mineral origin are obtained from well-known processes of petroleum refining, for example distillation, dewaxing, deasphalting, dearomatization and hydrogenation.

The oils of synthetic origin preferably include hydrocarbon oils, for example polymerized and hydrogenated terminal or internal olefins; alkylbenzenes; polyphenyls; alkylated diphenyl ethers; polyalkyleneglycols and derivatives, where the terminal hydroxyl groups have been modified for example by esterification or etherification.

Another class of synthetic lubricating oils preferably comprises esters of synthetic carboxylic acids or of animal or vegetable origin with a variety of alcohols or polyols.

A further class of synthetic lubricating oils preferably comprises esters of carbonic acid with a variety of alcohols and polyols.

The vegetable oils are preferably selected from soya oil, palm oil, or castor oil, while the oils of animal origin are preferably selected from tallow oil, lard oil, and whale oil.

Another method of classification of base oils is that defined by the American Petroleum Institute (API) in the publication "Engine Oil Licensing and Certification System" (API EOLCS, 1507—Industry Services Department, Fourteenth Edition, December 1996, Addendum 1, December 1998). The base oils are subdivided into five groups depending on their physicochemical characteristics and composition.

According to this classification, the base oils included in the detergent compositions described and claimed in the present text may belong to all the aforementioned API Groups, preferably to the API groups selected from I, II, III or IV and even more preferably to the API Groups selected from I, II or III.

The detergent compositions described and claimed in the present patent application may further comprise one or more metal compounds of organic acid compounds selected from:

A) metal compounds, partially salified, neutral, basic and overbased of oligomeric compounds of formula (IV)

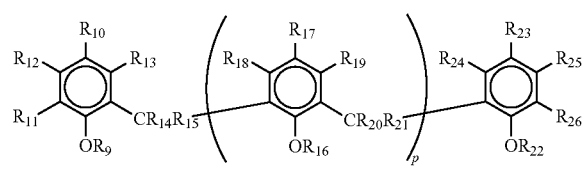

or of monomeric compounds of formula (V)

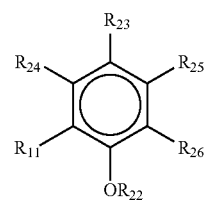

(V)

in which:
$R_9$, $R_{10}$, $R_{12}$, $R_{13}$, $R_{16}$, $R_{17}$, $R_{18}$, $R_{19}$, $R_{22}$, $R_{23}$, $R_{24}$ and $R_{25}$ may be selected independently from hydrogen, a group containing carbon and hydrogen, a group containing in addition to carbon and hydrogen also heteroatoms, provided that sulfur is not present;

$R_{14}$, $R_{15}$, $R_{20}$ and $R_{21}$ are selected from hydrogen or an alkyl with a number of carbon atoms between 1 and 6; preferably one of the two substituents $R_{14}$ and $R_{15}$ and similarly one of the two substituents $R_{20}$ and $R_{21}$ are hydrogen, while the others are hydrogen or alkyls;

$R_{11}$ and $R_{26}$ are independently selected from hydrogen, the hydroxymethylene group —$CH_2OH$, methyl and the hydroxycarbonyl group —COOH;

p is a number in the range between 0 and 20, preferably between 0 and 6;

B) metal compounds, partially salified, neutral, basic or overbased of carboxylic, dicarboxylic and polycarboxylic acids containing a number of carbon atoms between 6 and 80, preferably of alkyl carboxylic acids of formula (VI):

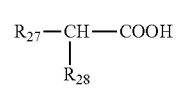

(VI)

in which:
$R_{27}$ may be selected from a linear or branched alkyl or alkenyl group, containing a number of carbon atoms between 6 and 40 and preferably between 10 and 24;
$R_{28}$ may be selected from hydrogen, an alkyl group containing from 1 to 4 carbon atoms, or —$CH_2COOH$;

C) metal compounds, partially salified, neutral, basic or overbased of compounds of formula (VII):

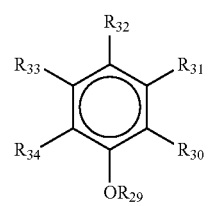

(VII)

in which $R_{29}$, $R_{30}$, $R_{31}$, $R_{32}$, $R_{33}$, and $R_{34}$ may be selected independently from hydrogen, a group containing carbon and hydrogen, a group containing in addition to carbon and hydrogen also heteroatoms, provided that sulfur is not present;

D) metal compounds, partially salified, neutral, basic or overbased of phenols substituted with linear or branched alkyl groups, in number between 1 and 3, each containing a number of carbon atoms between 2 and 40, preferably of alkylphenols of formula (VIII):

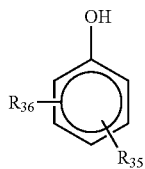

(VIII)

in which $R_{35}$ and $R_{36}$ may be selected independently from hydrogen and an alkyl group containing a number of carbon atoms between 2 and 40, more preferably between 4 and 24;

E) metal compounds, partially salified, neutral, basic or overbased of salicylic acids substituted with linear or branched alkyl groups, in number between 1 and 3, each containing a number of carbon atoms between 2 and 40, preferably of alkyl salicylic acids of formula (IX):

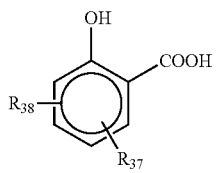

(IX)

in which $R_{37}$ and $R_{38}$ may be selected independently from hydrogen and an alkyl group containing a number of carbon atoms between 2 and 40, more preferably between 4 and 24;

F) metal compounds partially salified, basic or overbased of the calixarene of general formula (Z), having substituents of hydroxyl type:

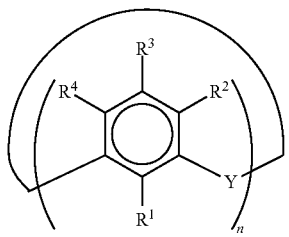

(Z)

in which Y is a divalent bridge group, preferably Y is the —CH$_2$— group; $R_3$ is a group containing carbon and hydrogen or a group containing in addition to carbon and hydrogen also heteroatoms, preferably $R_3$ is an alkyl with a number of carbon atoms between 1 and 40; n is an integer between 3 and 9, and alternatively $R_1$ is hydroxyl and $R_2$ and $R_4$ are independently hydrogen, or a group containing carbon and hydrogen, or a group containing in addition to carbon and hydrogen also heteroatoms, preferably $R_1$ is the hydroxyl group; or $R_2$ and $R_4$ are hydroxyl and $R_1$ is independently hydrogen, or a group containing carbon and hydrogen, or a group containing in addition to carbon and hydrogen also heteroatoms.

Referring to component (A), in the detergent compositions described and claimed in the present text, the substituents $R_9$, $R_{16}$ and $R_{22}$ may preferably be selected independently from hydrogen; or a group containing in addition to carbon and hydrogen also heteroatoms and having a number of carbon atoms between 2 and 24, preferably between 2 and 18, more preferably between 2 and 10, provided that said heteroatoms are not sulfur; or an alkyl having a number of carbon atoms between 1 and 40, preferably between 4 and 24, more preferably between 6 and 18. The preferred heteroatom is oxygen. Said groups, containing in addition to carbon and hydrogen also heteroatoms, may contain one or more acid groups of carboxylic type available for the reaction with a metal base, more preferably may contain an acid group of carboxylic type.

More preferably, the substituents $R_9$, $R_{16}$ and $R_{22}$ may be selected from hydrogen; or a group of formula (II) containing an acid functionality of carboxylic type; or an alkyl having a number of carbon atoms between 4 and 24, preferably between 6 and 18. Even more preferably $R_9$, $R_{16}$ and $R_{22}$ may be selected from:
  hydrogen; or
  —CH$_2$—COOH; or

Referring to component (A), in the detergent compositions described and claimed in the present text, the substituents $R_{10}$, $R_{17}$ and $R_{23}$ may be selected from an alkyl having a number of carbon atoms between 1 and 40, preferably between 4 and 24, even more preferably between 6 and 18; or a group containing in addition to carbon and hydrogen also heteroatoms and having a number of carbon atoms between 1 and 24, preferably between 1 and 18, more preferably between 1 and 10, provided that said heteroatoms are not sulfur. The preferred heteroatom is oxygen. Said groups, containing in addition to carbon and hydrogen also heteroatoms, may contain one or more acid groups of carboxylic type available for the reaction with a metal base, more preferably may contain an acid group of carboxylic type. More preferably $R_{10}$, $R_{17}$ and $R_{23}$ are selected from:
  an alkyl having a number of carbon atoms between 6 and 18; or
  a group of formula —CH$_2$COOH; or
  a group of formula —OCH$_2$COOH; or
  a group with formula (III).

Even more preferably $R_{10}$, $R_{17}$ and $R_{23}$ are the tert-octyl group of formula —C(CH$_3$)$_2$CH$_2$C(CH$_3$)$_3$, or the dodecyl group.

Referring to component (A), in the detergent compositions described and claimed in the present text, preferably $R_{14}$, $R_{15}$, $R_{20}$ and $R_{21}$ are hydrogen simultaneously.

The compounds of formula (IV) are linear oligomeric compounds, while the compounds of formula (V) are monomeric compounds; both may result from the synthesis of the calixarenes of formula (I).

The metal of the metal compounds of compounds of formula (IV) and (V) is selected from the alkali metals, the alkaline-earth metals and any other metal whose basic compounds are capable of forming salts with the compounds of formula (IV) and (V). For the purposes of the present invention, the alkali metals that may be used are selected from Li, Na, K, Rb and Cs; the alkaline-earth metals that may be used are selected from Be, Mg, Ca, Sr and Ba. The preferred metals are the alkaline-earth metals; magnesium and calcium are particularly preferred, and calcium is even more preferred. Preferably the metal is the same as that of the metal compounds of the calixarenes of formula (I).

When included in the detergent composition according to the present invention, the metal compounds (A) are present at a concentration, expressed as the total percentage by weight of said metal compounds (A) relative to the detergent composition, between 1% and 70%, preferably between 4% and 50%.

Referring to component (B), in the detergent compositions described and claimed in the present text, the saturated alkyl carboxylic acids of formula (VI) are preferably selected from capric acid, lauric acid, myristic acid, stearic acid, isostearic acid, arachidic acid, behenic acid and lignoceric acid; while the unsaturated carboxylic acids of formula (VI) are preferably selected from lauroleic acid, myristoleic acid, palmitoleic acid, oleic acid, gadoleic acid, erucic acid, linoleic acid and linolenic acid. Mixtures of acids may be used, for example mixtures of acids, both synthetic and natural, containing both saturated acids and unsaturated acids.

The preferred alkyl carboxylic acids are isostearic acid and stearic acid.

The metal of the metal compounds of carboxylic acids is selected from the alkali metals, the alkaline-earth metals and any other metal whose basic compounds are capable of forming salts with carboxylic acids. For the purposes of the present invention, the alkali metals that may be used are selected from Li, Na, K, Rb and Cs; the alkaline-earth metals that may be used are selected from Be, Mg, Ca, Sr and Ba. The preferred metals are the alkaline-earth metals; magnesium and calcium are particularly preferred, and calcium is even more preferred. Preferably the metal is the same as that of the metal compounds of calixarenes of formula (I).

When included in the detergent composition according to the present invention, the metal compounds (B) are present at a concentration, expressed as the percentage by weight of said metal compounds (B) based on the detergent composition, between 1% and 80%, preferably between 5% and 60%.

Referring to component (C), in the detergent compositions described and claimed in the present text, preferably the substituents $R_{30}$, $R_{31}$, $R_{33}$ and $R_{34}$ are hydrogen simultaneously.

Preferably $R_{29}$ may be selected from hydrogen; or a group containing in addition to carbon and hydrogen also heteroatoms and having a number of carbon atoms between 2 and 24, preferably between 2 and 18, more preferably between 2 and 10, provided that said heteroatoms are not sulfur, the preferred heteroatom being oxygen; or an alkyl having a number of carbon atoms between 1 and 40, preferably between 4 and 24, more preferably between 6 and 18. Said groups, containing in addition to carbon and hydrogen also heteroatoms, may contain one or more acid groups of carboxylic type available for the reaction with a metal base, more preferably may contain an acid group of carboxylic type.

More preferably, $R_{29}$ may be selected from hydrogen; or a group of formula (II) containing an acid functionality of carboxylic type; or an alkyl having a number of carbon atoms between 4 and 24, preferably between 6 and 18.

Even more preferably, $R_{29}$ may be selected from:
—$CH_2$—COOH; or

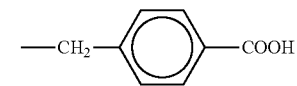

Preferably $R_{32}$ may be selected from an alkyl having a number of carbon atoms between 1 and 40, even more preferably between 6 and 18; or a group containing in addition to carbon and hydrogen also heteroatoms and having a number of carbon atoms between 1 and 24, preferably between 1 and 18, more preferably between 1 and 10, provided that said heteroatoms are not sulfur, the preferred heteroatom being oxygen. Said groups, containing in addition to carbon and hydrogen also heteroatoms, may contain one or more acid groups of carboxylic type available for the reaction with a metal base, more preferably may contain an acid group of carboxylic type. More preferably $R_{32}$ is selected from:
  an alkyl having a number of carbon atoms between 6 and 18; or
  a group of formula —$CH_2COOH$; or
  a group of formula —$OCH_2COOH$; or
  a group with formula (III).

Even more preferably, $R_{32}$ is an alkyl selected from the tert-octyl group of formula $C(CH_3)_2CH_2C(CH_3)_3$ and the dodecyl group.

The preferred compounds of formula (VII) are:

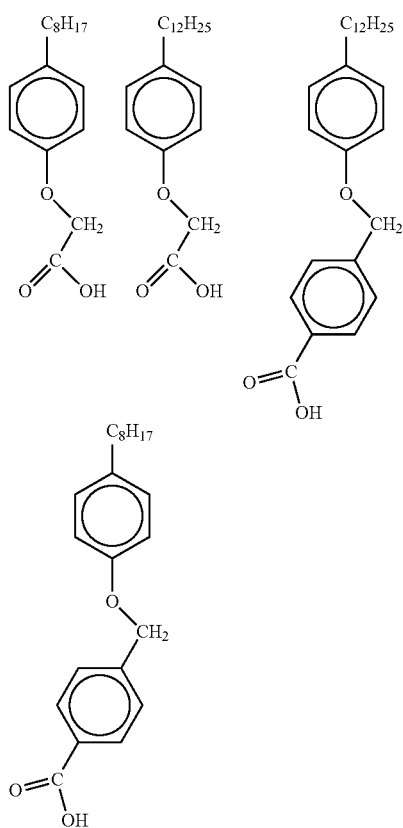

The metal of the metal compounds of compounds of formula (VII) is selected from the alkali metals, the alkaline-earth metals and any other metal whose basic compounds are capable of forming salts with the compounds of formula (VII). For the purposes of the present invention, the alkali metals that may be used are selected from Li, Na, K, Rb and Cs; the alkaline-earth metals that may be used are selected from Be, Mg, Ca, Sr and Ba. The preferred metals are the alkaline-earth metals; magnesium and calcium are particularly preferred, and calcium is even more preferred. Preferably the metal is the same as that of the metal compounds of calixarenes of formula (I).

When included in the detergent composition according to the present invention, the metal compounds (C) are present at a concentration between 1% and 70%, preferably between 4% and 50%, said concentration being expressed as the percentage by weight of said metal compounds (C) based on the detergent composition.

Referring to component (D), in the detergent compositions described and claimed in the present text, the preferred alkylphenols are p-dodecylphenol and p-tert-octylphenol.

The metal of the metal compounds of alkylphenols of formula (VIII) is selected from the alkali metals, the alkaline-earth metals and any other metal whose basic compounds are capable of forming salts with the alkylphenols. For the purposes of the present invention, the alkali metals that may be used are selected from Li, Na, K, Rb and Cs; the alkaline-earth metals that may be used are selected from Be, Mg, Ca, Sr and Ba. The preferred metals are the alkaline-earth metals; magnesium and calcium are particularly preferred, and calcium is even more preferred. Preferably the metal is the same as that of the metal compounds of calixarenes of formula (I).

When included in the detergent composition according to the present invention, the metal compounds (D) are present at a concentration between 1% and 50%, preferably between 4% and 30%, said concentration being expressed as the percentage by weight of said metal compounds (D) based on the detergent composition.

Referring to component (E), in the detergent compositions described and claimed in the present text, the metal of the metal compounds of the alkyl salicylic acids of formula (IX) is selected from the alkali metals, the alkaline-earth metals and any other metal whose basic compounds are capable of forming salts with the alkyl salicylic acids. For the purposes of the present invention, the alkali metals that may be used are selected from Li, Na, K, Rb and Cs; the alkaline-earth metals that may be used are selected from Be, Mg, Ca, Sr and Ba. The preferred metals are the alkaline-earth metals; magnesium and calcium are particularly preferred, and calcium is even more preferred. Preferably the metal is the same as that of the metal compounds of calixarenes of formula (I).

When included in the detergent composition according to the present invention, the metal compounds (E) are present at a concentration between 1% and 50%, preferably between 4% and 30%, said concentration being expressed as the percentage by weight of said metal compounds (E) based on the detergent composition.

Referring to component (F), in the detergent compositions described and claimed in the present text, the metal of the metal compounds of calixarenes of formula (Z) is selected from the alkali metals, the alkaline-earth metals and any other metal whose basic compounds are capable of forming salts with calixarenes of formula (Z). For the purposes of the present invention, the alkali metals that may be used are selected from Li, Na, K, Rb and Cs; the alkaline-earth metals that may be used are selected from Be, Mg, Ca, Sr and Ba. The preferred metals are the alkaline-earth metals; magnesium and calcium are particularly preferred, and calcium is even more preferred. Preferably the metal is the same as that of the metal compounds of calixarenes of formula (I).

Preferably the metal is the same as that of the metal compounds of calixarenes of formula (I).

When included in the detergent composition according to the present invention, the metal compounds (F) are present at a concentration between 1% and 50%, preferably between 4% and 30%, said concentration being expressed as the percentage by weight of said metal compounds (F) based on the detergent composition.

The detergent compositions, described and claimed in the present patent application, have a value of TBN (Total Base Number), expressed in mg KOH/g, greater than 20, preferably between 50 and 550, even more preferably between 70 and 450.

The present invention further relates to a process for preparing detergent compositions containing the metal compounds of calixarenes of formula (I), partially salified, neutral and basic, described and claimed in the present patent application.

Said process comprises reacting, according to a salification reaction, a calixarene of general formula (I), as described in the present patent application, with a metal base, in the presence of a reaction solvent or of a mixture of reaction solvents, and optionally in the presence of a lubricant base oil or a mixture of lubricant base oils. Optionally, another reactant may be present during the reaction: an organic acid compound or a mixture of organic acid compounds.

The salification reaction may be carried out at a temperature between 30° C. and 200° C., preferably between 40° C. and 160° C., at a pressure that ranges between 0.01 bar and 1.5 bar, preferably between 0.04 bar and 1.2 bar, and removing the water of reaction by distillation. Selection of the optimum temperature depends on the nature of the solvent used. The aim of this preparation process is not only to prepare the metal compounds of calixarenes according to the present invention, but also to obtain a stable colloidal dispersion of said compounds in a lubricant base oil. However, it is not easy to obtain said stable colloidal dispersion, in fact, if the process is carried out without all the necessary expedients, the detergent composition may be difficult to filter or coagulation of the colloid may even occur, with formation of gel.

During synthesis of the calixarenes of formula (I), described in the present patent application, there may also be formation of linear oligomeric compounds of formula (IV) and monomers of formula (V), which then form a mixture with the aforesaid calixarenes. This mixture may be used directly as a reactant in the process described and claimed in the present text.

The compounds of formula (IV) and (V), if present in a mixture together with the calixarenes of formula (I), may be present at a concentration that is between 5% and 80%, preferably between 20% and 50%, said concentration being expressed as the total percentage by weight of said compounds (IV) and (V) relative to the mixture.

The calixarenes of formula (I) may moreover be obtained in a mixture with one or more solvents and said mixture may be used directly as a reactant in the process described and claimed in the present text.

Said solvent may be selected from: aromatic or aliphatic hydrocarbons, preferably toluene and xylene; aliphatic or aromatic ethers with a number of carbon atoms between 4 and 20; aliphatic or aromatic ketones with a number of carbon atoms between 4 and 20; esters of carboxylic acids with a number of carbon atoms between 4 and 20; or alcohols with a number of carbon atoms between 4 and 20. The preferred solvents are toluene and xylene.

The metal base is a basic compound of a metal capable of forming, with the calixarenes, the partially salified, neutral and basic metal compounds described and claimed in the present text. Preferably the metal base is a basic compound of an alkaline-earth metal, or of an alkali metal. For the purposes of the present invention, the alkali metals that may be used are selected from Li, Na, K, Rb and Cs; the alkaline-earth metals that may be used are selected from Be, Mg, Ca, Sr and Ba. A basic compound of an alkaline-earth metal selected from calcium and magnesium is more preferred, and even more preferably it is a basic compound of calcium.

The metal base is preferably an oxide or a hydroxide of an alkaline-earth metal or alkali metal, more preferably an oxide or a hydroxide of an alkaline-earth metal selected from calcium or magnesium, even more preferably it is calcium hydroxide.

The metal base may be added completely at the beginning of the reaction, or may be added partly at the beginning and partly at various intermediate time points of the reaction; preferably the metal base may be supplied in a single addition at the beginning of the reaction.

The amount of metal base used in the process according to the present invention may correspond to a ratio that ranges between 0.4 and 4, preferably between 0.6 and 2, said ratio being calculated between the metal base equivalents and the sum of the acid equivalents of the calixarene of formula (I) including the acid equivalents of the optional organic acid compound, or of the optional mixture of organic acid compounds.

The organic acid compounds that may be used as optional reactants in the process described and claimed, may preferably be selected from one or more of the following compounds:

G) carboxylic, dicarboxylic and polycarboxylic acids containing a number of carbon atoms between 6 and 100; preferably alkyl carboxylic acids of formula (VI);
H) a compound of formula (VII);
I) phenols substituted with linear or branched alkyl groups, in number between 1 and 3, each containing a number of carbon atoms between 4 and 40, preferably alkylphenols of formula (VIII);
J) salicylic acids substituted with linear or branched alkyl groups, in number between 1 and 3, each containing a number of carbon atoms between 2 and 40, preferably alkyl-salicylic acids of formula (IX);
K) calixarenes of general formula (Z) having substituents of hydroxyl type.

These organic acid compounds may also include a solvent, or a mixture of solvents. Said solvent may preferably be selected from aromatic or aliphatic hydrocarbons, more preferably toluene and xylene; aliphatic or aromatic ethers with a number of carbon atoms between 4 and 20; aliphatic or aromatic ketones with a number of carbon atoms between 4 and 20; esters of carboxylic acids with a number of carbon atoms between 4 and 20; alcohols with a number of carbon atoms between 4 and 20, and mixtures thereof. The preferred solvents are toluene and xylene.

These organic acid compounds, when used in the process described and claimed, are introduced in an amount that is between 5% and 90%, preferably between 20% and 70%, said quantity being calculated as the percentage by weight of the organic acid compound, or mixture of organic acid compounds, excluding the solvent, relative to the mixture containing said acid compound, or mixtures thereof, and the calixarene of formula (I), excluding the solvents.

The salification reaction between the calixarene of general formula (I) and the metal base is carried out in the presence of a reaction solvent, or a mixture thereof, which is not necessarily that optionally present mixed with the calixarenes of formula (I) or with the organic acid compounds.

These reaction solvents may be selected from:

L) an alcohol with an acyclic or cyclic alkyl, or alkaryl chain, containing a number of carbon atoms between 1 and 16; preferably selected from methanol, ethanol, propanol, isopropanol, butanol, cyclohexanol, 2-ethylhexanol, dodecanol, benzyl alcohol;
M) a polyhydroxylated aliphatic hydrocarbon having a number of carbon atoms between 2 and 4; preferably selected from ethylene glycol, propylene glycol or glycerol;
N) a dialkylene glycol or a trialkylene glycol in which the alkylene group contains from 2 to 4 carbon atoms; preferably selected from diethylene glycol, dipropylene glycol or triethylene glycol;
O) a monoalkylene glycol alkyl ether, or a polyalkylene glycol alkyl ether of formula:

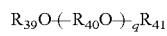

in which $R_{39}$ is an alkyl group containing a number of carbon atoms between 1 and 6; $R_{40}$ is a divalent group containing carbon and hydrogen with a number of carbon atoms between 2 and 4; $R_{41}$ is hydrogen or an alkyl group with a number of carbon atoms between 1 and 6; q is an integer between 1 and 6;
P) water;
Q) a ketone with alkyl or alkaryl or aromatic groups, each containing a number of carbon atoms between 1 and 10; preferably selected from acetone, methyl ethyl ketone, methyl isobutyl ketone, cyclohexanone or acetophenone;
R) an ester of an aliphatic or aromatic carboxylic acid with a number of carbon atoms between 1 and 10, preferably selected from ethyl acetate and butyl acetate;
S) aliphatic and aromatic ethers containing a number of carbon atoms between 2 and 20;
T) an aromatic or aliphatic hydrocarbon with a number of carbon atoms between 5 and 16;
U) and mixtures thereof.

The aromatic hydrocarbon solvent (T) is preferably selected from benzene, substituted benzenes and mixtures thereof; more preferably it is selected from toluene, xylene or halogen-substituted benzenes and mixtures thereof. The aliphatic hydrocarbon solvent (T) is preferably selected from the aliphatic paraffins, cycloaliphatic paraffins and mixtures thereof; more preferably it is selected from hexane, heptane and mixtures thereof.

The preferred solvents (O) include the monomethyl ethers or the dimethyl ethers of ethylene glycol, of diethylene glycol, of triethylene glycol or of tetraethylene glycol, and mixtures thereof.

In the process according to the present invention it is possible to use a single reaction solvent, but more preferably a mixture of reaction solvents is used.

Said mixture of reaction solvents may comprise one or more reaction solvents capable of dissolving the calixarenes of formula (I) and, if present, the organic acid compounds and mixtures thereof; and one or more polar reaction solvents capable of dissolving the metal base, at least partially. The reaction solvent or mixture of reaction solvents capable of dissolving the calixarenes of formula (I), the organic acid compounds and mixtures thereof is preferably selected from toluene, heptane, 2-ethylhexyl alcohol, cyclohexanone and butyl acetate. The reaction solvent or mixture of reaction solvents capable of dissolving the metal base, at least partially, is preferably selected from ethylene glycol, methanol, glycerol, diethylene glycol monomethyl ether.

The preferred mixtures of reaction solvents are the mixture of ethylene glycol with 2-ethylhexanol, the mixture of glycerol with 2-ethylhexanol and the mixture of methanol with toluene.

The reaction solvents may be added in an amount corresponding to a percentage by weight between 10% and 90%, preferably between 30% and 70%, said percentage being calculated on the sum of the components making up the reaction mixture, including reaction solvents.

In a preferred embodiment the reaction solvent is a mixture consisting of ethylene glycol and 2-ethylhexyl alcohol, containing an amount of ethylene glycol, expressed as percentage by weight based on the mixture of the two solvents, between 3% and 60%, preferably between 8% and 40%.

The reaction solvents may be added together in a single addition, or may be added individually, and addition may be fractional in the various steps of the process described and claimed in the present text.

In a preferred embodiment, the salification reaction between calixarene of general formula (I) and the metal base may be carried out in the presence of a lubricant base oil or a mixture of lubricant base oils.

The lubricant base oil acts as solvent for the metal compounds of calixarenes and, if present, for the metal salts of organic acids, to obtain a colloidal dispersion of said metal compounds in the lubricant base oil.

The lubricant base oils used in the process according to the present invention are those described above in the present text, used in particular in the detergent compositions and in the lubricant compositions described and claimed in the present patent application.

The lubricant base oil may be used in an amount between 5% and 70%, preferably between 10% and 40%, said quantity being calculated as the percentage by weight of the base oil relative to the sum of the components making up the reaction mixture.

In a further preferred embodiment, the process for preparing the detergent compositions comprising metal compounds, partially salified, neutral and basic of calixarenes of formula (I) may be carried out by adding, in any order, during the salification reaction, the calixarenes of formula (I), the metal base, the optional organic acids or mixtures thereof, the reaction solvents or mixtures thereof, and the optional base oil or mixtures of base oils.

In a further preferred embodiment, the process for preparing the detergent compositions containing the partially salified, neutral and basic metal compounds described and claimed in the present text, may be carried out by mixing together, in a first step, a calixarene of formula (I), optionally an organic acid compound or a mixture thereof, the lubricant base oil or a mixture thereof, and then adding a metal base and the reaction solvents or the mixture of reaction solvents.

The solvents optionally present, mixed with the calixarenes of formula (I) or with the organic acid compounds, may be removed by distillation before starting the reaction, i.e. before adding the metal base and the optional reaction solvents.

During the salification reaction, the metal base may be added in a single addition or with fractional additions; preferably with a single addition. The final reaction product is preferably obtained as a solution in oil, separating the reaction solvent or the mixture of reaction solvents by distillation.

Distillation of the solvents is carried out by increasing the temperature to a maximum value of 230° C., preferably up to 200° C. and maintaining the product at this temperature for the necessary time to obtain complete removal of the solvents. Distillation of the solvents may be carried out at atmospheric pressure or at reduced pressure; preferably it is carried out at reduced pressure.

Following removal of the solvents by distillation, the resultant product is filtered using a filter aid, or alternatively it may be centrifuged.

As an alternative, following distillation of the reaction solvents, a further solvent, preferably selected from 2-ethylhexanol, heptane, xylene or toluene, may be added to the resultant product, in an amount, expressed as the percentage by weight of the solvent based on the weight of the mixture of product and solvent, between 10% and 80%, forming a mixture.

Then the mixture is filtered using a filter aid, or is centrifuged, or is centrifuged and then filtered using a filter aid. At the end, the solvent is removed by distillation at a temperature between 100° C. and 230° C., preferably between 150° C. and 210° C., working at atmospheric pressure or at reduced pressure, more preferably at reduced pressure.

The present invention further relates to a process for preparing the detergent compositions comprising overbased metal compounds of calixarenes of general formula (I), described and claimed in the present patent application. Said process comprises reaction of acid compounds, or of partially salified, neutral, basic or overbased metal compounds, with an excess of the metal base, and the subsequent carbonation reaction of the unreacted metal base. Said process is carried out in the presence of a reaction solvent or of a mixture of reaction solvents and the following reactants:

a calixarene of formula (I), or a partially salified, neutral, basic or overbased metal compound of the calixarene of formula (I) as described and claimed in the present text, or mixtures thereof;
  optionally an organic acid compound, or a mixture thereof;
  a metal base;
  carbon dioxide.

During said process, a lubricant base oil or a mixture of lubricant base oils may be added. The base oils used are those already described above in the present text.

The metal base is preferably a basic compound of an alkaline-earth metal, or of an alkali metal.

For the purposes of the present invention, the alkali metals that may be used are selected from Li, Na, K, Rb and Cs; the alkaline-earth metals that may be used are selected from Be, Mg, Ca, Sr and Ba. A basic compound of an alkaline-earth metal selected from calcium and magnesium is more preferred, and even more preferably it is a basic compound of calcium.

The metal base is preferably an oxide or a hydroxide of an alkaline-earth metal or of an alkali metal, more preferably an oxide or a hydroxide of an alkaline-earth metal selected from calcium or magnesium; even more preferably it is calcium hydroxide.

The metal base may be added completely at the beginning of the overbasification reaction, or may be added partly at the beginning and partly at various intermediate time points of said reaction; preferably the metal base may be supplied in a single addition at the beginning of the reaction.

The amount of metal base used in the process for preparing the detergent compositions comprising overbased metal compounds of calixarenes of general formula (I) may correspond to a ratio that ranges between 1.1 and 15, preferably between 1.5 and 8, said ratio being calculated between the equivalents of the base and the sum of the equivalents of the calixarene of formula (I) and of the partially salified, neutral, basic, and overbased metal compounds, including the equivalents of the optional organic acid compound, or of the optional mixture of organic acid compounds.

During synthesis of the calixarenes of formula (I) described in the present patent application there may also be formation of linear oligomeric compounds of formula (IV) and monomers of formula (V), forming a mixture. This mixture may be used directly as a reactant in the process for preparing detergent compositions containing the overbased metal compounds of calixarenes of general formula (I). The compounds of formula (IV) and (V) are present in said mixtures at a concentration that is between 5% and 80%, preferably between 20% and 50%, said concentration being expressed as the total percentage by weight of said compounds (IV) and (V) relative to the mixture.

The calixarenes of general formula (I) may moreover be obtained in a mixture with one or more solvents: said mixture may also be used directly as a reactant in the process for preparing detergent compositions containing the overbased metal compounds of calixarenes of general formula (I). Useful solvents are those selected from: aromatic or aliphatic hydrocarbons, preferably toluene and xylene; aliphatic or aromatic ethers with a number of carbon atoms between 4 and 20; aliphatic or aromatic ketones with a number of carbon atoms between 4 and 20; esters of carboxylic acids with a number of carbon atoms between 4 and 20; or alcohols with a number of carbon atoms between 4 and 20.

The preferred solvents are toluene and xylene.

The partially salified metal compound of the calixarene of formula (I), used in the process for preparing detergent compositions containing the overbased metal compounds of calixarenes of general formula (I), is characterized by a metal content corresponding to a ratio between the equivalents of metal and the equivalents of calixarene between 0.15 and 0.99, preferably between 0.5 and 0.9. Preferably in said metal compound the acid functions of carboxylic type are fully salified, whereas incomplete salification depends on the phenolic hydroxyl functionalities present.

The metal of said metal compound is preferably selected from the alkali metals and the alkaline-earth metals. The preferred metals are the alkaline-earth metals; calcium and magnesium are particularly preferred, and calcium is even more preferred.

The partially salified metal compound of the calixarene of formula (I), used in the process for preparing detergent compositions containing the overbased metal compounds of calixarenes of general formula (I), may be present mixed with further metal compounds of compounds of formula (IV) and (V); preferably partially salified calcium or magnesium compounds at a concentration between 1% and 70%, preferably between 4% and 50%, expressed as the total percentage by weight of said metal compounds of compounds (IV) and (V) based on the mixture consisting of the partially salified metal compound of calixarenes of formula (I) and the metal compounds of compounds (IV) and (V).

The partially salified metal compound of the calixarene of formula (I), used in the process for preparing detergent compositions containing the overbased metal compounds of calixarenes of general formula (I), may be mixed with a lubricant base oil; in particular, those base oils already described in the present text are preferred.

In the mixture, the base oil may be present at a concentration between 10% and 90%, preferably between 20% and 70%, expressed as the percentage by weight of the base oil based on the mixture.

In the neutral metal compound of the calixarene of formula (I), used in the process for preparing detergent compositions containing the overbased metal compounds of calixarenes of general formula (I), the metal is preferably selected from the alkali metals and the alkaline-earth metals. The preferred metals are the alkaline-earth metals; calcium and magnesium are particularly preferred, and calcium is even more preferred.

The metal content corresponds to a ratio between the equivalents of metal and those of the calixarene equal to 1.

The neutral metal compound of calixarene of formula (I) is fully salified and is therefore derived from a calixarene of formula (I) in which hydroxyl substituents are not present and in which preferably each unit of the calixarene ring contains at least one acid functionality of carboxylic type.

Optionally the neutral metal compound of the calixarene of formula (I) may be mixed with neutral metal compounds, preferably of calcium or magnesium, of compounds of formula (IV) and (V) at a concentration between 1% and 70%, preferably between 4% and 50%, expressed as the total percentage by weight of said metal compounds of compounds (IV) and (V) relative to the mixture containing the neutral metal compounds of calixarenes of formula (I) and the metal compounds of compounds (IV) and (V).

Optionally the neutral metal compound of calixarene of formula (I) may be mixed with a lubricant base oil, in particular those oils described in the present text are preferred, at a concentration between 10% and 90%, preferably between 20% and 70%, expressed as the percentage by weight of the base oil based on the mixture.

In the basic metal compound of the calixarene of formula (I), used in the process for preparing detergent compositions containing the overbased metal compounds of calixarenes of general formula (I), the metal is preferably selected from the alkali metals and the alkaline-earth metals. The preferred metals are the alkaline-earth metals; calcium and magnesium are particularly preferred, and calcium is even more preferred.

The basic metal compound of the calixarene of formula (I), used in the process for preparing detergent compositions containing the overbased metal compounds of calixarenes of general formula (I), is characterized by a metal content corresponding to a ratio between the equivalents of metal and those of the calixarene between 1.01 and 4, preferably between 1.1 and 2.

In the basic metal compound of the calixarene of formula (I), used in the process for preparing detergent compositions containing the overbased metal compounds of calixarenes of general formula (I), the excess of metal relative to the calixarene is in the form of metal hydroxide, preferably calcium or magnesium hydroxide.

The basic metal compound of the calixarene of formula (I), used in the process for preparing detergent compositions containing the overbased metal compounds of calixarenes of general formula (I), may also be mixed with basic metal compounds, preferably of calcium or magnesium, of compounds of formula (IV) and (V) at a concentration between 1% and 70%, preferably between 4% and 50%, expressed as the percentage by weight of said basic metal compounds of compounds (IV) and (V) relative to the mixture containing the basic metal compounds of calixarenes of formula (I) and the basic metal compounds of compounds (IV) and (V).

The basic metal compound of the calixarene of formula (I) may be mixed with a lubricant base oil, in particular those described in the present text, at a concentration between 10% and 90%, preferably between 20% and 70%, expressed as the percentage by weight of the base oil based on the mixture.

In the overbased metal compounds of the calixarene of formula (I) the metal is preferably selected from the alkali metals and the alkaline-earth metals. The preferred metals are the alkaline-earth metals; calcium and magnesium are particularly preferred, and calcium is even more preferred.

The overbased metal compound of the calixarene of formula (I) is characterized by a metal content corresponding to a ratio between the equivalents of metal and those of the calixarene between 1.1 and 8, preferably between 1.5 and 4.

In the overbased metal compound of the calixarene of formula (I) the excess of metal relative to the calixarene is mainly in the form of metal carbonate, preferably calcium carbonate or magnesium carbonate.

The purpose of using an overbased metal compound of the calixarene of formula (I) in the process for preparing detergent compositions containing overbased metal compounds of calixarenes of formula (I) is to increase the content of colloidal metal carbonate, preferably of calcium carbonate or magnesium carbonate, and hence the TBN value of the initial overbased metal compound of the calixarene of formula (I).

The overbased metal compound of the calixarene of formula (I) may be mixed with overbased metal compounds, preferably of calcium or magnesium, of compounds of formula (IV) and (V) at a concentration between 1% and 70%, preferably between 4% and 50%, expressed as the total percentage by weight of said overbased metal compounds of compounds (IV) and (V) relative to the mixture.

The overbased metal compound of the calixarene of formula (I) may be mixed with a lubricant base oil, in particular those described in the present text, at a concentration between 10% and 90%, preferably between 20% and 70%, expressed as the percentage by weight of the base oil based on the mixture.

During the process for preparing overbased metal compounds of calixarenes of formula (I), described and claimed in the present text, the same organic acid compounds already described previously in the text may be added. Said organic acids may also be mixed with the same solvents, or mixtures of solvents, already described previously in the text.

The organic acid compound or the mixture of organic acid compounds, when used in said process, is introduced in an amount between 5% and 90%, preferably between 20% and 70%, expressed as the percentage by weight of the organic acid, excluding the solvent, relative to the mixture of reactants, excluding the solvents and excluding the metal base.

The reaction solvent or the mixture of reaction solvents used in the process for preparing overbased metal compounds of calixarenes of formula (I) is that already described previously in the text; preferably, a mixture of solvents is used.

Said mixture of reaction solvents may consist of one or more reaction solvents capable of dissolving the calixarenes of formula (I), the metal compounds of calixarenes of formula (I) and, if present, the organic acid compounds or the mixtures of organic acid compounds, and of one or more polar reaction solvents capable of dissolving the metal base and carbon dioxide, at least partially. The reaction solvent or mixture of reaction solvents capable of dissolving the calixarenes of formula (I), the metal compounds of calixarenes of formula (I) and the organic acid compounds or mixture of organic acid compounds is preferably selected from toluene, heptane, 2-ethylhexyl alcohol, cyclohexanone and butyl acetate. The solvent or mixture of solvents capable of dissolving the metal base and carbon dioxide at least partially is preferably selected from ethylene glycol, methanol, glycerol, diethylene glycol monomethyl ether.

The preferred mixtures of reaction solvents are ethylene glycol with 2-ethylhexanol, glycerol with 2-ethylhexanol and methanol with toluene.

The reaction solvent or mixture of reaction solvents is added in an amount corresponding to a percentage by weight between 10% and 90%, preferably between 30% and 70%, calculated relative to all of the components of the reaction mixture.

Preferably the reaction solvent is a mixture of ethylene glycol with 2-ethylhexyl alcohol, containing an amount of ethylene glycol, expressed as the percentage by weight of ethylene glycol relative to the mixture of the two solvents, between 3% and 60%, preferably between 8% and 40%. The ethylene glycol may be added completely, together with 2-ethylhexyl alcohol, at the beginning of the reaction with the excess of metal base, or may be fractionated, adding it separately from the 2-ethylhexyl alcohol partly at the beginning and partly during the reaction with the excess of metal base and partly before the subsequent carbonation reaction with carbon dioxide. The ethylene glycol is preferably added partly during the reaction with the excess of metal base and partly before the subsequent carbonation reaction.

During the process for preparing overbased metal compounds of calixarenes of formula (I), described and claimed in the present text, the same lubricant base oils, or mixtures thereof, already described previously in the text may be added. The lubricant base oil is used at a concentration, expressed as the percentage by weight of the base oil relative to the whole reaction mixture, between 5% and 70%, preferably between 10% and 40%.

During the process for preparing overbased metal compounds of calixarenes of formula (I), described and claimed in the present text, carbon dioxide may be added after each addition of the metal base, or may be added subsequently to addition of all of the metal base in two or more successive steps. Preferably the carbon dioxide is added in a single step, following a single addition of all of the metal base. The carbon dioxide may be added as gas or as solid, preferably as gas.

The amount of carbon dioxide used corresponds to a ratio between the equivalents of carbon dioxide and those of the metal base in excess with respect to the equivalents of the compounds to be neutralized, between 0.6 and 4, preferably between 0.8 and 3. In a more preferred embodiment of the invention the carbon dioxide is used in an amount such as to obtain a percentage carbonation of the available calcium hydroxide between 60% and 99%, more preferably between 80% and 95%, so as to obtain stable products, with high efficiency of incorporation of calcium.

During the process for preparing detergent compositions of overbased metal compounds of calixarenes of formula (I), promoters or catalysts of the carbonation reaction may also be used, preferably selected from the inorganic halides, such as calcium chloride; the metal carboxylates, such as calcium acetate; and the organic halides, such as octyl chloride. If used, this catalyst is preferably added in the initial step of the process of preparation described and claimed in an amount, expressed as the percentage by weight of the catalyst relative to the weight of the whole reaction mixture, between 0.1% and 3%, preferably between 0.5% and 1.5%.

The process for preparing the detergent compositions comprising overbased metal compounds of calixarenes of formula (I) may be carried out by adding the individual reactants, the reaction solvents and the optional lubricant base oils in any order, with the proviso that the carbon dioxide is added subsequently to the metal base. The metal base and the carbon dioxide may be added in a single addition or using fractional additions, preferably with a single addition.

The process for preparing detergent compositions comprising overbased metal compounds of calixarenes of formula (I) may further comprise a step of maturation of the mixture obtained, after the carbonation reaction with carbon dioxide, which consists of keeping the mixture stirred for a certain period of time at a certain temperature.

In a further preferred embodiment, the process for preparing detergent compositions containing overbased metal compounds of calixarenes of general formula (I) comprises the following steps:

mixing a calixarene of formula (I), or a partially salified, neutral, basic or overbased metal compound of the calixarene of formula (I), or a mixture thereof, and optionally an organic acid compound or a mixture of organic acid compounds, with a lubricant base oil, or a mixture thereof, thus forming a mixture of reactants;

optionally removing the solvent optionally present in the mixture of reactants by distillation;

adding, to said mixture of reactants, a metal base in excess and a part of the reaction solvent, or a part of a mixture of reaction solvents, preferably 2-ethylhexyl alcohol, and removing, by distillation, the water of reaction formed, thus forming a second mixture;

optionally adding an organic acid compound, or a mixture of organic acid compounds and removing, by distillation, the water of reaction formed, forming a third mixture;

then adding, to said second mixture or third mixture, a further part of reaction solvent, or a further part of a mixture of reaction solvents and removing, by distillation, the water of reaction formed, thus forming a fourth mixture;

adding, to said fourth mixture, a further part of reaction solvent, or a further part of a mixture of reaction solvents; thus forming a fifth mixture;

then proceeding with the carbonation reaction between said fourth mixture or fifth mixture and carbon dioxide.

Preferably the composition thus obtained also undergoes a maturation step. The carbonation and optional maturation are followed by the next step of recovery of the product, removing the solvents by distillation and continuing with filtration or centrifugation of the product.

In a further preferred embodiment, the process for preparing detergent compositions containing overbased metal compounds of calixarenes of formula (I) comprises the following steps:

mixing a calixarene of formula (I), or a partially salified, neutral, basic or overbased metal compound of the calixarene of formula (I) or a mixture thereof and optionally an organic acid compound or a mixture of organic acid compounds with a lubricant base oil, or a mixture of lubricant base oils, thus forming a mixture of reactants;

optionally removing the solvent optionally present in the mixture of reactants by distillation;

subsequently adding to said mixture of reactants a metal base in excess relative to the reactants and a part of the reaction solvent, or a part of a mixture of reaction solvents, preferably 2-ethylhexyl alcohol, and preferably distilling to remove the water of reaction formed, forming a second mixture;

subsequently adding, to said second mixture, a further part of reaction solvent, or a further part of a mixture of reaction solvents, preferably a first portion of ethylene glycol, and removing, by distillation, the water of reaction formed, forming a third mixture;

adding, to said third mixture, a further part of reaction solvent, or a further part of a mixture of reaction solvents, preferably a second portion of ethylene glycol, forming a fourth mixture;

then proceeding with the carbonation reaction between said fourth mixture and carbon dioxide.

Preferably the composition thus obtained also undergoes a step of maturation of the reaction mixture. Carbonation and optional maturation are followed by the next step of recovery of the product, removing the solvents by distillation and continuing with filtration or centrifugation of the product.

The temperature at which the reaction step is carried out, in which an excess of metal base is added, is between 30° C. and 200° C., preferably between 40° C. and 160° C. Selection of the optimum temperature depends on the nature of the solvent used. The pressure at which the reaction between the mixture of reactants and the excess of metal base is carried out is between 0.01 bar and 1.5 bar, preferably between 0.04 bar and 1.2 bar. The carbonation reaction with carbon dioxide is carried out at a temperature between 15° C. and 180° C., preferably between 20° C. and 150° C. Addition of carbon dioxide as gas is carried out for a time between 10 minutes and 6 hours, preferably between 1 hour and 4 hours. The absolute pressure at which the carbonation reaction is carried out is between 1 bar and 5 bar, preferably between 1 bar and 2 bar.

More preferably the step of reaction with an excess of metal base is carried out at a temperature between 30° C. and 200° C., at a pressure between 0.01 bar and 1.5 bar, and the step of the carbonation reaction with carbon dioxide is carried out at a temperature between 15° C. and 180° C. and at a pressure between 1 bar and 5 bar by feeding carbon dioxide as a gas for a time between 10 minutes and 6 hours.

At the end of carbonation, the process may be continued with maturation of the reaction mixture, which is an optional operation, and it may be carried out at a temperature between 40° C. and 160° C., for a time between 10 minutes and 3 hours, preferably between 20 minutes and 2 hours.

The product is preferably obtained as a solution in lubricant base oil, separating the water of carbonation and the solvent by distillation.

Distillation of the solvents is carried out by increasing the temperature to a maximum value of 230° C., preferably up to 210° C. and keeping the product at this temperature for the time required for complete removal of the solvents. Distillation of the solvents may be carried out at atmospheric pressure, or at reduced pressure, preferably at reduced pressure.

At the end, the product is filtered using a filter aid, or alternatively it may be centrifuged.

As an alternative, a solvent may be added to the product, preferably 2-ethylhexanol or heptane or xylene or toluene, in an amount, expressed as the percentage by weight of the solvent based on the weight of the mixture of product and solvent, between 10% and 80%. Then the mixture is filtered using a filter aid, or centrifuged, or centrifuged and then filtered using a filter aid. At the end, the solvent is removed by distillation at a temperature between 100° C. and 230° C., preferably between 150° C. and 210° C., working at atmospheric pressure or at reduced pressure, more preferably at reduced pressure.

The present invention also relates to lubricant compositions containing the detergent compositions described and claimed in the present text, a lubricant base oil, or a mixture of lubricant base oils. These lubricant compositions are also called lubricant formulations or engine lubricant formulations. The detergent compositions described and claimed in the present text are additives that are able to guarantee excellent control of the formation of deposits and effective neutralization of the inorganic and organic acidity that is generated in the lubricant, thus permitting control of the phenomena of wear and corrosion.

The lubricant formulations may contain, besides the detergent compositions according to the invention, other detergent additives, for example neutral and overbased calcium and magnesium alkylbenzene sulfonates, viscosity index improvers, dispersants, antioxidants, friction modifiers, antiwear additives and extreme pressure additives (EP additives), corrosion inhibitors, pour point depressants, foam inhibitors, emulsifiers and others.

For the purposes of the present invention, lubricant formulations are to be understood as both finished lubricant formulations and compositions of lubricant additives, commonly called additive packages.

For the purposes of the present invention the additive packages are concentrated mixtures of additives that comprise the detergent compositions described and claimed in the present text, one or more of the other additives stated above and a lubricant base oil or a mixture of lubricant base oils. The finished lubricant formulations comprise a lubricant base oil or a mixture of lubricant base oils, and may comprise one or more of said additive packages and one or more of the individual additives stated above.

The lubricant compositions according to the present invention contain one or more detergent compositions described and claimed in the text, at a total concentration, expressed as the percentage by weight of said detergent compositions relative to the lubricant composition, between 0.1% and 90%, preferably between 0.5% and 30%, even more preferably between 1% and 20%.

For better understanding of the present invention, some illustrative, non-limiting examples are given below.

Examples 1-9: Synthesis of the Calixarenes of Formula (I)

Examples 1 to 9 relate to the synthesis of the calixarenes of formula (I) described in the present text, which will be used in the preparation of the metal compounds of calixarenes of formula (I) described and claimed in the present text.

Example 1: Synthesis of p-dodecyl calix[5,6,8]arene Mixed with Linear Oligomers (77.5 wt % in Xylene), the Compound that Will be Used for Preparing the Calixarenes of Formula (I) of Examples 3 and 5 and the Detergent Compositions of Comparative Examples 12, 27 and 30

A 3-L reactor equipped with a stirrer, a thermometer and a condenser is charged, in an inert atmosphere, with 364.7 g (1.39 mol) of p-dodecylphenol, 139.9 g (1.723 mol) of 37% formaldehyde and 6.46 mL (0.065 mol) of 10 M NaOH aqueous solution. The mixture is stirred and heated in an inert atmosphere to a temperature of 120° C. The water formed is collected in a condenser of the "Dean and Stark" type. After 2 hours, 1.6 L of xylene is added and the mixture is refluxed in an inert atmosphere for 4 hours. Then the product is washed with 500 ml of distilled water and concentrated to 77.5 wt % in xylene by distillation of the excess solvent. 400 g (quantitative yield) of product is recovered as a dark-coloured solution. The relative abundance of the calixarene structures is determined by $^1$H NMR, $^{13}$C NMR and ESI mass spectrometry analyses on the product after removal of all of the solvent. The concentration by weight relative to the active part alone is about 60%. The remaining 40% is due to linear oligophenolic chains. The aforementioned analyses further show that the product with calixarene structure is a mixture of cyclic products with 5, 6 and 8 units.

Example 2: Synthesis of p-dodecyl calix[5,6,8]arene Mixed with Linear Oligomers, the Compound that Will be Used for Preparing the Calixarene of Formula (I) of Examples 4 and 6 and the Detergent Composition of Comparative Example 17

The method of preparation used is the same as in example 1, and so too are the reactants and their relative amounts. At the end of the reaction it is washed with 500 ml of water, the solvent is removed completely by distillation and 310 g (quantitative yield) of product is recovered in the form of a yellow solid. The relative abundance of the calixarene structures is determined by $^1$H NMR, $^{13}$C NMR and ESI mass spectrometry analyses. The concentration by weight is about 60%. The remaining 40% is due to linear oligophenolic chains. The aforementioned analyses further show that the product with calixarene structure is a mixture of cyclic products with 5, 6 and 8 units.

Example 3: Synthesis of p-dodecyl calix[5,6,8]arene Mixed with Linear Oligomers, Fully Functionalized with Hydroxycarbonyl-Methoxy Groups (53 wt % in Xylene); it is a Calixarene of Formula (I), which Will be Used for Preparing the Detergent Compositions of the Invention of Examples 10, 24, 28, 31 and 32

A 2.5-L reactor equipped with a stirrer, a thermometer and a condenser is charged, in an inert atmosphere, with 232.7 g of p-dodecyl calix[5,6,8]arene+linears at 77.5 wt % in xylene of example 1 (MW=281.1 per repeating unit, 0.641 mol), 320.2 g of xylene and 44.5 g (0.674 mol) of 85% KOH. The mixture is stirred and heated to boiling in an inert atmosphere. The water formed is collected in a condenser of the "Dean and Stark" type. After cooling to 70° C., 191.3 g (1.123 mol) of bromoethyl acetate is added in the space of 30 minutes. The mixture is heated at 130° C. for 12 hours. After cooling to 50° C., 19 g of PEG 400, 330 g of distilled water and 158.8 g (2.406 mol) of 85 wt % KOH are added. The reaction mixture is refluxed with stirring for 13 hours. After cooling to 40° C., 264.1 g (2.68 mol) of 37% HCl is added in the space of 15 minutes. The mixture is stirred for 30 minutes at a temperature of 50° C. After switching off the stirrer, the aqueous phase is separated. The organic phase is washed, at a temperature of about 50° C., with two 150-mL aliquots of 0.5 M HCl aqueous solution. Once the organic phase has been separated, the excess solvent is removed by distillation at reduced pressure (50 mbar at 100° C.), to obtain 390 g (MW=339.1, 95% yield) of hydroxycarbonyl-methyl p-dodecylcalix[5,6,8]arene mixed with linear oligomers, fully functionalized, at 53% in xylene, in the form of brown liquid. The purity and the degree of functionalization of the product are checked, after removing the solvent, by $^1$H NMR, $^{13}$C NMR and ESI mass spectrometry analyses, showing total functionalization of the starting mixture of calixarenes.

Example 4: Synthesis of p-dodecyl calix[5,6,8]arene Mixed with Linear Oligomers Fully Functionalized with Hydroxycarbonyl-Methoxy Groups; it is a Calixarene of Formula (I), which Will be Used for Preparing the Detergent Compositions of the Invention of Examples 14, 20 and 21

A 1-L reactor equipped with a stirrer, a thermometer and a condenser is charged, in an inert atmosphere, with 69.7 g (MW=281.1 per repeating unit, 0.248 mol) of p-dodecyl calix[5,6,8]arene mixed with linear oligomers from example 2, 250 g of xylene, 47.9 g (0.347 mol) of $K_2CO_3$ and 51.8 g (0.31 mol) of bromoethyl acetate. The mixture is stirred and heated in an inert atmosphere to 140° C. and is stirred for 12 hours. After cooling to 50° C., 7.3 g of PEG 400, 125 g of distilled water and 57.9 g of 85 wt % KOH (0.878 mol) are added. The mixture is heated at 100° C. for 12 hours. After cooling to 40° C., 177.1 g (1.47 mol) of 37% HCl is added in the space of 15 minutes. The mixture is stirred for 30 minutes at a temperature of 50° C. After switching off the stirrer, the aqueous phase is separated. The organic phase is washed, at a temperature of about 50° C., with two 100-mL aliquots of 0.5 M HCl aqueous solution. Once the organic phase has been separated, all the solvent is removed by distillation at reduced pressure (50 mbar at 100° C.), to obtain 80 g (MW=339.1 per repeating unit, yield=95%) of hydroxycarbonyl-methyl p-dodecylcalix[5,6,8]arene mixed with linear oligomers, fully functionalized, in the form of an amber-coloured solid. The purity and the degree of functionalization of the product are checked by $^1$H NMR, $^{13}$C NMR and ESI mass spectrometry analyses, showing total functionalization.

Example 5: Synthesis of p-dodecyl calix[5,6,8]arene+Linear Oligomers 33% Functionalized with Hydroxycarbonyl-Methoxy Groups (53.5 wt % in Xylene); it is a Calixarene of Formula (I), which Will be Used for Preparing the Detergent Compositions of the Invention of Examples 11, 26 and 29

A 2-L reactor equipped with a stirrer, a thermometer and a condenser is charged, in an inert atmosphere, with 227.8 g of the p-dodecyl calix[5,6,8]arene+linear oligomers at 77.5 wt % in xylene of example 1 (MW=281.1 per repeating unit, 0.628 mol), 320 g of xylene, 78.1 g (0.565 mol) of $K_2CO_3$ and 36.7 g (0.220 mol) of bromoethyl acetate. The mixture is stirred and heated in an inert atmosphere to 140° C. and is stirred for 12 hours. After cooling to 50° C., 8.3 g of PEG 400, 275 g of distilled water and 63.7 g (0.965 mol) of 85% KOH are added. The mixture is heated at 100° C. for 12 hours. After cooling to 40° C., 160.6 g (1.63 mol) of 37% HCl is added in the space of 15 minutes. The mixture is stirred for 30 minutes at a temperature of 50° C. After switching off the stirrer, the aqueous phase is separated. The organic phase is washed, at a temperature of about 50° C., with two 150-mL aliquots of 0.5 M HCl aqueous solution.

Once the organic phase has been separated, the excess solvent is removed by distillation at reduced pressure (50 mbar at 100° C.), to obtain 334.8 g (MW=300.2 per repeating unit, yield=95%) of hydroxycarbonyl-methyl p-dodecyl-calix[5,6,8]arene mixed with linear oligomers at 53.5% in xylene with degree of functionalization equal to 33%, in the form of brown oil. The purity and the degree of functionalization of the product are checked by $^1$H NMR, $^{13}$C NMR and ESI mass spectrometry analyses, showing the functionalization stated above.

Example 6: Synthesis of p-dodecyl calix[5,6,8]arene Mixed with Linear Oligomers Fully Functionalized with 4 (hydroxycarbonyl)-benzyloxy Groups (52.5 wt % in Xylene); it is a Calixarene of Formula (I), which Will be Used for Preparing the Detergent Composition of the Invention of Example 25

A 1-L reactor equipped with a stirrer, a thermometer and a condenser is charged, in an inert atmosphere, with 60.6 g of p-dodecyl calix[5,6,8]arene+linear oligomers of example 2 (MW=281.1 per repeating unit, 0.216 mol), 250 g of xylene, 41.7 g (0.302 mol) of $K_2CO_3$ and 65.7 g (98%, 0.281 mol) of 4-(bromomethyl)methyl benzoate. The mixture is stirred, heated in an inert atmosphere to 140° C. and is stirred for 48 hours. After cooling to 50° C., 1.8 g of PEG 400, 150 g of distilled water and 49.9 g (0.756 mol) of 85% KOH are added. The mixture is heated at 100° C. for 12 hours. After cooling to 40° C., 123.9 g (1.258 mol) of 37% HCl is added in the space of 15 minutes. The mixture is stirred for 30 minutes at a temperature of 50° C. After switching off the stirrer, the aqueous phase is separated. The organic phase is washed, at a temperature of about 50° C., with two 100-mL aliquots of 0.5 M HCl aqueous solution. Once the organic phase has been separated, the excess solvent is removed by distillation at reduced pressure (50 mbar at 100° C.), to obtain 167.8 g (MW=429.2 per repeating unit, yield=95%) of hydroxycarbonyl-benzyloxy p-do-decylcalix[5,6,8]arene+linear oligomers, fully functionalized, at 52.5 wt % in xylene, in the form of brown oil. The purity and the degree of functionalization of the product are checked by $^1$H NMR, $^{13}$C NMR and ESI mass spectrometry analyses, showing total functionalization of the starting mixture of calixarenes.

Example 7: Synthesis of p-tert-octyl calix[6,8]arene, the Compound Used for Preparing the Calixarenes of Formula (I) of Examples 8 and 9 and the Detergent Compositions of Comparative Examples 16 and 23

A 2.5-L reactor equipped with a stirrer, a thermometer and a condenser is charged, in an inert atmosphere, with 194.9 g (0.916 mol) of p-tert-octyl-phenol, 105.6 g (1.30 mol) of 37% formaldehyde and 5.9 mL (0.059 mol) of 10 M NaOH aqueous solution. The mixture is stirred and heated in an inert atmosphere to a temperature of 120° C. The water formed is collected in a condenser of the "Dean and Stark" type. After 2 hours, 700 mL of xylene is added, and the mixture is heated to boiling in an inert atmosphere for 4 hours. During this time, removal, as an azeotrope with xylene, of the water of reaction is continued, it being collected in the "Dean Stark" condenser. After partial distillation of the solvent (about 350 mL), 1.0 L of 2-propanol is added. A yellow solid forms, which is filtered and washed successively with 550 mL of water, 550 ml of 2-propanol and 550 ml of xylene. After drying, 100.2 g (MW=218.3 per repeating unit, 0.459 mol, yield=50.1%) of p-tert-octyl calix[6,8]arene is obtained as a white powdery solid. The purity of the product is checked by $^1$H NMR, $^{13}$C NMR and ESI mass spectrometry analyses, showing only the presence of p-tert-octyl calix[6,8]arene. The relative abundance of the calixarene structures is determined by column chromatography, showing a hexa-p-octylcalix[6]arene:octa-p-octyl-calix[8]arene ratio equal to 2:3.

Example 8: Synthesis of p-tert-octyl calix[6,8]arene Fully Functionalized with Hydroxycarbonyl-Methoxy Groups; it is a Calixarene of Formula (I), which Will be Used for Preparing the Detergent Compositions of the Invention of Examples 13, 18, 19

A 500-mL reactor equipped with a stirrer, a thermometer and a condenser is charged, in an inert atmosphere, with 41.3 g (MW=218.3 per repeating unit, 0.189 mol) of p-tert-octyl calix[6,8]arene of example 7, 60 g of xylene and 13.1 g (0.199 mol) of 85% KOH. The mixture is stirred and heated to boiling in an inert atmosphere. The water formed is collected in a condenser of the "Dean and Stark" type. After cooling to 70° C., 45.2 g (0.265 mol) of bromoethyl acetate is added in the space of 30 minutes. The mixture is heated at 100° C. for 12 hours. After cooling to 50° C., 3.4 g of PEG 400, 70 g of distilled water and 33.7 g (0.511 mol) of 85% KOH are added. The reaction mixture is refluxed with stirring for 13 hours. After cooling to 40° C., 53.9 g (0.547 mol) of 37% HCl is added in the space of 15 minutes. The mixture is stirred for 30 minutes at a temperature of 50° C. After switching off the stirrer, the aqueous phase is separated. The organic phase is washed, at a temperature of about 50° C., with two 50-mL aliquots of 0.5 M HCl aqueous solution. Once the organic phase has been separated, all the solvent is removed by distillation at reduced pressure (50 mbar at 100° C.) and 49.6 g (MW=276.4 per repeating unit, 0.180 mol, yield=95%) of fully functionalized hydroxycarbonyl-methoxy p-tert-octyl calix[6,8]arene is obtained in the form of a brown solid. The purity and the degree of functionalization of the product are checked by $^1$H NMR, $^{13}$C NMR and ESI mass spectrometry analyses, showing total functionalization.

Example 9: Synthesis of p-tert-octyl calix[6,8]arene 50% Functionalized with Hydroxycarbonylmethoxy Groups; it is a Calixarene of Formula (I), which Will be Used for Preparing the Detergent Compositions of the Invention of Examples 15 and 22

A 250-mL reactor equipped with a stirrer, a thermometer and a condenser is charged, in an inert atmosphere, with 24.8 g (MW=218.3 per repeating unit, 0.114 mol) of p-tert-octylcalix[6,8]arene of example 7, 50 g of xylene and 3.9 g (0.06 mol) of 85% KOH. The mixture is stirred and heated to boiling in an inert atmosphere. The water formed is collected in a condenser of the "Dean and Stark" type. After cooling to 70° C., 10 g (0.06 mol) of bromoethyl acetate is added in the space of 30 minutes. The mixture is heated at 100° C. for 12 hours. After cooling to 50° C., 2.0 g of PEG 400, 50 g of distilled water and 3.8 g (0.068 mol) of 85% KOH are added. The reaction mixture is refluxed with stirring for 13 hours. After cooling to 40° C., 7.0 g (0.072 mol) of 37% HCl is added in the space of 5 minutes. The mixture is stirred for 30 minutes at a temperature of 50° C. After switching off the stirrer, the aqueous phase is separated. The organic phase is washed, at a temperature of about 50° C., with two 50-mL aliquots of 0.5 M HCl aqueous solution. Once the organic phase has been separated, all the solvent is removed by distillation at reduced pressure (50 mbar at 100° C.), to obtain 26.8 g (MW=247.4 per repeating unit, 0.108 mol, yield=95%) of hydroxycarbonyl-methoxy p-tert-octylcalix[6,8]arene with degree of functionalization equal to 50%, in the form of a brown solid. The purity and the degree of functionalization of the product are checked by $^1$H NMR, $^{13}$C NMR and ESI mass spectrometry analyses, showing the functionalization of the starting calixarene stated above.

Examples 10-32: Preparation of Detergent Compositions Comprising Calcium Compounds of Calixarenes The examples given hereunder relate to the preparation of detergent compositions comprising calcium compounds of calixarenes of formula (I) as described and claimed in the text, in which the parameter TBN (total base number), expressed in mg KOH/g, was determined as described in method ASTM D 2896. The free alkalinity of the detergent composition, expressed in mg KOH/g, was determined as described in method ISO 4314. The contribution to the free alkalinity of the detergent composition is mainly due to the free calcium hydroxide.

The turbidity, expressed in nephelometric turbidity units (NTU), was determined with the HACH 2100 AN turbidimeter on the solution of the detergent composition at 5 wt % in SN 150 base oil.

The calcium content was determined by inductively coupled plasma atomic emission spectrometry (ICP-AES), as described in method ASTM D 4951, while the viscosity at 100° C. was determined by method ASTM D 445.

Examples 10-12: Preparation of Detergent Compositions Comprising Partially Neutralized and Neutral Calcium Compounds of Calixarenes Examples 10 to 12 relate to the preparation of the detergent compositions according to the invention, comprising calcium compounds, partially neutralized and neutral, derived from the calixarenes whose synthesis is given in examples 1-9.

The preparation reactions are carried out in an RC-1 Mettler calorimeter consisting of a jacketed 5-necked glass reactor with a capacity of 0.5 litre, thermostatically controlled by circulation, in the jacket, of a fluid obtained from a thermostatic bath inside the instrument. The reactor is equipped with: mechanical paddle stirrer; Dean-Stark condenser cooled with mains water, connected to a vacuum line and to a nitrogen line and equipped with a flask for collecting the distillate; bottom discharge equipped with a teflon cock; thermocouple for temperature measurement. The system is controlled by a computer, which allows the desired heating and cooling programmes to be set.

Example 10

The reactor described above is charged in a nitrogen atmosphere: 174.73 grams of p-dodecyl calix[5,6,8]arene mixed with linear oligomers fully functionalized with hydroxycarbonyl-methoxy groups from example 3 (MW=339.1 per repeating unit, 53 wt % in xylene, 0.273 mol) and 91.58 grams of SN 150 base oil.

The mixture is heated with stirring (500 rev/min) to give a temperature of 130° C. inside the reactor. Then the xylene is removed by flash distillation, cutting off the nitrogen and gradually lowering the pressure to about 20 mbar. 82.1 g of xylene is collected. The vacuum is broken, the nitrogen atmosphere is restored and 10.13 g of calcium hydroxide (0.1365 mol) and 25.02 grams of ethylene glycol are added via a charging funnel at a temperature of 130° C., in the space of about 5 minutes. While stirring, 153.40 grams of 2-ethylhexanol is then added from the same charging funnel.

The nitrogen is cut off and vacuum is applied, gradually lowering the pressure to 70 mbar. It is left in these conditions for 3 hours, during which the 2-ethylhexanol-water azeotrope is distilled and is collected in the Dean-Stark condenser, where the water, which also contains small amounts of ethylene glycol, is separated from the 2-ethylhexanol.

Maintaining the pressure at 70 mbar, the mixture is heated from 130° C. to 200° C. by programming the temperature increase of the thermostatic bath from 140° C. to 210° C. in 70 minutes (1° C. per minute). During this step the solvent is removed by flash distillation and is collected in a flask connected to the Dean-Stark condenser.

Once a temperature of 200° C. is reached, the pressure is further reduced to below 10 mbar and these conditions are maintained for 60 minutes to remove the greater part of the residual solvent from the product. Then the reaction mixture is cooled to 160° C., the vacuum is broken and the nitrogen atmosphere is restored.

An amount of filter aid equal to 6 g is added to the stirred mixture at a temperature of 160° C., and after mixing for 15 minutes it is filtered on a 0.4-litre jacketed steel filter, having a filtering surface consisting of an 80-mesh steel screen. Prior to filtration, a layer of filtering earth is prepared on the filter. Filtration is carried out at a temperature of 160° C. and with a pressure of 5 atmospheres of nitrogen. A high filtration rate was obtained.

The total amount of product, including that recovered after washing the filter with solvent, is 190 grams.

The product after filtration has the following characteristics:
Calcium content: 2.88 wt %
Viscosity at 100° C.: 890.3 cSt
TBN: 81 mg KOH/g
Free alkalinity: 0 mg KOH/g
Turbidity (5% solution in SN 150): 5.0 NTU (nephelometric turbidity units)

Based on the results obtained and taking into account that the free alkalinity corresponds to the content of free calcium hydroxide, the following parameters can be calculated:
Efficiency of calcium incorporation=100%
Neutralization yield=100%

It is also possible to calculate the content of salified calixarene units present as calcium salts (soap):
TBN soap=81.0 mg KOH/g
Soap content=51.5 wt %

Example 11

The method of preparation used is the same as in example 10, except that in this case p-dodecyl calix[5,6,8]arene mixed with linear oligomers 33% functionalized with hydroxycarbonyl-methoxy groups from example 5 was used. The amounts of reactants and of solvents used are as follows:
Product example 5 (MW=300.2 per repeating unit, 53.5 wt % in xylene, 0.282 mol): 158.28 grams,
SN 150 base oil: 84.35 grams,
Calcium hydroxide (0.141 mol): 10.46 grams,
Ethylene glycol: 22.87 grams,
2-Ethylhexanol: 141.31 grams.

During the preparation procedure the amount of xylene removed by flash distillation is 73.5 grams.

A high filtration rate was obtained.

The total amount of product, including that recovered after washing the filter with solvent, is 176 grams.

The product after filtration has the following characteristics:
Calcium content: 3.21 wt %
Viscosity at 100° C.: 312.2 cSt
TBN: 90.0 mg KOH/g
Free alkalinity: 45.5 mg KOH/g
Turbidity (5% solution in SN 150): 5.2 NTU (nephelometric turbidity units)

Based on the results obtained and taking into account that the free alkalinity corresponds to the content of free calcium hydroxide, the following parameters can be calculated:
Efficiency of calcium incorporation=99.8%
Neutralization yield=49.5%

It is also possible to calculate the content of salified calixarene units present as calcium salts (soap):
TBN soap=44.5 mg KOH/g
Soap content=25.5 wt %

Comparative Example 12

The method of preparation used is the same as in example 10, except that in this case p-dodecyl calix[5,6,8]arene mixed with linear oligomers from example 1 was used. The amounts of reactants and of solvents used are as follows:
Product example 1 (MW=281.1 per repeating unit, 77.5 wt % in xylene, 0.338 mol): 122.60 grams,
SN 150 base oil: 94.82 grams,
Calcium hydroxide (0.169 mol): 12.54 grams,
Ethylene glycol: 25.65 grams,
2-Ethylhexanol: 157.07 grams.

During the preparation procedure the amount of xylene removed by flash distillation is 27.5 grams.

The filtration rate was found to be very low.

The total amount of product, including that recovered after washing the filter with solvent, is 197 grams.

The product after filtration has the following characteristics:
Calcium content: 2.80 wt %
Viscosity at 100° C.: 112.3 cSt
TBN: 78.50 mg KOH/g
Free alkalinity: 62.01 mg KOH/g
Turbidity (5% solution in SN 150): 11.6 NTU (nephelometric turbidity units)

Based on the results obtained and taking into account that the free alkalinity corresponds to the content of free calcium hydroxide, the following parameters can be calculated:
Efficiency of calcium incorporation=81.4%
Neutralization yield=17.1%

It is also possible to calculate the content of salified calixarene units present as calcium salts (soap):
TBN soap=16.49 mg KOH/g
Soap content=8.8 wt %

The results in examples 10 and 11, which use calixarene products functionalized with carboxylic acid groups, and in comparative example 12, which uses a calixarene product that has not been functionalized with carboxylic acid groups, are given in Table 1. It can be seen from these results that with increase in the degree of functionalization of the calixarene with acid groups of carboxylic type, the neutralization yield increases, and so too does the content of salified calixarene units (soap) in the detergent composition. The best detergent composition for use in lubricant compositions, for example for motor vehicles, is that in example 10, as it is the one that has a higher soap content.

The partially salified detergent compositions obtained with the calixarenes of the prior art (comparative example 12) are difficult to obtain owing to the high content of sediments and poor filterability and moreover are not suitable for use in lubricant compositions on account of the low soap content.

TABLE 1

| Product | Example 10 | Example 11 | Comparative Example 12 |
|---|---|---|---|
| Calixarene | Example 3 | Example 5 | Example 1 |
| R1 | 100% | 33% | 100% |
|  | —$CH_2COOH$ | —$CH_2COOH$ | —H |
| R2 | —$C_{12}H_{25}$ | —$C_{12}H_{25}$ | —$C_{12}H_{25}$ |
| Product characteristics |  |  |  |
| Calcium content (wt %) | 2.88 | 3.21 | 2.80 |
| Viscosity at 100° C. (cSt) | 890.3 | 312.2 | 112.3 |
| TBN (mg KOH/g) | 81.0 | 90.0 | 78.5 |
| Free alkalinity (mg KOH/g) | 0 | 45.5 | 62.0 |
| Turbidity (NTU) | 5.0 | 5.2 | 11.6 |
| Results |  |  |  |
| Filtration | quick | quick | very slow |
| Efficiency of incorporation of Ca (%) | 100 | 99.8 | 81.4 |
| Neutralization yield (%, calculated) | 100 | 49.5 | 17.1 |
| Soap content (wt %, calculated) | 51.5 | 25.5 | 8.8 |

Examples 13-17: Preparation of Detergent Compositions with Medium TBN Value, Comprising Overbased Calcium Compounds of Calixarenes Examples 13 to 17 relate to the preparation of detergent compositions with a TBN value of about 250 mg KOH/g, comprising overbased calcium compounds derived from the calixarenes whose synthesis is given in examples 1 to 9. These detergent compositions were obtained using two different types of calixarenes with varying degree of functionalization with acid groups of carboxylic type, stearic acid and a weight ratio of the amount of calixarene to the amount of stearic acid of 1:2.1.

In these examples, the preparation reactions are carried out in a 0.2-litre jacketed 4-necked glass reactor, thermostatically controlled by circulating, in the jacket, a fluid obtained from a thermostatic bath. The reactor is equipped with: mechanical paddle stirrer; jacketed Dean-Stark condenser cooled with fluid from a thermostatic refrigerator, connected to a vacuum line and to a nitrogen line and equipped with a flask for collecting the distillate; thermocouple for temperature measurement; bottom discharge equipped with a teflon cock, through which carbon dioxide is bubbled into the reaction mixture. The carbon dioxide is supplied from a cylinder, placed on a balance, which is connected to the bottom of the reactor by a rubber tube.

Example 13

The reactor described above is charged in a nitrogen atmosphere: 8.77 grams of the p-tert-octyl calix[6,8]arene fully functionalized with hydroxycarbonyl-methoxy groups from example 8 (MW=276.4 per repeating unit, 0.0317 mol), 51.49 grams of 2-ethylhexanol and 24.40 grams of SN 150 base oil. The mixture is heated with stirring (500 rev/min) to give a temperature inside the reactor of 130° C. Once this temperature is reached, 10.34 grams of calcium hydroxide (0.140 mol) is added via a charging funnel. The nitrogen is cut off and vacuum is applied, gradually lowering the pressure to 70 mbar. It is left in these conditions for 15 minutes. Next, the vacuum is broken, the nitrogen atmosphere is restored and 18.21 grams of stearic acid (0.064 mol) is added to the mixture, held at a temperature of 130° C., in the space of about 10 minutes. The nitrogen is cut off and vacuum is applied, gradually lowering the pressure to 70 mbar. It is left in these conditions for 15 minutes. The vacuum is broken, the nitrogen atmosphere is restored and 6.73 grams of ethylene glycol is added, by dropping funnel, in about 5 minutes. Next, the nitrogen is cut off and vacuum is applied, gradually lowering the pressure until the pressure is 70 mbar. It is left in these conditions for 60 minutes, during which the 2-ethylhexanol-water azeotrope is distilled and is collected in the Dean-Stark condenser, where the water, which also contains small amounts of ethylene glycol, is separated from the 2-ethylhexanol.

The vacuum is broken, the nitrogen atmosphere is restored and 10.8 grams of carbon dioxide at a temperature of 130° C. is added in 60 minutes, stirring the mixture at 600 rev/min. At the end of adding the carbon dioxide, the stirring speed is reduced to 500 rev/min, the pressure is gradually lowered to 70 mbar and then the reaction mixture is heated from 130° C. to 200° C., by increasing the temperature of the thermostatic bath from 140° C. to 210° C. in 70 minutes (10° C. every 10 minutes). During this step the solvent is removed by flash distillation and is collected in a flask connected to the Dean-Stark condenser.

Once the reaction mixture has reached a temperature of 200° C. the pressure is further reduced to below 10 mbar and these conditions are maintained for 60 minutes to remove the greater part of the residual solvent from the product. Then the reaction mixture is cooled to 160° C., the vacuum is broken and the nitrogen atmosphere is restored.

An amount of filter aid equal to 2 g is added to the stirred mixture at a temperature of 160° C., and after mixing for 15 minutes it is filtered on a 0.4-litre jacketed steel filter, having a filtering surface consisting of an 80-mesh steel screen. Prior to filtration, a layer of filtering earth is prepared on the filter. Filtration is carried out at a temperature of 160° C. and with a pressure of 5 atmospheres of nitrogen.

A high filtration rate was obtained.

The total amount of product, including that recovered after washing the filter with solvent, is 62.6 grams.

The product after filtration has the following characteristics:
Calcium content: 8.88 wt %
Viscosity at 100° C.: 85.5 cSt
TBN: 248.8 mg KOH/g
Turbidity (5% solution in SN 150): 10.7 NTU (nephelometric turbidity units)

Based on the results obtained, it is possible to calculate the efficiency of incorporation of calcium into the detergent composition. Moreover, bearing in mind that both the stearic acid and the calixarene used in this example (fully functionalized with carboxylic acid groups) are fully salified by the calcium hydroxide, it is possible to calculate the content of calcium stearate, of calcium salts of the calixarene product and the total content of organic calcium salts (total soap).
Efficiency of calcium incorporation=99.3%

Calcium stearate=31.1 wt %
Calcium salts of the calixarene product=15 wt %
Total soap content=46.1 wt %.

Example 14

The method of preparation used is the same as in example 13, except that in this case the p-dodecyl calix[5,6,8]arene mixed with linear oligomers fully functionalized with hydroxycarbonyl-methoxy groups of example 4 was used. The amounts of reactants and of solvents used are as follows:
- Product example 4 (MW=339.1 per repeating unit, 0.0256 mol): 8.69 grams,
- 2-Ethylhexanol: 52.60 grams,
- SN 150 base oil: 23.57 grams,
- Calcium hydroxide (0.140 mol): 10.41 grams,
- Stearic acid (0.0634 mol): 18.04 grams,
- Ethylene glycol: 6.66 grams,
- Carbon dioxide: (0.246 mol): 10.84 grams A high filtration rate was obtained.

The total amount of product, including that recovered after washing the filter with solvent, is 61.7 grams.

The product after filtration has the following characteristics:
Calcium content: 9.07 wt %
Viscosity at 100° C.: 85.7 cSt
TBN: 254.0 mg KOH/g
Turbidity (5% solution in SN 150): 7.1 NTU (nephelometric turbidity units)

Based on the results obtained, it is possible to calculate the efficiency of incorporation of calcium into the detergent composition. Moreover, bearing in mind that both the stearic acid and the calixarene used in this example (fully functionalized with carboxylic acid groups) are fully salified by the calcium hydroxide, it is possible to calculate the content of calcium stearate, of calcium salts of the calixarene product and the total content of organic calcium salts (total soap).
Efficiency of calcium incorporation=99.4%
Calcium stearate=31.2 wt %
Calcium salts of the calixarene product=14.9 wt %
Soap content=46.1 wt %

Example 15

The method of preparation used is the same as in example 13, except that in this case the p-tert-octyl calix[6,8]arene 50% functionalized with hydroxycarbonylmethoxy groups of example 9 was used. The amounts of reactants and of solvents used are as follows:
- Calixarene example 9 (MW=247.4 per repeating unit, 0.0350 mol): 8.66 grams,
- 2-Ethylhexanol: 52.49 grams,
- SN 150 base oil: 24.09 grams,
- Calcium hydroxide (0.141 mol): 10.45 grams,
- Stearic acid (0.0632 mol): 17.99 grams,
- Ethylene glycol: 6.65 grams,
- Carbon dioxide: (0.247 mol): 10.88 grams A high filtration rate was obtained.

The total amount of product, including that recovered after washing the filter with solvent, is 61.8 grams.

The product after filtration has the following characteristics:
Calcium content: 9 wt %
Viscosity at 100° C.: 82 cSt
TBN: 252 mg KOH/g
Turbidity (5% solution in SN 150): 7 NTU (nephelometric turbidity units)

Based on the results obtained, it is possible to calculate the efficiency of incorporation of calcium into the detergent composition. Moreover, considering that the stearic acid is fully salified by the calcium hydroxide, while the calixarene used in this example (partially functionalized with carboxylic acid groups) is salified completely for the carboxyl moiety, but partially for the phenolic moiety (17.1%, as in example 12), it is possible to calculate the content of calcium stearate, of calcium salts of the calixarene product and the total content of organic calcium salts (total soap).
Efficiency of calcium incorporation=98.7%
Calcium stearate=31.1 wt %
Calcium salts of the calixarene product=8.8 wt %
Total soap content=39.9 wt %

Comparative Example 16

The method of preparation used is the same as in example 13, except that in this case the p-tert-octyl calix[6,8]arene of example 7 was used. The amounts of reactants and of solvents used are as follows:
- Calixarene example 7 (MW=218.3 per repeating unit, 0.0395 mol): 8.63 grams,
- 2-Ethylhexanol: 52.37 grams,
- SN 150 base oil: 24.31 grams,
- Calcium hydroxide (0.141 mol): 10.45 grams,
- Stearic acid (0.0630 mol): 17.93 grams,
- Ethylene glycol: 6.62 grams,
- Carbon dioxide: (0.247 mol): 10.88 grams A high filtration rate was obtained.

The total amount of product, including that recovered after washing the filter with solvent, is 62.2 grams.

The product after filtration has the following characteristics:
Calcium content: 9.06 wt %
Viscosity at 100° C.: 43.5 cSt
TBN: 254 mg KOH/g
Turbidity (5% solution in SN 150): 3.8 NTU (nephelometric turbidity units)

Based on the results obtained, it is possible to calculate the efficiency of incorporation of calcium into the detergent composition. Moreover, considering that the stearic acid is fully salified by the calcium hydroxide and that the calixarene used in this example is salified partially (17.1%, as in example 12), it is possible to calculate the content of calcium stearate, of calcium salts of the calixarene product and the total content of organic calcium salts (total soap).
Efficiency of calcium incorporation=99.8%
Calcium stearate=30.6 wt %
Calcium salts of the calixarene product=2.5 wt %
Total soap content=33.1 wt %

Comparative Example 17

The method of preparation used is the same as in example 13, except that in this case the p-dodecyl calix[5,6,8]arene mixed with linear oligomers from example 2 was used. The amounts of reactants and of solvents used are as follows:
- Calixarene example 2 (MW=281.1 per repeating unit, 0.0309 mol): 8.68 grams,
- 2-Ethylhexanol: 52.61 grams,
- SN 150 base oil: 23.90 grams,
- Calcium hydroxide (0.141 mol): 10.45 grams,
- Stearic acid (0.0634 mol): 18.04 grams,
- Ethylene glycol: 6.66 grams,
- Carbon dioxide: (0.247 mol): 10.88 grams A high filtration rate was obtained.

The total amount of product, including that recovered after washing the filter with solvent, is 61.9 grams.

The product after filtration has the following characteristics:

Calcium content: 9.02 wt %
Viscosity at 100° C.: 55.6 cSt
TBN: 252.5 mg KOH/g
Turbidity (5% solution in SN 150): 4.8 NTU (nephelometric turbidity units)

Based on the results obtained, it is possible to calculate the efficiency of incorporation of calcium into the detergent composition. Moreover, considering that the stearic acid is fully salified by the calcium hydroxide and that the calixarene used in this example is salified partially (17.1%, as in example 12), it is possible to calculate the content of calcium stearate, of calcium salts of the calixarene product and the total content of organic calcium salts (total soap).

Efficiency of calcium incorporation=98.7%
Calcium stearate=31.1 wt %
Calcium salts of the calixarene product=2.6 wt %
Total soap content=33.7 wt %

Example 18

The method of preparation used is the same as in example 13. The p-tert-octyl calix[6,8]arene fully functionalized with hydroxycarbonyl-methoxy groups of example 8 and stearic acid were used in this example. The amounts of reactants and of solvents used are as follows:

Calixarene example 8 (MW=276.4 per repeating unit, 0.0314 mol): 8.68 grams,
2-Ethylhexanol: 51.09 grams,
SN 150 base oil: 19.22 grams,
Calcium hydroxide (0.188 mol): 13.92 grams,
Stearic acid (0.0634 mol): 18.03 grams,
Ethylene glycol: 6.66 grams,
Carbon dioxide: (0.329 mol): 14.50 grams The filtration rate was found to be low.

The total amount of product, including that recovered after washing the filter with solvent, is 59.8 grams.

The product after filtration has the following characteristics:

Calcium content: 11.08 wt %
Viscosity at 100° C.: 503.5 cSt
TBN: 310 mg KOH/g

TABLE 2

| Product | Example 13 | Example 14 | Example 15 | Comparative Example 16 | Comparative Example 17 |
|---|---|---|---|---|---|
| Calixarene | Example 8 | Example 4 | Example 9 | Example 7 | Example 2 |
| R1 | 100% —$CH_2COOH$ | 100% —$CH_2COOH$ | 50% —$CH_2COOH$ | 100% —H | 100% —H |
| R2 | —$C_8H_{17}$ | —$C_{12}H_{25}$ | —$C_8H_{17}$ | —$C_8H_{17}$ | —$C_{12}H_{25}$ |
| Alkyl carboxylic acid | Stearic acid | Stearic acid | Stearic acid | Stearic acid | Stearic acid |
| Product characteristics | | | | | |
| Calcium content (wt %) | 8.88 | 9.07 | 9.00 | 9.06 | 9.02 |
| Viscosity at 100° C. (cSt) | 85.5 | 85.7 | 82.0 | 43.5 | 55.6 |
| TBN (mg KOH/g) | 248.8 | 254.0 | 252.0 | 254.0 | 252.5 |
| Turbidity (NTU) | 10.7 | 7.1 | 7.0 | 3.8 | 4.8 |
| Results | | | | | |
| Filtration | quick | quick | quick | quick | quick |
| Efficiency of incorporation of Ca (%) | 99.3 | 99.4 | 98.7 | 99.8 | 98.7 |
| Calcium stearate (wt %, calculated) | 31.1 | 31.2 | 31.1 | 30.6 | 31.1 |
| Calcium salts of the calixarene product (wt %, calculated) | 15.0 | 14.9 | 8.8 | 2.5 | 2.6 |
| Total soap content (wt %, calculated) | 46.1 | 46.1 | 39.9 | 33.1 | 33.7 |

Examples 18-23: Preparation of Detergent Compositions with High TBN Value, Comprising Overbased Metal Compounds of Calixarenes Examples 18 to 23 relate to the preparation of detergent compositions with a TBN value of about 300 mg KOH/g and above, obtained using various types of calixarenes with various degrees of functionalization, two different types of alkyl carboxylic acids (stearic acid and isostearic acid) and two different ratios by weight of the amount of calixarene to the amount of alkyl carboxylic acid (1:1 and 1:2.1). The preparation procedure used is the same as in examples 13 to 17 with respect to the times and the reaction temperatures, the types of solvents and the order of adding the various components.

Turbidity (5% solution in SN 150): 7.5 NTU (nephelometric turbidity units).

Based on the results obtained, it is possible to calculate the efficiency of incorporation of calcium into the detergent composition. Moreover, bearing in mind that both the stearic acid and the calixarene used in this example (fully functionalized with carboxylic acid groups) are fully salified by the calcium hydroxide, it is possible to calculate the content of calcium stearate, of calcium salts of the calixarene product and the total content of organic calcium salts (total soap).

Efficiency of calcium incorporation=88%
Calcium stearate=32.2 wt %
Calcium salts of the calixarene product=15.5 wt %
Total soap content=47.7 wt %

Example 19

The method of preparation used is the same as in example 13. The p-tert-octyl calix[6,8]arene fully functionalized with hydroxycarbonyl-methoxy groups of example 8 and isostearic acid in place of stearic acid were used in this example. The amounts of reactants and of solvents used are as follows:
Calixarene example 8 (MW=276.4 per repeating unit, 0.0314 mol): 8.68 grams,
2-Ethylhexanol: 51.09 grams,
SN 150 base oil: 19.22 grams,
Calcium hydroxide (0.188 mol): 13.92 grams,
Isostearic acid (0.0636 mol): 18.03 grams,
Ethylene glycol: 6.66 grams,
Carbon dioxide: (0.329 mol): 14.50 grams
The filtration rate was found to be low.
The total amount of product, including that recovered after washing the filter with solvent, is 59.7 grams.
The product after filtration has the following characteristics:
Calcium content: 11.04 wt %
Viscosity at 100° C.: 234.8 cSt
TBN: 309 mg KOH/g
Turbidity (5% solution in SN 150): 5.6 NTU (nephelometric turbidity units)
Based on the results obtained, it is possible to calculate the efficiency of incorporation of calcium into the detergent composition. Moreover, considering that both the isostearic acid and the calixarene used in this example (fully functionalized with carboxylic acid groups) are fully salified by the calcium hydroxide, it is possible to calculate the content of calcium isostearate, of calcium salts of the calixarene product and the total content of organic calcium salts (total soap).
Efficiency of calcium incorporation=87.5%
Calcium isostearate=32.2 wt %
Calcium salts of the calixarene product=15.6 wt %
Total soap content=47.8 wt %

Example 20

The method of preparation used is the same as in example 13. In this example the p-dodecyl calix[5,6,8]arene mixed with linear oligomers fully functionalized with hydroxycarbonyl-methoxy groups of example 4 and isostearic acid were used. The amounts of reactants and of solvents used are as follows:
Calixarene example 4 (MW=339.1 per repeating unit, 0.0257 mol): 8.72 grams,
2-Ethylhexanol: 52.75 grams,
SN 150 base oil: 18.95 grams,
Calcium hydroxide (0.188 mol): 13.92 grams,
Isostearic acid (0.0636 mol): 18.10 grams,
Ethylene glycol: 6.68 grams,
Carbon dioxide: (0.329 mol): 14.50 grams
The filtration rate was found to be low.
The total amount of product, including that recovered after washing the filter with solvent, is 60.6 grams.
The product after filtration has the following characteristics:
Calcium content: 11.46 wt %
Viscosity at 100° C.: 194.4 cSt
TBN: 320.8 mg KOH/g
Turbidity (5% solution in SN 150): 6 NTU (nephelometric turbidity units)
Based on the results obtained, it is possible to calculate the efficiency of incorporation of calcium into the detergent composition. Moreover, considering that both the isostearic acid and the calixarene used in this example (fully functionalized with carboxylic acid groups) are fully salified by the calcium hydroxide, it is possible to calculate the content of calcium isostearate, of calcium salts of the calixarene product and the total content of organic calcium salts (total soap).
Efficiency of calcium incorporation=92.2%
Calcium isostearate=31.9 wt %
Calcium salts of the calixarene product=15.2 wt %
Total soap content=47.1 wt %

Example 21

The method of preparation used is the same as in example 13. In this example the p-dodecyl calix[5,6,8]arene mixed with linear oligomers fully functionalized with hydroxycarbonyl-methoxy groups of example 4 and isostearic acid were used. Relative to example 20, a higher weight ratio of the amount of calixarene to the amount of isostearic acid was used (1:1 in the present example and 1:2.1 in example 20). The amounts of reactants and of solvents used are as follows:
Calixarene example 4 (MW=339.1 per repeating unit, 0.0396 mol): 13.43 grams,
2-Ethylhexanol: 52.88 grams,
SN 150 base oil: 18.82 grams,
Calcium hydroxide (0.188 mol): 13.92 grams,
Isostearic acid (0.0472 mol): 13.43 grams,
Ethylene glycol: 6.69 grams,
Carbon dioxide: (0.329 mol): 14.50 grams
The filtration rate was found to be low.
The total amount of product, including that recovered after washing the filter with solvent, is 61.4 grams.
The product after filtration has the following characteristics:
Calcium content: 11.86 wt %
Viscosity at 100° C.: 303 cSt
TBN: 332 mg KOH/g
Turbidity (5% solution in SN 150): 5.9 NTU (nephelometric turbidity units)
Based on the results obtained, it is possible to calculate the efficiency of incorporation of calcium into the detergent composition. Moreover, considering that both the isostearic acid and the calixarene used in this example (fully functionalized with carboxylic acid groups) are fully salified by the calcium hydroxide, it is possible to calculate the content of calcium isostearate, of calcium salts of the calixarene product and the total content of organic calcium salts (total soap).
Efficiency of calcium incorporation=96.5%
Calcium isostearate=23.3 wt %
Calcium salts of the calixarene product=23.2 wt %
Total soap content=46.5 wt %

Example 22

The method of preparation used is the same as in example 13. In this example the p-tert-octyl calix[6,8]arene 50% functionalized with hydroxycarbonylmethoxy groups of example 9 and isostearic acid were used, with a weight ratio of the amount of calixarene to the amount of isostearic acid of 1:1. The amounts of reactants and of solvents used are as follows:
Calixarene example 9 (MW=247.4 per repeating unit 0.0537 mol): 13.30 grams,
2-Ethylhexanol: 52.43 grams,
SN 150 base oil: 19.51 grams,
Calcium hydroxide (0.188 mol): 13.92 grams, Isostearic acid (0.0467 mol): 13.30 grams,
Ethylene glycol: 6.63 grams,
Carbon dioxide: (0.329 mol): 14.50 grams
The filtration rate was found to be low.

The total amount of product, including that recovered after washing the filter with solvent, is 60.4 grams.

The product after filtration has the following characteristics:
Calcium content: 10.95 wt %
Viscosity at 100° C.: 510 cSt
TBN: 309.8 mg KOH/g
Turbidity (5% solution in SN 150): 7.5 NTU (nephelometric turbidity units)

Based on the results obtained, it is possible to calculate the efficiency of incorporation of calcium into the detergent composition. Moreover, considering that the isostearic acid is fully salified by the calcium hydroxide, while the calixarene used in this example (partially functionalized with carboxylic acid groups) is salified completely for the carboxyl moiety, but partially for the phenolic moiety (17.1%, as in example 12), it is possible to calculate the content of calcium isostearate, of calcium salts of the calixarene product and the total content of organic calcium salts (total soap).
Efficiency of calcium incorporation=87.8%
Calcium isostearate=23.5 wt %
Calcium salts of the calixarene product=13.9 wt %
Soap content=37.4 wt %

Comparative Example 23

The method of preparation used is the same as in example 13. In this example the p-tert-octyl calix[6,8]arene of example 7 and stearic acid were used. The amounts of reactants and of solvents used are as follows:

Calixarene example 7 (MW=218.3 per repeating unit, 0.0395 mol): 8.63 grams,
2-Ethylhexanol: 52.37 grams,
SN 150 base oil: 19.61 grams,
Calcium hydroxide (0.188 mol): 13.92 grams,
Stearic acid (0.0630 mol): 17.93 grams,
Ethylene glycol: 6.62 grams,
Carbon dioxide: (0.329 mol): 14.50 grams
The filtration rate was found to be low.

The total amount of product, including that recovered after washing the filter with solvent, is 59.9 grams.

The product after filtration has the following characteristics:
Calcium content: 10.50 wt %
Viscosity at 100° C.: 280 cSt
TBN: 299 mg KOH/g
Turbidity (5% solution in SN 150): 6.5 NTU (nephelometric turbidity units)

Based on the results obtained, it is possible to calculate the efficiency of incorporation of calcium into the detergent composition. Moreover, considering that the stearic acid is fully salified by the calcium hydroxide and that the calixarene used in this example is salified partially (17.1%, as in example 12), it is possible to calculate the content of calcium stearate, of calcium salts of the calixarene product and the total content of organic calcium salts (total soap).
Efficiency of calcium incorporation=83.5%
Calcium stearate=31.9 wt %
Calcium salts of the calixarene product=2.7 wt %
Soap content=34.6 wt %

The results of examples 18 to 22, which use calixarene products functionalized with carboxylic acid groups, and of comparative example 23, which uses p-tert-octyl calix[6,8]arene, are given in Table 3. As expected, with increase in the degree of functionalization of the calixarene with acid groups of carboxylic type, the content of calcium salts of the calixarene product and the total soap content increase in the detergent composition.

The efficiency of incorporation of calcium into the detergent composition is in general better for the products derived from calixarenes functionalized with carboxylic acid groups relative to those that are unfunctionalized (compare examples 18 to 22 and comparative example 23) and moreover, at equal carboxyl functionalization, the calixarenes that give products with lower viscosity and with higher efficiency of incorporation of calcium and therefore with higher alkalinity (TBN) are those derived from p-dodecylphenol (compare example 20 with example 19). Moreover, the use of isostearic acid in place of stearic acid, in combination with the calixarenes, makes it possible to obtain products that are more fluid. The use of the calixarenes from p-dodecylphenol in combination with isostearic acid makes it possible to obtain detergent compositions with high content of calixarene products, characterized by good efficiency of incorporation of calcium and viscosity values that are not high (example 21).

For all the detergent compositions of examples 18 to 23, filtration was complete, even if slow.

TABLE 3

| Product | Example 18 | Example 19 | Example 20 | Example 21 | Example 22 | Comparative Example 23 |
|---|---|---|---|---|---|---|
| Calixarene | Example 8 | Example 8 | Example 4 | Example 4 | Example 9 | Example 7 |
| R1 | 100% | 100% | 100% | 100% | 50% | 100% |
|  | —$CH_2COOH$ | —$CH_2COOH$ | —$CH_2COOH$ | —$CH_2COOH$ | —$CH_2COOH$ | —H |
| R2 | —$C_8H_{17}$ | —$C_8H_{17}$ | —$C_{12}H_{25}$ | —$C_{12}H_{25}$ | —$C_8H_{17}$ | —$C_8H_{17}$ |
| Alkyl carboxylic acid | Stearic acid | Isostearic acid | Isostearic acid | Isostearic acid | Isostearic acid | Stearic acid |
| Product characteristics |  |  |  |  |  |  |
| Calcium content (wt %) | 11.08 | 11.04 | 11.46 | 11.86 | 10.95 | 10.50 |
| Viscosity at 100° C. (cSt) | 503.5 | 234.8 | 194.4 | 303.0 | 510.0 | 280.0 |
| TBN (mg KOH/g) | 310.0 | 309.0 | 320.8 | 332.0 | 309.8 | 299.0 |
| Turbidity (NTU) | 7.5 | 5.6 | 6.0 | 5.9 | 7.5 | 6.5 |

TABLE 3-continued

| Product | Example 18 | Example 19 | Example 20 | Example 21 | Example 22 | Comparative Example 23 |
|---|---|---|---|---|---|---|
| Results | | | | | | |
| Filtration | slow | slow | slow | slow | slow | slow |
| Efficiency of incorporation of Ca (%) | 88.0 | 87.5 | 92.2 | 96.5 | 87.8 | 83.5 |
| Calcium stearate (wt %, calculated) | 32.2 | — | — | — | — | 31.9 |
| Calcium isostearate (wt %, calculated) | — | 32.2 | 31.9 | 23.3 | 23.5 | — |
| Calixarene calcium salts (wt %, calculated) | 15.5 | 15.6 | 15.2 | 23.2 | 13.9 | 2.7 |
| Total soap content (wt %, calculated) | 47.7 | 47.8 | 47.1 | 46.5 | 37.4 | 34.6 |

Examples 24-27: Preparation of Detergent Compositions with High TBN Value, Comprising Overbased Calcium Compounds of Calixarenes Examples 24 to 27 relate to the preparation of detergent compositions with a TBN value of about 300 mg KOH/g and weight ratio of the amount of calixarene used to that of isostearic acid of 1:1. The method of preparation used differs from that in examples 18 to 23 with respect to the order of adding the various components and in particular the use of fractional additions of ethylene glycol.

In these examples the preparation reactions are carried out in an RC-1 Mettler calorimeter consisting of a 0.5-litre jacketed 5-necked glass reactor, thermostatically controlled by circulation, in the jacket, of a fluid obtained from a thermostatic bath inside the instrument. The reactor is equipped with: mechanical paddle stirrer; Dean-Stark condenser cooled with mains water, connected to a vacuum line and to a nitrogen line and equipped with a flask for collecting the distillate; bottom discharge equipped with a teflon cock; thermocouple for temperature measurement; glass dip tube with porous septum at the end for bubbling carbon dioxide into the reaction mixture. The carbon dioxide is supplied from a cylinder fitted with a pressure reducer, placed on a balance.

The flow of carbon dioxide is controlled by a mass flow meter that is connected to the cylinder and to the glass dip tube by rubber tubes.

The whole system is controlled by a computer, which allows the reactor to be automated, setting the desired heating and cooling programmes.

Example 24

The reactor described above is charged in a nitrogen atmosphere: 77.67 grams of the p-dodecyl calix[5,6,8]arene mixed with linear oligomers fully functionalized with hydroxycarbonyl-methoxy groups of example 3 (MW=339.1 per repeating unit, 53 wt % in xylene, 0.121 mol), 41.25 grams of isostearic acid (0.145 mol) and 63.61 grams of SN 150 base oil.

The mixture is heated with stirring (500 rev/min) at a temperature of 80° C., it is left in these conditions for 15 minutes, and then it is heated to give a temperature inside the reactor of 130° C. Then the xylene is removed by flash distillation, cutting off the nitrogen and gradually lowering the pressure to about 20 mbar. 36.5 g of xylene is collected.

The vacuum is broken, the nitrogen atmosphere is restored and 38.28 g of calcium hydroxide (0.517 mol) is added via a charging funnel at a temperature of 130° C., in the space of about 5 minutes. While stirring, 137.57 grams of 2-ethylhexanol is then added via the same charging funnel.

The nitrogen is cut off and vacuum is applied, gradually lowering the pressure until it is 150 mbar. It is left in these conditions for 15 minutes. The vacuum is broken, the nitrogen atmosphere is restored and 20.59 grams of ethylene glycol is added, by dropping funnel, in about 5 minutes.

The nitrogen is cut off and vacuum is applied, gradually lowering the pressure to 70 mbar. It is left in these conditions for 90 minutes, during which the 2-ethylhexanol-water azeotrope is distilled and is collected in the Dean-Stark condenser, where the water, which also contains small amounts of ethylene glycol, is separated from the 2-ethylhexanol.

The vacuum is broken, the nitrogen atmosphere is restored and 14.91 grams of ethylene glycol is added by dropping funnel, at a temperature of 130° C.

Then 37.5 grams of carbon dioxide (0.852 mol) is added at a temperature of 130° C. in the space of 90 minutes, stirring the mixture at 750 rev/min.

At the end of adding the carbon dioxide, the stirring speed is reduced to 500 rev/min, the pressure is gradually lowered to 70 mbar and then the mixture is heated from 130° C. to 200° C., programming the temperature rise of the thermostatic bath from 140° C. to 2100° C. in 70 minutes (1° C. per minute). During this step the solvent is removed by flash distillation and is collected in a flask connected to the Dean-Stark condenser.

Once a temperature of 200° C. is reached, the pressure is further reduced to below 10 mbar and these conditions are maintained for 60 minutes to remove the greater part of the residual solvent from the product. Then the reaction mixture is cooled to 160° C., the vacuum is broken and the nitrogen atmosphere is restored.

An amount of filter aid equal to 6 grams is added to the stirred mixture at a temperature of 160° C., and after mixing for 15 minutes it is filtered on a 0.4-litre jacketed steel filter, having a filtering surface consisting of an 80-mesh steel screen. Prior to filtration, a layer of filtering earth is prepared on the filter. Filtration is carried out at a temperature of 160° C. and with a pressure of 5 atmospheres of nitrogen.

A medium filtration rate was obtained.

The total amount of product, including that recovered after washing the filter with solvent, is 189.2 grams.

The product after filtration has the following characteristics:
Calcium content: 10.88 wt %
Viscosity at 100° C.: 140.8 cSt
TBN: 304.5 mg KOH/g
Free alkalinity: 14.4 mg KOH/g
Turbidity (5% solution in SN 150): 5.1 NTU (nephelometric turbidity units)

Based on the results obtained, it is possible to calculate the efficiency of incorporation of calcium into the detergent composition. Moreover, taking into account that the free alkalinity corresponds to the content of free calcium hydroxide and that isostearic acid and the calixarene used in this example (fully functionalized with carboxylic acid groups) are fully salified by the calcium hydroxide, it is possible to calculate the percentage carbonation of the calcium hydroxide in excess with respect to the salification reaction, the content of calcium isostearate, of calcium salts of the calixarene product and the total content of organic calcium salts (total soap).
Efficiency of calcium incorporation=99.4%
Calcium hydroxide carbonation=93.6%
Calcium isostearate=23.2 wt %
Calcium salts of the calixarene product=23 wt %
Total soap content=46.2 wt %

Example 25

The method of preparation used is the same as in example 24. The p-dodecyl calix[5,6,8]arene+linear oligomers fully functionalized with 4-(hydroxycarbonyl)-benzyloxy groups of example 6 and isostearic acid were used in this example. The amounts of reactants and of solvents used are as follows:
  Calixarene example 6 (MW=429.2 per repeating unit, 52.5 wt % in xylene, 0.096 mol): 79.00 grams,
  Isostearic acid (0.146 mol): 41.48 grams,
  SN 150 base oil: 62.4 grams,
  Calcium hydroxide (0.517 mol): 38.28 grams,
  2-Ethylhexanol: 138.27 grams,
  Ethylene glycol (1st addition): 20.71 grams,
  Ethylene glycol (2nd addition): 14.99 grams,
  Carbon dioxide: (0.834 mol): 38.6 grams
At the beginning of the preparation procedure, 37.6 grams of xylene is removed by distillation.
The filtration rate was found to be low.
The total amount of product, including that recovered after washing the filter with solvent, is 189.3 grams.
The product after filtration has the following characteristics:
Appearance: dark clear liquid
Calcium content: 10.87 wt %
Viscosity at 100° C.: 174.5 cSt
TBN: 304.4 mg KOH/g
Free alkalinity: 15.5 mg KOH/g
Turbidity (5% solution in SN 150): 5.4 NTU (nephelometric turbidity units)

Based on the results obtained, it is possible to calculate the efficiency of incorporation of calcium into the detergent composition. Moreover, taking into account that the free alkalinity corresponds to the content of free calcium hydroxide and that isostearic acid and the calixarene used in this example (fully functionalized with acid groups of the benzoic type) are fully salified by the calcium hydroxide, it is possible to calculate the percentage carbonation of the calcium hydroxide in excess with respect to the salification reaction, the content of calcium isostearate, of calcium salts of the calixarene product and the total content of organic calcium salts (total soap).
Efficiency of calcium incorporation=99.3%
Calcium hydroxide carbonation=93.4%
Calcium isostearate=23.4 wt %
Calcium salts of the calixarene product=22.9 wt %
Total soap content=46.3 wt %

Example 26

The method of preparation used is the same as in example 24. The p-dodecyl calix[5,6,8]arene mixed with linear oligomers 33% functionalized with hydroxycarbonyl-methoxy groups from example 5 and isostearic acid were used in this example. The amounts of reactants and of solvents used are as follows:
  Calixarene example 5 (MW=300.2 per repeating unit, 53.5 wt % in xylene, 0.137 mol): 76.65 grams,
  Isostearic acid (0.144 mol): 41.11 grams,
  SN 150 base oil: 64.35 grams,
  Calcium hydroxide (0.517 mol): 38.28 grams,
  2-Ethylhexanol: 137.26 grams,
  Ethylene glycol (1st addition): 20.54 grams,
  Ethylene glycol (2nd addition): 14.87 grams,
  Carbon dioxide: (0.834 mol): 36.7 grams
At the beginning of the preparation procedure, 35.6 grams of xylene is removed by distillation.
The filtration rate was found to be low.
The total amount of product, including that recovered after washing the filter with solvent, is 189.9 grams.
The product after filtration has the following characteristics:
Calcium content: 10.57 wt %
Viscosity at 100° C.: 136.4 cSt
TBN: 298.1 mg KOH/g
Free alkalinity: 16.3 mg KOH/g
Turbidity (5% solution in SN 150): 5.3 NTU (nephelometric turbidity units)

Based on the results obtained, it is possible to calculate the efficiency of incorporation of calcium into the detergent composition. Moreover, taking into account that the free alkalinity corresponds to the content of free calcium hydroxide, that the isostearic acid is fully salified by the calcium hydroxide and that the calixarene used in this example (partially functionalized with carboxylic acid groups) is fully salified with respect to the carboxyl moiety, but partially for the phenolic moiety (17.1%, as in example 12), it is possible to calculate the percentage carbonation of the calcium hydroxide in excess with respect to the salification reaction, the content of calcium isostearate, of calcium salts of the calixarene product and the total content of organic calcium salts (total soap).
Efficiency of calcium incorporation=97%
Calcium hydroxide carbonation=93.3%
Calcium isostearate=23.1 wt %
Calcium salts of the calixarene product=10.2 wt %
Total soap content=33.3 wt %

Comparative Example 27

The method of preparation used is the same as in example 24. The p-dodecyl calix[5,6,8]arene mixed with linear oligomers from example 1 and isostearic acid were used in this example. The amounts of reactants and of solvents used are as follows:

Calixarene example 1 (MW=281.1 per repeating unit, 77.5 wt % in xylene, 0.146 mol): 52.83 grams,
Isostearic acid (0.144 mol): 41.02 grams,
SN 150 base oil: 64.79 grams,
Calcium hydroxide (0.517 mol): 38.28 grams,
2-Ethylhexanol: 137.01 grams,
Ethylene glycol (1st addition): 20.50 grams,
Ethylene glycol (2nd addition): 14.84 grams,
Carbon dioxide: (0.834 mol): 36.3 grams At the beginning of the preparation procedure, 11.9 grams of xylene is removed by distillation.

The filtration rate was found to be low.

The total amount of product, including that recovered after washing the filter with solvent, is 188.9 grams.

The product after filtration has the following characteristics:
Calcium content: 10.27 wt %
Viscosity at 100° C.: 80.5 cSt
TBN: 290.5 mg KOH/g
Free alkalinity: 15.3 mg KOH/g
Turbidity (5% solution in SN 150): 4.2 NTU (nephelometric turbidity units)

Based on the results obtained, it is possible to calculate the efficiency of incorporation of calcium into the detergent composition. Moreover, taking into account that the free alkalinity corresponds to the content of free calcium hydroxide, that the isostearic acid is fully salified by the calcium hydroxide and that the calixarene used in this example is salified partially (17.1%, as in example 12), it is possible to calculate the percentage carbonation of the calcium hydroxide in excess with respect to the salification reaction, the content of calcium isostearate, of calcium salts of the calixarene product and the total content of organic calcium salts (total soap).

Efficiency of calcium incorporation=93.7%
Calcium hydroxide carbonation=94%
Calcium isostearate=23.1 wt %
Calcium salts of the calixarene product=4 wt %
Total soap content=27.1 wt %

The results in examples 24 to 26, which use calixarene products functionalized with carboxylic acid groups, and in comparative example 27, which uses a mixture of p-dodecyl calix[5,6,8]arene+linear oligomers, are given in Table 4. As expected, with increase in the degree of functionalization of the calixarene with acid groups of carboxylic type, the content of calcium salts of the calixarene product and the total soap content in the detergent composition increase.

In examples 24 to 27, changing, relative to examples 18 to 23, the amounts and the order of adding the various components, in particular with respect to ethylene glycol, generally led to an increase in the efficiency of incorporation of calcium into the detergent compositions. The total amount of ethylene glycol added, calculated relative to the total charge, was increased and was split into two aliquots, the first being added during the salification reaction and the second being added before carbonation with carbon dioxide.

The second aliquot of ethylene glycol was added to replace the ethylene glycol removed by distillation together with 2-ethylhexanol and water during the salification step.

The efficiency of incorporation of calcium into the detergent composition is, however, still better for the products derived from calixarenes functionalized with carboxylic acid groups, relative to those that are unfunctionalized (compare examples 24 to 26 and comparative example 27).

For the detergent composition of example 24, a medium filtration rate was obtained; for the detergent compositions of all the other examples filtration was complete, even if slower.

TABLE 4

| Product | Example 24 | Example 25 | Example 26 | Comparative Example 27 |
|---|---|---|---|---|
| Calixarene | Example 3 | Example 6 | Example 5 | Example 1 |
| R1 | 100% | 100% | 33% | 100% |
|  | —$CH_2COOH$ | —$CH_2$—$C_6H_4$—COOH | —$CH_2COOH$ | —H |
| R2 | —$C_{12}H_{25}$ | —$C_{12}H_{25}$ | —$C_{12}H_{25}$ | —$C_{12}H_{25}$ |
| Alkyl carboxylic acid | Isostearic acid | Isostearic acid | Isostearic acid | Isostearic acid |
| Product characteristics | | | | |
| Calcium content (wt %) | 10.88 | 10.87 | 10.57 | 10.27 |
| Viscosity at 100° C. (cSt) | 140.8 | 174.5 | 136.4 | 80.5 |
| TBN (mg KOH/g) | 304.5 | 304.4 | 298.1 | 290.5 |
| Free alkalinity (mg KOH/g) | 14.4 | 15.5 | 16.3 | 15.3 |
| Turbidity (NTU) | 5.1 | 5.4 | 5.3 | 4.2 |
| Results | | | | |
| Filtration | medium | slow | slow | slow |
| Efficiency of incorporation of Ca | 99.4 | 99.3 | 97.0 | 93.7 |
| Calcium hydroxide carbonation (%, calculated) | 93.6 | 93.4 | 93.3 | 94 |
| Calcium isostearate (wt %, calculated) | 23.2 | 23.4 | 23.1 | 23.1 |
| Calcium salts of the calixarene product (wt %, calculated) | 23.0 | 22.9 | 10.2 | 4.0 |
| Total soap content (wt %, calculated) | 46.2 | 46.3 | 33.3 | 27.1 |

Examples 28-30: Preparation of Detergent Compositions with Lower Soap Content and TBN=300, Comprising Overbased Calcium Compounds of Calixarenes Examples 28 to 30 relate to the preparation of detergent compositions with a TBN value of about 300 mg KOH/g and lower soap content than in the detergent compositions of examples 24 to 27. The detergent compositions in examples 28 to 30 were prepared using calixarene and isostearic acid in a weight ratio of 1:1. The method of preparation used differs from that in examples 24 to 27 in a lower molar ratio used between carbon dioxide and calcium hydroxide in excess with respect to the salification reaction. This change leads to lower percentage carbonation of the available calcium hydroxide, giving products with high efficiency of incorporation of calcium.

In these examples the preparation reactions are carried out in equipment identical to that used in examples 24 to 27.

Example 28

The reactor described above is charged in a nitrogen atmosphere: 59.10 grams of the p-dodecyl calix[5,6,8]arene mixed with linear oligomers fully functionalized with hydroxycarbonyl-methoxy groups of example 3 (MW=339.1 per repeating unit, 53 wt % in xylene, 0.092 mol), 31.38 grams of isostearic acid (0.110 mol) and 82.97 grams of SN 150 base oil.

The mixture is heated with stirring (500 rev/min) at a temperature of 80° C., it is left in these conditions for 15 minutes, and then it is heated to give a temperature inside the reactor of 130° C. Then the xylene is removed by flash distillation, cutting off the nitrogen and gradually lowering the pressure to about 20 mbar. 27.7 g of xylene is collected. The vacuum is broken, the nitrogen atmosphere is restored and 38.28 g of calcium hydroxide (titre 96% w/w, 0.517 mol) is added via a charging funnel at a temperature of 130° C., in the space of about 5 minutes. While stirring, 107.60 grams of 2-ethylhexanol is then added from the same charging funnel.

The nitrogen is cut off and vacuum is applied, gradually lowering the pressure until it is 150 mbar. It is left in these conditions for 15 minutes. The vacuum is broken, the nitrogen atmosphere is restored and 15.68 grams of ethylene glycol is added, by dropping funnel, in about 5 minutes.

The nitrogen is cut off and vacuum is applied, gradually lowering the pressure to 70 mbar. It is left in these conditions for 90 minutes, during which the 2-ethylhexanol-water azeotrope is distilled and is collected in the Dean-Stark condenser, where the water, which also contains small amounts of ethylene glycol, is separated from the 2-ethylhexanol.

The vacuum is broken, the nitrogen atmosphere is restored and 11.36 grams of ethylene glycol is added at a temperature of 130° C., by dropping funnel.

Then 15.5 grams of carbon dioxide (0.352 mol) is added at a temperature of 130° C. in 90 minutes, stirring the mixture at 750 rev/min.

At the end of adding the carbon dioxide, the stirring speed is reduced to 500 rev/min, the pressure is gradually lowered to 70 mbar and then the mixture is heated from 130° C. to 200° C., programming the temperature rise of the thermostatic bath from 1400° C. to 210° C. in 70 minutes (1° C. per minute). During this step the solvent is removed by flash distillation and is collected in a flask connected to the Dean-Stark condenser.

Once a temperature of 200° C. is reached, the pressure is further reduced to below 10 mbar and these conditions are maintained for 60 minutes to remove the greater part of the residual solvent from the product. Then the reaction mixture is cooled to 160° C., the vacuum is broken and the nitrogen atmosphere is restored.

An amount of filter aid equal to 6 grams is added to the stirred mixture at a temperature of 160° C., and after mixing for 15 minutes it is filtered on a 0.4-litre jacketed steel filter, having a filtering surface consisting of an 80-mesh steel screen. Prior to filtration, a layer of filtering earth is prepared on the filter. Filtration is carried out at a temperature of 160° C. and with a pressure of 5 atmospheres of nitrogen.

A medium filtration rate was obtained.

The total amount of product, including that recovered after washing the filter with solvent, is 190 grams.

The product after filtration has the following characteristics:
Calcium content: 10.88 wt %
Viscosity at 100° C.: 80.4 cSt
TBN: 304.5 mg KOH/g
Free alkalinity: 35.8 mg KOH/g
Turbidity (5% solution in SN 150): 3 NTU (nephelometric turbidity units)

Based on the results obtained, it is possible to calculate the efficiency of incorporation of calcium into the detergent composition. Moreover, taking into account that the free alkalinity corresponds to the content of free calcium hydroxide and that isostearic acid and the calixarene used in this example (fully functionalized with carboxylic acid groups) are salified completely, it is possible to calculate the percentage carbonation of the calcium hydroxide in excess with respect to the salification reaction, the content of calcium isostearate, of calcium salts of the calixarene product and the total content of organic calcium salts (total soap).
Efficiency of calcium incorporation=99.8%
Calcium hydroxide carbonation=85.4%
Calcium isostearate=17.6 wt %
Calcium salts of the calixarene product=17.4 wt %
Total soap content=35 wt %

Example 29

The method of preparation used is the same as in example 28. The p-dodecyl calix[5,6,8]arene+linear oligomers 33% functionalized with hydroxycarbonyl-methoxy groups from example 5 and isostearic acid were used in this example. The amounts of reactants and of solvents used are as follows:
Calixarene example 5 (MW=300.2 per repeating unit, 53.5 wt % in xylene, 0.104 mol): 58.32 grams,
Isostearic acid (0.110 mol): 31.28 grams,
SN 150 base oil: 83.39 grams,
Calcium hydroxide (0.517 mol): 38.28 grams,
2-Ethylhexanol: 107.2 grams,
Ethylene glycol (1st addition): 15.63 grams,
Ethylene glycol (2nd addition): 11.32 grams,
Carbon dioxide: (0.352 mol): 15.5 grams At the beginning of the preparation procedure, 27.1 grams of xylene is removed by distillation.

The filtration rate was found to be low.

The total amount of product, including that recovered after washing the filter with solvent, is 190.5 grams.

The product after filtration has the following characteristics:
Calcium content: 10.79 wt %
Viscosity at 100° C.: 74.8 cSt
TBN: 303.6 mg KOH/g Free alkalinity: 35.8 mg KOH/g
Turbidity (5% solution in SN 150): 3.1 NTU (nephelometric turbidity units)

Based on the results obtained, it is possible to calculate the efficiency of incorporation of calcium into the detergent composition. Moreover, taking into account that the free alkalinity corresponds to the content of free calcium hydroxide, that the isostearic acid is fully salified by the calcium hydroxide and that the calixarene used in this example (partially functionalized with carboxylic acid groups) is fully salified with respect to the carboxyl moiety, but partially for the phenolic moiety (17.1%, as in example 12), it is possible to calculate the percentage carbonation of the calcium hydroxide in excess with respect to the salification reaction, the content of calcium isostearate, of calcium salts of the calixarene product and the total content of organic calcium salts (total soap).
Efficiency of calcium incorporation=99.2%
Calcium hydroxide carbonation=86.2%
Calcium isostearate=17.5 wt %
Calcium salts of the calixarene product=7.7 wt %
Total soap content=25.2 wt %

Comparative Example 30

The method of preparation used is the same as in example 28. The p-dodecyl calix[5,6,8]arene mixed with linear oligomers from example 1 and isostearic acid were used in this example. The amounts of reactants and of solvents used are as follows:
Calixarene example 1 (MW=281.1 per repeating unit, 77.5 wt % in xylene, 0.111 mol): 40.20 grams,
Isostearic acid (0.110 mol): 31.22 grams,
SN 150 base oil: 83.62 grams,
Calcium hydroxide (0.517 mol): 38.28 grams,
2-Ethylhexanol: 107.10 grams,
Ethylene glycol (1st addition): 15.60 grams,
Ethylene glycol (2nd addition): 11.30 grams,
Carbon dioxide: (0.352 mol): 15.5 grams At the beginning of the preparation procedure, 9 grams of xylene is removed by distillation.

The filtration rate was found to be low.

The total amount of product, including that recovered after washing the filter with solvent, is 190.2 grams.

The product after filtration has the following characteristics:
Calcium content: 10.59 wt %
Viscosity at 100° C.: 61.5 cSt
TBN: 299.3 mg KOH/g
Free alkalinity: 35.6 mg KOH/g
Turbidity (5% solution in SN 150): 2.9 NTU (nephelometric turbidity units)

Based on the results obtained, it is possible to calculate the efficiency of incorporation of calcium into the detergent composition. Moreover, taking into account that the free alkalinity corresponds to the content of free calcium hydroxide, that the isostearic acid is fully salified by the calcium hydroxide and that the calixarene used in this example is salified partially (17.1%, as in example 12), it is possible to calculate the percentage carbonation of the calcium hydroxide in excess with respect to the salification reaction, the content of calcium isostearate, of calcium salts of the calixarene product and the total content of organic calcium salts (total soap).
Efficiency of calcium incorporation=97.3%
Calcium hydroxide carbonation=86.7%
Calcium isostearate=17.5 wt %
Calcium salts of the calixarene product=3 wt %
Total soap content=20.5 wt %.

The results of examples 28 and 29, which use calixarene products functionalized with carboxylic acid groups, and of comparative example 30, which uses p-dodecyl calix[5,6,8.]arene mixed with linear oligomers, are given in Table 5.

In examples 28 to 30, relative to examples 24 to 27, the ratio of the amount of isostearic acid-calixarene mixture used, to the amount of base oil was reduced, with the aim of obtaining overbased detergent compositions with a lower soap content. These detergent compositions may be used in combination with detergent compositions with higher soap content and lower TBN value, for example such as the detergent composition of example 10, in the formulation of engine lubricants. The advantage of using the combination of detergent compositions, such as that in example 28 with that in example 10, relative to the use of a single detergent composition with high soap content, such as that in example 24, is that it allows greater flexibility in the formulation of lubricants with varying soap content and varying alkalinity.

Moreover, in examples 28 to 30, relative to examples 24 to 27, by using a lower molar ratio of carbon dioxide to calcium hydroxide in excess with respect to the salification reaction, in certain conditions of carbon dioxide feed rate it is possible to obtain lower values of percentage carbonation (about 86% in examples 28 to 30, relative to about 94% in examples 24 to 27). This procedure makes it possible to obtain stable products with a higher efficiency of incorporation of calcium, as formation of amorphous calcium carbonate predominates, which is incorporated in the micellar structure of the detergent composition, and the formation of crystalline calcium carbonate, which precipitates, is instead cancelled or at least limited considerably.

As expected, comparing the results of examples 28 and 29 with comparative example 30, with increase in the degree of functionalization of the calixarene with acid groups of carboxylic type, the content of calcium salts of the calixarene product and the total soap content in the detergent composition increase.

The efficiency of incorporation of calcium into the detergent composition is still better for the products derived from calixarenes functionalized with carboxylic acid groups relative to those that are unfunctionalized (compare examples 28 and 29 with comparative example 30).

TABLE 5

| Product | Example 28 | Example 29 | Comparative Example 30 |
| --- | --- | --- | --- |
| Calixarene | Example 3 | Example 5 | Example 1 |
| R1 | 100% | 33% | 100% |
|  | —CH$_2$COOH | —CH$_2$COOH | —H |
| R2 | —C$_{12}$H$_{25}$ | —C$_{12}$H$_{25}$ | —C$_{12}$H$_{25}$ |
| Alkyl carboxylic acid | Isostearic acid | Isostearic acid | Isostearic acid |
| Alkyl phenol | — | — | — |
| Product characteristics |  |  |  |
| Calcium content (wt %) | 10.88 | 10.79 | 10.59 |
| Viscosity at 100° C. (cSt) | 80.4 | 74.8 | 61.5 |
| TBN (mg KOH/g) | 304.5 | 303.6 | 299.3 |
| Free alkalinity (mg KOH/g) | 35.8 | 35.8 | 35.6 |
| Turbidity (NTU) | 3.0 | 3.1 | 2.9 |
| Results |  |  |  |
| Filtration | medium | slow | slow |
| Efficiency of incorporation of Ca (%) | 99.8 | 99.2 | 97.3 |

TABLE 5-continued

| Product | Example 28 | Example 29 | Comparative Example 30 |
|---|---|---|---|
| Calcium hydroxide carbonation (%) | 85.4 | 86.2 | 86.7 |
| Calcium isostearate (wt %, calculated) | 17.6 | 17.5 | 17.5 |
| Calcium salts of the calixarene product (wt %, calculated) | 17.4 | 7.7 | 3.0 |
| Total soap content (wt %, calculated) | 35.0 | 25.2 | 20.5 |

Examples 31-32: Preparation of Detergent Compositions with TBN=400, Comprising Overbased Calcium Compounds of Calixarenes Examples 31 and 32 relate to the preparation of detergent compositions with a TBN value of about 400 mg KOH/g. The detergent composition of example 31 was prepared using calixarene and isostearic acid in a weight ratio of 1:1. The detergent composition of example 32 was instead prepared using calixarene, isostearic acid and dodecylphenol respectively in weight ratio of 1:0.5:0.5. The method of preparation used is similar to that used in examples 28 to 30.

The preparation reactions were carried out in equipment identical to that used in examples 28 to 30.

Example 31

The reactor described above is charged in a nitrogen atmosphere: 55.99 grams of the p-dodecyl calix[5,6,8]arene mixed with linear oligomers fully functionalized with hydroxycarbonyl-methoxy groups of example 3 (MW=339.1 per repeating unit, 53 wt % in xylene, 0.088 mol), 29.73 grams of isostearic acid (0.105 mol) and 62.90 grams of SN 150 base oil.

The mixture is heated with stirring (500 rev/min) to a temperature of 80° C., it is left in these conditions for 15 minutes, and then it is heated to give a temperature inside the reactor of 130° C. Then the xylene is removed by flash distillation, cutting off the nitrogen and gradually lowering the pressure to about 20 mbar. 26.1 g of xylene is collected. The vacuum is broken, the nitrogen atmosphere is restored, and 48.74 g of calcium hydroxide (0.658 mol) is added via a charging funnel at a temperature of 130° C., in the space of about 5 minutes. While stirring, 102.5 grams of 2-ethylhexanol is then added from the same charging funnel.

The nitrogen is cut off and vacuum is applied, gradually lowering the pressure until it is 150 mbar. It is left in these conditions for 15 minutes. The vacuum is broken, the nitrogen atmosphere is restored and 14.86 grams of ethylene glycol is added by dropping funnel in about 5 minutes.

The nitrogen is cut off and vacuum is applied, gradually lowering the pressure to 70 mbar. It is left in these conditions for 90 minutes, during which the 2-ethylhexanol-water azeotrope is distilled and is collected in the Dean-Stark condenser, where the water, which also contains small amounts of ethylene glycol, is separated from the 2-ethylhexanol.

The vacuum is broken, the nitrogen atmosphere is restored and 10.76 grams of ethylene glycol is added at a temperature of 130° C., by dropping funnel.

Then 20.1 grams of carbon dioxide (0.457 mol) is added at a temperature of 130° C. in 120 minutes, stirring the mixture at 750 rev/min.

At the end of adding the carbon dioxide, the stirring speed is reduced to 500 rev/min, the pressure is gradually lowered to 70 mbar and then the mixture is heated from 1300° C. to 200° C., programming the temperature rise of the thermostatic bath from 140° C. to 210° C. in 70 minutes (1° C. per minute). During this step the solvent is removed by flash distillation and is collected in a flask connected to the Dean-Stark condenser.

Once a temperature of 200° C. is reached, the pressure is further reduced to below 10 mbar and these conditions are maintained for 60 minutes to remove the greater part of the residual solvent from the product. Then the reaction mixture is cooled to 70° C., the vacuum is broken and the nitrogen atmosphere is restored.

180 grams of 2-ethylhexanol is added to the crude product in the reactor, the mixture is stirred, and it is then discharged from the reactor and centrifuged for 20 minutes with a laboratory centrifuge at room temperature and at a speed of 2000 rpm. The liquid phase is separate and heated to a temperature of 100° C. and an amount of filter aid equal to 6 grams is added to it. After mixing for 15 minutes it is filtered on a 0.4-litre jacketed steel filter, having a filtering surface consisting of an 80-mesh steel screen. Prior to filtration, a layer of filtering earth is prepared on the filter. Filtration is carried out at a temperature of 100° C. and with a pressure of 5 atmospheres of nitrogen.

A medium filtration rate was obtained.

The mixture is then transferred to the reactor and is heated to a temperature of 200° C., gradually reducing the pressure below 10 mbar and leaving it in these conditions for about 1 hour, to remove the solvent by distillation.

The amount of product obtained is 179.5 grams.

The product thus obtained has the following characteristics:
Calcium content: 14.45 wt %
Viscosity at 100° C.: 237.5 cSt
TBN: 404.5 mg KOH/g
Free alkalinity: 52.2 mg KOH/g
Turbidity (5% solution in SN 150): 7 NTU (nephelometric turbidity units)

Based on the results obtained and taking into account that the free alkalinity corresponds to the content of free calcium hydroxide, it is possible to calculate the efficiency of incorporation of calcium into the detergent composition and the percentage carbonation of the calcium hydroxide in excess with respect to the salification reaction.
Efficiency of calcium incorporation=98.3%
Calcium hydroxide carbonation=85%

Example 32

The reactor described above is charged in a nitrogen atmosphere: 55.91 grams of the p-dodecyl calix[5,6,8]arene mixed with linear oligomers fully functionalized with hydroxycarbonyl-methoxy groups of example 3 (MW=339.1 per repeating unit, 53 wt % in xylene, 0.089 mol), 14.83 grams of isostearic acid (0.052 mol), 14.83 grams of p-dodecylphenol (0.057 mol) and 63.11 grams of SN 150 base oil.

The mixture is heated with stirring (500 rev/min) at a temperature of 80° C., it is left in these conditions for 15 minutes, and then it is heated to give a temperature inside the reactor of 130° C. Then the xylene is removed by flash distillation, cutting off the nitrogen and gradually lowering the pressure to about 20 mbar. 26.2 g of xylene is collected. The vacuum is broken, the nitrogen atmosphere is restored, and 48.74 g of calcium hydroxide (0.658 mol) is added via a charging funnel at a temperature of 130° C., in the space of about 5 minutes. While stirring, 102.4 grams of 2-ethylhexanol is then added from the same charging funnel.

The nitrogen is cut off and vacuum is applied, gradually lowering the pressure until it is 150 mbar. It is left in these conditions for 15 minutes. The vacuum is broken, the nitrogen atmosphere is restored and 14.83 grams of ethylene glycol is added by dropping funnel in about 5 minutes.

The nitrogen is cut off and vacuum is applied, gradually lowering the pressure to 70 mbar. It is left in these conditions for 90 minutes, during which the 2-ethylhexanol-water azeotrope is distilled, and is collected in the Dean-Stark condenser, where the water, which also contains small amounts of ethylene glycol, is separated from the 2-ethylhexanol.

The vacuum is broken, the nitrogen atmosphere is restored and 10.74 grams of ethylene glycol is added at a temperature of 130° C., by dropping funnel.

Then 20.1 grams of carbon dioxide (0.457 mol) is added at a temperature of 130° C. in 120 minutes, stirring the mixture at 750 rev/min.

At the end of adding the carbon dioxide, the stirring speed is reduced to 500 rev/min, the pressure is gradually lowered to 70 mbar and then the mixture is heated from 130° C. to 200° C., programming the temperature rise of the thermostatic bath from 140° C. to 210° C. in 70 minutes (1° C. per minute). During this step the solvent is removed by flash distillation and is collected in a flask connected to the Dean-Stark condenser.

Once a temperature of 200° C. is reached, the pressure is further reduced to below 10 mbar and these conditions are maintained for 60 minutes to remove the greater part of the residual solvent from the product.

180 grams of xylene is added to the crude product in the reactor, the mixture is stirred, and then is discharged from the reactor and centrifuged for 20 minutes with a laboratory centrifuge at room temperature and at a speed of 2000 rpm. The liquid phase is separated and heated to a temperature of 80° C. and an amount of filter aid equal to 6 grams is added to it. After mixing for 15 minutes it is filtered on a 0.4-litre jacketed steel filter, having a filtering surface consisting of an 80-mesh steel screen. Prior to filtration, a layer of filtering earth is prepared on the filter. Filtration is carried out at a temperature of 80° C. and with a pressure of 5 atmospheres of nitrogen.

A medium filtration rate was obtained.

The mixture is then transferred to the reactor and is heated to a temperature of 200° C., gradually reducing the pressure to below 10 mbar and leaving it in these conditions for about 1 hour, to remove the solvent by distillation.

The amount of product obtained is 179.1 grams.

The product thus obtained has the following characteristics:
Calcium content: 14.42 wt %
Viscosity at 100° C.: 369.5 cSt
TBN: 403.6 mg KOH/g
Free alkalinity: 55.3 mg KOH/g
Turbidity (5% solution in SN 150): 5 NTU (nephelometric turbidity units)

Based on the results obtained and taking into account that the free alkalinity corresponds to the content of free calcium hydroxide, it is possible to calculate the efficiency of incorporation of calcium into the detergent composition and the percentage carbonation of the calcium hydroxide in excess with respect to the salification reaction.
Efficiency of calcium incorporation=97.9%
Calcium hydroxide carbonation=84.2%

The results of examples 31 and 32 are given in Table 5 bis.

Examples 31 and 32 were carried out using ratios of acid mixture to base oil and molar ratios of carbon dioxide to unreacted calcium hydroxide similar to those in examples 29 to 30. Working in certain conditions of carbon dioxide feed rate, it was possible to obtain values of percentage carbonation of the unreacted calcium hydroxide of about 85%, which made it possible to obtain stable products with high efficiency of incorporation of calcium.

The results of examples 31 and 32 demonstrate that it is possible to obtain, using the calixarene fully functionalized with carboxylic acid groups, detergent compositions with high alkalinity (TBN greater than 400 mg KOH/g), maintaining excellent efficiency of incorporation of calcium.

In the preparation of the detergent compositions of examples 31 and 32, to ensure a good filtration rate, the product, after dilution in a suitable solvent, is centrifuged and then filtered using a filter aid.

TABLE 5 bis

| Product | Example 31 | Example 32 |
|---|---|---|
| Calixarene | Example 3 | Example 3 |
| R1 | 100% | 100% |
|  | —$CH_2COOH$ | —$CH_2COOH$ |
| R2 | —$C_{12}H_{25}$ | —$C_{12}H_{25}$ |
| Alkyl carboxylic acid | Isostearic acid | Isostearic acid |
| Alkyl phenol | — | p-dodecyl phenol |
| Product characteristics |  |  |
| Calcium content (wt %) | 14.46 | 14.42 |
| Viscosity at 100° C. (cSt) | 237.5 | 369.5 |
| TBN (mg KOH/g) | 404.5 | 403.6 |
| Free alkalinity (mg KOH/g) | 52.2 | 55.3 |
| Turbidity (NTU) | 7.5 | 5.0 |
| Results |  |  |
| Filtration | medium after centrifugation | medium after centrifugation |
| Efficiency of incorporation of Ca (%) | 98.3 | 97.9 |
| Calcium hydroxide carbonation (%) | 85 | 84.2 |

Examples 33-66: Lubricant Formulations

Using the detergent compositions of examples 13 to 27, the corresponding additive packages were prepared (examples 33 to 47), which contain said detergent compositions at a concentration, expressed as the percentage by weight of said detergent compositions based on the weight of the additive package, of 10.3%.

The package of comparative example 48 was also prepared, comprising conventional detergents containing sulfur and in particular containing a combination of a commercial detergent with low alkalinity based on calcium alkylbenzenesulfonate (eni MX 3280: TBN=24 mgKOH/g, calcium=2.8 wt %, calcium sulfonate=49 wt %) with a commercial overbased detergent based on calcium alkylbenzenesulfonate (eni MX 3245: TBN=308 mgKOH/g, calcium=12 wt %, calcium sulfonate=27 wt %).

Finally, a package was prepared (example 49) comprising a combination of the neutral detergent composition of example 10 with the overbased one of example 28, used at concentrations such as to give a TBN value and a content of organic calcium salts (soap) very similar to those of the package containing sulfonate detergents of comparative example 48 and those of the packages of examples 33 and 34. The total content of organic calcium salts of the package of example 49, as the sum of those of the calixarene compounds and of the calcium alkylcarboxylate, is very similar to that of the packages 33 and 34 and of all the other packages that contain detergents derived from calixarenes fully functionalized with carboxylic acid groups (examples 38, 39, 40, 41, 44 and 45). Compared to all the other packages mentioned, that of example 49 is the one that has the highest content of calcium salts of calixarene compounds.

The packages in examples 33 to 49 contain, besides the detergent additives, other additives, which are the same and at the same concentration for all the packages. These additives are: dispersants, antioxidants, antiwear additives, friction modifiers and foam inhibitors. The packages of examples 33 to 49 also contain SN 150 lubricant base oil, which is at the same concentration in the packages of examples 33 to 47, which contain the same concentration of detergent additive, whereas it is at a lower concentration in packages 48 and 49, which contain a higher concentration of detergent.

The following parameters of the additive packages were determined:
Kinematic viscosity at 100° C. (method ASTM D 445);
Total base number (TBN) (method ASTM D 2897);
Calcium content (method ASTM D 4951)

The results of characterization of the packages relating to examples 33, 34, 35 and of comparative examples 36 and 37 are given in Table 6. These packages were formulated using, respectively, the detergent compositions with TBN of about 250 mg KOH/g of examples 13, 14, 15 and of comparative examples 16 and 17.

The results of characterization of the packages relating to examples 38, 39, 40, 41, 42 and comparative example 43 are given in Table 7. These packages were formulated using respectively the detergent compositions with TBN of about 300 mg KOH/g and above of examples 18, 19, 20, 21, 22 and of comparative example 23.

The results of characterization of the packages relating to examples 44, 45, 46 and of comparative example 47 are given in Table 8. These packages were formulated using respectively the detergent compositions with TBN of about 300 mg KOH/g of examples 24, 25, 26 and of comparative example 27. Table 9 gives the results of characterization of the package of comparative example 48, comprising conventional detergents based on calcium sulfonates and of the package of example 49, comprising a combination of the detergent compositions of examples 10 and 28.

Using the packages of examples 33 to 49, the corresponding engine lubricant formulations with SAE 5W-30 viscosity grade were prepared (examples 50 to 66), which have the following composition, expressed as percentage by weight relative to the lubricant formulation:
base oils: 78.8 wt %;
additive package: 16 wt %;
viscosity index improver: 5 wt %;
pour point depressant: 0.2 wt %.

All the lubricant formulations (examples 50 to 66) contain the same base oils, the same viscosity index improver and the same pour point depressant.

The following parameters of the lubricating oils were determined:
Kinematic viscosity at 100° C. (method ASTM D 445);
Kinematic viscosity at 40° C. (method ASTM D 445);
Viscosity index (method ASTM D 2270);
Total base number (TBN) (ASTM D 2897);
Calcium content (method ASTM D 4951)
High-temperature deposits (TEOST MHT) (method ASTM D 7097);
Resistance to oxidation by differential scanning calorimetry DSC (method CEC L 85).

The results of evaluation of the lubricants of examples 50 to 66 are given in Tables 6, 7, 8 and 9.

TABLE 6

| Package: composition and properties | Example 33 | Example 34 | Example 35 | Comparative Example 36 | Comparative Example 37 |
|---|---|---|---|---|---|
| Detergent | Example 13 | Example 14 | Example 15 | Comparative Example 16 | Comparative Example 17 |
| Detergent (wt %) | 10.3 | 10.3 | 10.3 | 10.3 | 10.3 |
| Total base number (TBN, mgKOH/g)(1) | 52.8 | 53.3 | 53.3 | 53.3 | 53.1 |
| Kinematic viscosity at 100° C. (cSt) | 61.1 | 61.3 | 60.6 | 51.3 | 55.9 |
| Calcium content (wt %) | 0.91 | 0.93 | 0.93 | 0.93 | 0.93 |
| Soap from detergents (calculated, wt %) | 4.75 | 4.75 | 4.11 | 3.41 | 3.47 |
| Calcium stearate (calculated, wt %) | 3.20 | 3.21 | 3.20 | 3.15 | 3.20 |
| Calcium salts of calixarenes (calculated, wt %) | 1.55 | 1.54 | 0.91 | 0.26 | 0.27 |

| 5W-30 lubricating oil: Composition and properties | Example 50 | Example 51 | Example 52 | Comparative Example 53 | Comparative Example 54 |
|---|---|---|---|---|---|
| Base oils (wt %) | 78.8 | 78.8 | 78.8 | 78.8 | 78.8 |
| Additive package (wt %) | 16.0 | 16.0 | 16.0 | 16.0 | 16.0 |
| Viscosity index improver (wt %) | 5.0 | 5.0 | 5.0 | 5.0 | 5.0 |
| Pour Point Depressant (wt %) | 0.2 | 0.2 | 0.2 | 0.2 | 0.2 |
| Soap from detergents (calculated, wt %) | 0.76 | 0.76 | 0.66 | 0.55 | 0.56 |
| Calcium salts of calixarenes (calculated, % weight) | 0.25 | 0.25 | 0.15 | 0.04 | 0.04 |
| Kinematic viscosity at 40° C. (cSt) | 71.14 | 71.01 | 71.31 | 69.50 | 70.61 |
| Kinematic viscosity at 100° C. (cSt) | 11.32 | 11.35 | 11.30 | 11.12 | 11.21 |
| Viscosity index | 153 | 154 | 153 | 153 | 152 |
| Total base number (TBN, mgKOH/g) | 8.40 | 8.50 | 8.50 | 8.50 | 8.50 |
| Calcium content (wt %) | 0.145 | 0.148 | 0.147 | 0.149 | 0.148 |
| Total deposits TEOST MHT (mg) | 8.7 | 8.3 | 11.2 | 15.7 | 15.2 |
| Resistance to oxidation by means of DSC (onset, min) | 95 | 93 | 94 | 101 | 100 |

(1)Besides the detergents, other types of additives present in the package contribute to the TBN value.

TABLE 7

| Package: composition and properties | Example 38 | Example 39 | Example 40 | Example 41 | Example 42 | Comparative Example 43 |
|---|---|---|---|---|---|---|
| Detergent | Example 18 | Example 19 | Example 20 | Example 21 | Example 22 | Comparative Example 23 |
| Detergent (wt %) | 10.3 | 10.3 | 10.3 | 10.3 | 10.3 | 10.3 |
| Total base number (TBN, mgKOH/g) (1) | 59.1 | 59.0 | 60.2 | 61.3 | 59.0 | 57.9 |
| Kinematic viscosity at 100° C. (cSt) | 133.3 | 96.8 | 89.0 | 103.9 | 135.5 | 99.7 |
| Calcium content (wt %) | 1.14 | 1.14 | 1.18 | 1.22 | 1.13 | 1.08 |
| Soap from detergents (calculated, wt %) | 4.91 | 4.92 | 4.85 | 4.79 | 3.85 | 3.56 |
| Calcium stearate (calculated, wt %) | 3.31 | — | — | — | — | 3.28 |
| Calcium isostearate (calculated, wt %) | — | 3.32 | 3.29 | 2.40 | 2.42 | — |
| Calcium salts of calixarenes (calculated, wt %) | 1.60 | 1.60 | 1.56 | 2.39 | 1.43 | 0.28 |

| 5W-30 lubricating oil: Composition and properties | Example 55 | Example 56 | Example 57 | Example 58 | Example 59 | Comparative Example 60 |
|---|---|---|---|---|---|---|
| Base oils (wt %) | 78.8 | 78.8 | 78.8 | 78.8 | 78.8 | 78.8 |
| Additive package (wt %) | 16.0 | 16.0 | 16.0 | 16.0 | 16.0 | 16.0 |
| Viscosity index improver (wt %) | 5.0 | 5.0 | 5.0 | 5.0 | 5.0 | 5.0 |
| Pour Point Depressant (wt %) | 0.2 | 0.2 | 0.2 | 0.2 | 0.2 | 0.2 |
| Soap from detergents (calculated, wt %) | 0.79 | 0.79 | 0.78 | 0.77 | 0.62 | 0.57 |
| Calcium salts of calixarenes (calculated, wt %) | 0.26 | 0.26 | 0.25 | 0.38 | 0.23 | 0.04 |
| Kinematic viscosity at 40° C. (cSt) | 79.62 | 75.95 | 75.40 | 76.21 | 79.82 | 76.20 |
| Kinematic viscosity at 100° C. (cSt) | 12.28 | 11.90 | 11.79 | 11.98 | 12.30 | 11.93 |
| Viscosity index | 152 | 153 | 153 | 154 | 152 | 153 |
| Total base number (TBN, mgKOH/g) | 9.5 | 9.4 | 9.6 | 9.8 | 9.4 | 9.3 |
| Calcium content (wt %) | 0.182 | 0.183 | 0.188 | 0.194 | 0.182 | 0.174 |
| Total deposits TEOST MHT (mg) | 6.8 | 6.9 | 6.4 | 4.5 | 7.1 | 13.9 |
| Resistance to oxidation by means of DSC (onset, min) | 92 | 93 | 92 | 91 | 100 | 101 |

(1) Besides the detergents, other types of additives present in the package contribute to the TBN value.

TABLE 8

| Package: composition and properties | Example 44 | Example 45 | Example 46 | Comparative Example 47 |
|---|---|---|---|---|
| Detergent | Example 24 | Example 25 | Example 26 | Comparative Example 27 |
| Detergent (wt %) | 10.3 | 10.3 | 10.3 | 10.3 |
| Total base number (TBN, mgKOH/g)(1) | 58.5 | 58.5 | 57.8 | 57.1 |
| Kinematic viscosity at 100° C. (cSt) | 78.5 | 79.1 | 78.4 | 60.1 |
| Calcium content (wt %) | 1.12 | 1.12 | 1.09 | 1.06 |
| Soap from detergents (calculated, wt %) | 4.76 | 4.77 | 3.43 | 2.79 |
| Calcium isostearate (calculated, wt %) | 2.39 | 2.43 | 2.38 | 2.38 |
| Calcium salts of calixarenes (calculated, wt %) | 2.37 | 2.36 | 1.05 | 0.41 |

| 5W-30 lubricating oil: Composition and properties | Example 61 | Example 62 | Example 63 | Comparative Example 64 |
|---|---|---|---|---|
| Base oils (wt %) | 78.8 | 78.8 | 78.8 | 78.8 |
| Additive package (wt %) | 16.0 | 16.0 | 16.0 | 16.0 |
| Viscosity index improver (wt %) | 5.0 | 5.0 | 5.0 | 5.0 |
| Pour Point Depressant (wt %) | 0.2 | 0.2 | 0.2 | 0.2 |
| Soap from detergents (calculated, wt %) | 0.76 | 0.76 | 0.55 | 0.45 |
| Calcium salts of calixarenes (calculated, wt %) | 0.38 | 0.38 | 0.17 | 0.07 |
| Kinematic viscosity at 40° C. (cSt) | 74.23 | 74.29 | 73.64 | 71.43 |
| Kinematic viscosity at 100° C. (cSt) | 11.64 | 11.65 | 11.62 | 11.31 |
| Viscosity index | 152 | 152 | 153 | 153 |
| Total base number (TBN, mgKOH/g) | 9.40 | 9.40 | 9.30 | 9.10 |
| Calcium content (wt %) | 0.178 | 0.170 | 0.175 | 0.168 |
| Total deposits TEOST MHT (mg) | 4.6 | 4.3 | 8.4 | 18.1 |
| Resistance to oxidation by means of DSC (onset, min) | 92 | 94 | 100 | 101 |

(1)Besides the detergents, other types of additives present in the package contribute to the TBN value.

TABLE 9

| Package: composition and properties | Comparative Example 48 | Example 49 |
|---|---|---|
| Detergents | eni MX3245 + eni MX3280 | Example 28 (7 wt %) + Example 10 (4.5 wt %) |
| Total detergent (wt %) | 13.1 | 11.5 |
| Total base number (TBN, mgKOH/g)(1) | 51.6 | 52.1 |
| Kinematic viscosity at 100° C. (cSt) | 99.3 | 118.0 |
| Calcium content (wt %) | 1.02 | 0.86 |
| Soap from detergents (calculated, wt %) | 4.78 | 4.77 |
| Calcium isostearate (calculated, wt %) | — | 1.23 |
| Calcium salts of calixarenes (calculated, wt %) | — | 3.54 |
| 5W-30 lubricating oil: Composition and properties | Comparative Example 65 | Example 66 |
| Base oils (wt %) | 78.8 | 78.8 |
| Additive package (wt %) | 16.0 | 16.0 |
| Viscosity index improver (wt %) | 5.0 | 5.0 |
| Pour Point Depressant (wt %) | 0.2 | 0.2 |
| Soap from detergents (calculated, wt %) | 0.76 | 0.76 |
| Calcium salts of calixarenes (calculated, wt %) | — | 0.57 |
| Kinematic viscosity at 40° C. (cSt) | 76.23 | 77.54 |
| Kinematic viscosity at 100° C. (cSt) | 11.93 | 12.14 |
| Viscosity index | 153 | 154 |
| Total base number (TBN, mgKOH/g) | 8.2 | 8.3 |
| Calcium content (wt %) | 0.162 | 0.138 |
| Total deposits TEOST MHT (mg) | 19.2 | 3.8 |
| Resistance to oxidation by means of DSC (onset, min) | 99 | 93 |

(1)Besides the detergents, other types of additives present in the package contribute to the TBN value.

It can be seen from the results given in Tables 6, 7, 8 and 9 that the lubricant formulations containing the detergent composition of the present invention, comprising calcium salts of calixarenes partially or fully functionalized with acid groups of carboxylic type, have better detergent properties relative to the lubricant compositions formulated with the calixarene detergents of the prior art and relative to that formulated with the conventional sulfur-containing detergents based on calcium alkylbenzenesulfonates. This behaviour was determined with TEOST MHT (Thermo-Oxidation Engine Oil Simulation Test), which is used for evaluating the engine oil's capacity for controlling the formation of deposits at medium-high temperatures. This method consists of determining the weight of the deposits formed as a result of circulating, in oxidizing conditions (air flow), for a time of 24 hours, a sample of oil containing a small amount of organometallic catalyst through a special electrically heated rod at a controlled temperature of 285° C. The total deposit is determined as the sum of the deposit formed on the rod and of that collected on a filter as a result of washing the rod. In the text of method ASTM D 7097 it is stated that its validity, determined in interlaboratory tests, is in the range from 10 to 100 mg of total deposits, but that it may also be used in a wider range from 1 to 150 mg of total deposits.

The lubricant formulations containing the detergent compositions of the invention give less formation of deposits compared to the formulations containing the calixarene detergents of the prior art and compared to those formulated with the detergents based on calcium sulfonates.

The better performance of the lubricant formulations comprising the detergents of the invention compared to those containing the calixarene detergents of the prior art is mainly due to a higher content of calcium salts of organic acids (soap) and in particular a higher content of calcium salts of the calixarene compounds.

Moreover, in the lubricating oils comprising the detergent compositions of the invention, at equal soap content, which is given by the calcium salts of the calixarenes and by those of the alkyl carboxylic acids, formation of deposits decreases with increase in the content of calcium salts of the calixarenes.

In fact it can be seen from Table 6, which gives the results of evaluations of the lubricant compositions having a value of TBN=8.4-8.5 mg KOH/g, that the lubricant formulations containing the detergent compositions of the invention (examples 50 to 52) give, in the TEOST MHT test, less formation of deposits compared to the lubricant formulations comprising the calixarene detergents of the prior art (comparative examples 53 and 54). Moreover, the amount of deposits formed decreases with increase in the degree of functionalization with carboxylic acid groups of the calixarenes used in the process for preparing the detergent compositions contained in the lubricant formulations.

The resistance to oxidation, determined by differential scanning calorimetry DSC, is excellent for all the lubricants of Table 6.

Regarding the results of evaluation of the lubricant formulations of Table 7, having a TBN value in the range between 9.3 and 9.8 mgKOH/g, the same remarks may be made as were made regarding the lubricant formulations of Table 6, and it may also be added, from comparison of the results of example 57 with those of example 58, that at equal TBN and content of soap derived from the detergents, which is given by the sum of the content of calcium salts of the calixarene compounds and of isostearic acid, the formation of deposits in TEOST tends to decrease with increase in the content of calcium salts of the calixarenes.

The results of evaluation of the lubricants in Table 8 (examples 61 to 63 and comparative example 64) confirm what was stated above, whereas it can be seen from the results in Table 9 that the lubricating oil of example 66, containing a high level of calcium salts of calixarene compounds, shows excellent results in the TEOST, in terms of control of the formation of deposits. These results are better than those of the lubricant formulations (examples 50 and 51), that have similar values of TBN and soap content of the formulation of example 66, but in particular better than those of the lubricant formulation of comparative example 65, which contains conventional detergents based on calcium sulfonates.

The invention claimed is:

1. A metal compound of calixarene not containing sulfur and dispersible in oil, which can be partially salified, or neutral, or basic or overbased, said calixarene having general formula (I)

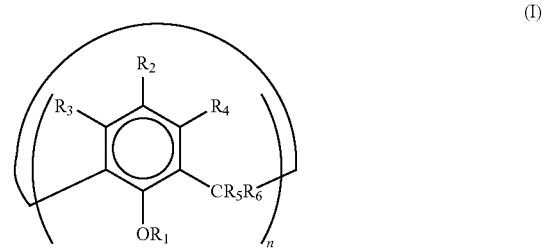

(I)

in which:
a) $R_1$, $R_2$, $R_3$ and $R_4$ are independently selected from hydrogen, or a group containing carbon and hydrogen, or a group containing in addition to carbon and hydrogen also a heteroatom, provided that said heteroatom is not sulfur;

b) one of the two substituents $R_5$ and $R_6$ is hydrogen, while the other may be selected from hydrogen, or a linear or branched alkyl with a number of carbon atoms between 1 and 6;

c) n is the number of units of the calixarene ring and is comprised in the range between 4 and 16;

wherein in at least one of the n units of the calixarene ring, at least one of the substituents $R_1$, $R_2$, $R_3$ and $R_4$ contains at least one acid group of carboxylic type available for reaction with a metal base, with the proviso that said acid group of carboxylic type is not contained in a unit of the calixarene ring derived from salicylic acid.

2. The metal compound according to claim 1 wherein the calixarene having general formula (I) comprises at least two units of the n units of the calixarene ring in which at least one of the substituents $R_1$, $R_2$, $R_3$ and $R_4$ contains at least one acid group of the carboxylic type, with the proviso that said acid group of carboxylic type is not part of a unit of the calixarene ring derived from salicylic acid.

3. The metal compound according to claim 1 wherein the calixarene having general formula (I) comprises a number of units of the ring, between 2 and n, in which one of the substituents $R_1$ and $R_2$ contains an acid group of carboxylic type, with the proviso that said acid group of carboxylic type is not part of a unit of the calixarene ring derived from salicylic acid.

4. The metal compound according to claim 1 wherein $R_1$ is selected from hydrogen; or a linear or branched alkyl having a number of carbon atoms comprised between 1 and 40; or a group containing in addition to carbon and hydrogen also a heteroatom and having a number of carbon atoms comprised between 2 and 24 thereof, provided that said heteroatom is not sulfur, and wherein said group contains one or more acid groups of carboxylic type available for the reaction with a metal base.

5. The metal compound according to claim 1 wherein $R_2$ is selected from a linear or branched alkyl having a number of carbon atoms between 1 and 40; or a group containing in addition to carbon and hydrogen also a heteroatom and having a number of carbon atoms between 1 and 24, provided that said heteroatom is not sulfur, and wherein said group contains one or more acid groups of carboxylic type available for the reaction with a metal base.

6. The metal compound according to claim 1 wherein $R_3$, $R_4$, $R_5$ and $R_6$ are simultaneously hydrogen.

7. The metal compound according to claim 1 wherein the metal of the metal compound is selected from an alkali metal, an alkaline earth metal, and any other metal whose basic compound is capable of forming a salt with a calixarene.

8. The metal compound according to claim 7 wherein the metal is selected from calcium and magnesium.

9. The metal compound according to claim 7 wherein the metal content corresponds to a ratio between the metal equivalents and acid ones of the calixarene from which it is derived comprised between 0.2 and 15.

10. A detergent composition comprising the metal compound of calixarene according to claim 1.

11. The detergent composition according to claim 10 wherein the metal compound of calixarene is present at a concentration, expressed as the weight percentage of said metal compound of calixarene of formula (I) with respect to the detergent composition, comprised between 5% and 100%.

12. The detergent composition according to claim 10 which further comprises at least one metal compound of an organic acid compound selected from:

A. a metal compound, partially salified, neutral, basic or overbased of an oligomeric compound of formula (IV)

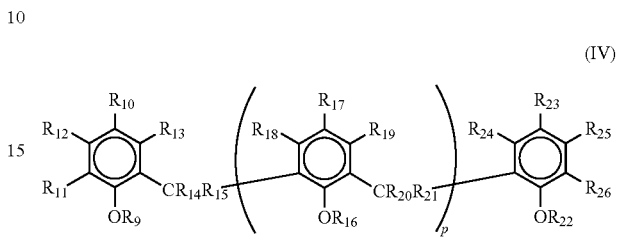

or of a monomeric compound of formula (V)

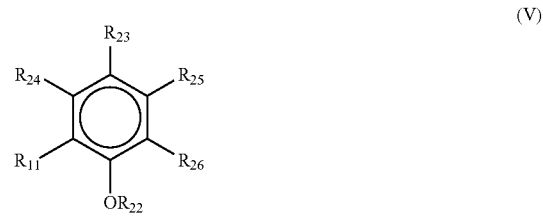

in which:

$R_9$, $R_{10}$, $R_{12}$, $R_{13}$, $R_{16}$, $R_{17}$, $R_{18}$, $R_{19}$, $R_{22}$, $R_{23}$, $R_{24}$ and $R_{25}$ are independently selected from hydrogen, a group containing carbon and hydrogen, a group containing in addition to carbon and hydrogen also a heteroatom, provided that sulfur is not present;

$R_{14}$, $R_{15}$, $R_{20}$ and $R_{21}$ are selected from hydrogen or an alkyl with a number of carbon atoms between 1 and 6;

$R_{11}$ and $R_{26}$ are independently selected from hydrogen, the hydroxymethylene group —$CH_2OH$, methyl and the hydroxycarbonyl group —COOH;

P is a number in the range between 0 and 20; or

B. a metal compound, partially salified, neutral, basic or overbased of a carboxylic, dicarboxylic and polycarboxylic acid containing a number of carbon atoms between 6 and 80, comprising an alkyl-carboxylic acid of formula (VI):

in which:

$R_{27}$ is selected from a linear or branched alkyl or alkenyl group, containing a number of carbon atoms between 6 and 40;

$R_{28}$ is selected from hydrogen, an alkyl group containing from 1 to 4 carbon atoms, or —$CH_2COOH$; or C. a metal compound, partially salified, neutral, basic or overbased of a compound of formula (VII):

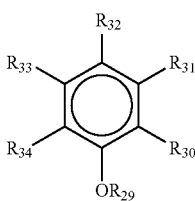

(VII)

in which $R_{29}$, $R_{30}$, $R_{31}$, $R_{32}$, $R_{33}$, and $R_{34}$ are independently selected from hydrogen, a group containing carbon and hydrogen, a group containing in addition to carbon and hydrogen also a heteroatom, provided that sulfur is not present; or D. a metal compound, partially salified, neutral, basic or overbased of a phenol substituted with a linear or branched alkyl group, in number comprised between 1 and 3, each containing a number of carbon atoms comprised between 2 and 40; or E. a metal compound, partially salified, neutral, basic or overbased of a salicylic acid substituted with a linear or branched alkyl group in number comprised between 1 and 3, each containing a number of carbon atoms comprised between 2 and 40; or F. a metal compound, partially salified, basic or overbased of calixarene of the general formula (Z) having substituents of hydroxyl type:

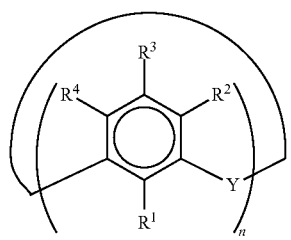

(Z)

in which Y is a divalent bridge group; $R_3$ is a group containing carbon and hydrogen, or a group containing in addition to carbon and hydrogen also a heteroatom; n is an integer between 3 and 9, and alternatively:

$R_1$ is hydroxyl and $R_2$ and $R_4$ are independently hydrogen, or a group containing carbon and hydrogen, or a group containing in addition to carbon and hydrogen also a heteroatom; or $R_2$ and $R_4$ are hydroxyl groups and $R_1$ is independently hydrogen, or a group containing carbon and hydrogen, or a group containing in addition to carbon and hydrogen also a heteroatom.

13. The detergent composition according to claim 10 which further comprises a lubricant base oil at a concentration, expressed as a percentage of the base oil with respect to the detergent composition, comprised between 10% and 90%.

14. A lubricant composition containing the detergent composition according to claim 10 and a lubricant base oil, or a mixture of lubricant base oils.

15. The lubricant composition according to claim 14, wherein the detergent composition is at a total concentration, expressed as percentage by weight of said detergent composition on the lubricant composition, comprised between 0.1% and 90%.

16. A process for the preparation of the detergent composition containing a metal compound of calixarene of general formula (I) partially salified, neutral or basic, according to claim 10, which comprises reacting, according to a salification reaction, a calixarene of the general formula (I) with a metal base in the presence of a reaction solvent or of a mixture of reaction solvents.

17. The process according to claim 16, wherein also an organic acid compound, or a mixture thereof, is present during the reaction of salification.

18. The process according to claim 16 wherein the salification reaction is conducted in the presence of a lubricant base oil or a mixture of lubricant base oils.

19. The process according to claim 16 wherein the amount of metal base used corresponds to a ratio that ranges between 0.4 and 4, said ratio being calculated between the metal base equivalents and the sum of the acid equivalents of the calixarene of formula (I), also including the acid equivalents of any organic acid compound, or of any mixture of organic acid compounds optionally present.

20. The process according to claim 16, wherein in a first step a calixarene of formula (I) is mixed with a lubricant base oil or mixture of lubricant base oils, and optionally with an organic acid compound or a mixture of organic acid compounds, and then a metal base and the reaction solvent or the mixture of reaction solvents are added.

21. The process according to claim 16 wherein the salification reaction is conducted at a temperature between 30° C. and 200° C., at a pressure between 0.01 bar and 1.5 bar and removing the water of reaction by distillation.

22. A process for the preparation of the detergent composition comprising an overbased metal compound of calixarene of the general formula (I), according to claim 10, which comprises reacting with an excess of the metal base an acid compound, or the metal compound partially salified, neutral, basic or overbased, and then conducting carbonation of unreacted metal base; said process being conducted in the presence of a reaction solvent, or a mixture of reaction solvents, and the following reactants:

a calixarene of formula (I), or a metal compound of the calixarene of formula (I) partially salified, neutral, basic or overbased, or mixtures thereof;
a metal base;
carbon dioxide.

23. The process according to claim 22, wherein also an organic acid compound, or a mixture thereof, is added in the reaction with the metal base.

24. The process according to claim 22, wherein a lubricant base oil or a mixture of lubricant base oils is added during the procedure.

25. The process according to claim 23 wherein the amount of metal base used corresponds to a ratio between 1.1 and 15, said ratio being calculated between the equivalents of the metal base and the sum of the equivalents of the calixarene of formula (I) and the metal compound partially salified, neutral, basic or overbased including the equivalents of the organic acid compound, or the mixture thereof.

26. The process according to claim 22 wherein the amount of said carbon dioxide used corresponds to a ratio between the equivalents of said carbon dioxide and those of the metal base in excess with respect to the equivalents of the compounds to be neutralized, comprised between 0.6 and 4.

27. The process according to claim 22, which comprises the following steps: mixing said calixarene of formula (I), or said metal compound of said calixarene of formula (I) partially salified, neutral, basic or overbased or a mixture thereof, and optionally an organic acid compound or a mixture of organic acid compounds, with a lubricant base oil, or a mixture of lubricant base oils, thus forming a mixture of reactants; optionally removing the solvent possibly present in the mixture of reactants by distillation; subsequently adding to said mixture of reactants the metal base in excess and a part of the reaction solvent, or a part of a mixture of reaction solvents, and removing by distillation the water of reaction formed, forming a second mixture; optionally adding an organic acid compound, or a mixture of organic acid compounds and removing by distillation the water of reaction formed, forming a third mixture; subsequently adding to said second mixture or said third mixture a further part of the reaction solvent, or a further part of a mixture of reaction solvents, and removing by distillation the water of reaction formed, forming a fourth mixture; adding to said fourth mixture a further part of the reaction solvent, or a further part of a mixture of reaction solvents, forming a fifth mixture; then proceeding with the carbonation reaction between said fifth mixture and said carbon dioxide.

28. The process according to claim 22 wherein the step of reaction with an excess of the metal base is conducted at a temperature comprised between 30° C. and 200° C. and at a pressure between 0.01 bar and 1.5 bar and wherein the step of carbonation reaction with said carbon dioxide is conducted at a temperature between 15° C. and 180° C. and at a pressure of between 1 bar and 5 bar by feeding said carbon dioxide as a gas for a time comprised between 10 minutes and 6 hours.

29. The process according to claim 22 wherein, once the carbonation is completed, it proceeds to the maturation of the reaction mixture at a temperature comprised between 40° C. and 160° C. for a time between 10 minutes and 3 hours.

30. The process according to claim 16 wherein the calixarene of formula (I) is mixed with a linear oligomeric compound of the following formula (IV) and a monomer of the following formula (V):

containing carbon and hydrogen, a group containing in addition to carbon and hydrogen also heteroatoms, provided that sulfur is not present;

$R_{14}$, $R_{15}$, $R_{20}$ and $R_{21}$ are selected from hydrogen or an alkyl with a number of carbon atoms between 1 and 6;

$R_{11}$ and $R_{26}$ are independently selected from hydrogen, the hydroxymethylene group —$CH_2OH$, methyl and the hydroxycarbonyl group —COOH;

P is a number in the range between 0 and 20.

31. The process according to claim 16 wherein the metal of the metal base is selected from an alkaline earth metal, or an alkali metal.

32. The process according to claim 16 wherein the metal base is selected from an oxide or a hydroxide of calcium or magnesium.

33. The process according to claim 16 wherein an organic acid compound, or a mixture thereof, is present during the reaction of salification, wherein the organic acid compound is selected from:

a carboxylic, dicarboxylic and polycarboxylic acid containing a number of carbon atoms between 6 and 100;

a compound of formula (VII):

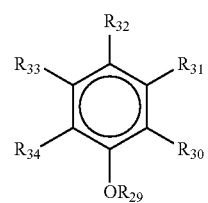

(VII)

in which $R_{29}$, $R_{30}$, $R_{31}$, $R_{32}$, $R_{33}$, and $R_{34}$ are independently selected from hydrogen, a group containing carbon and hydrogen, a group containing in addition to carbon and hydrogen also a heteroatom, provided that sulfur is not present;

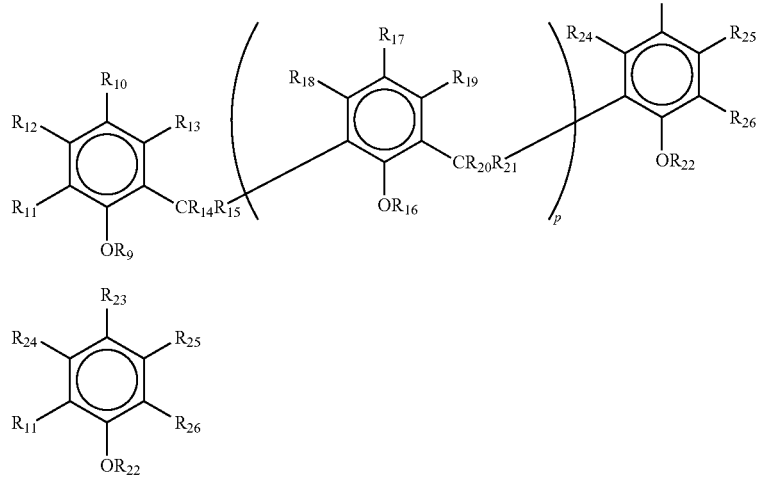

in which:

$R_9$, $R_{10}$, $R_{12}$, $R_{13}$, $R_{16}$, $R_{17}$, $R_{18}$, $R_{19}$, $R_{22}$, $R_{23}$, $R_{24}$ and $R_{25}$ are independently selected from hydrogen, a group a phenol substituted with a linear or branched alkyl group, in number comprised between 1 and 3, each containing a number of carbon atoms between 4 and 40;

a salicylic acid substituted with a linear or branched alkyl group, in number comprised between 1 and 3, each containing a number of carbon atoms comprised between 2 and 40;

a calixarene of general formula (Z) having substituents of hydroxyl type:

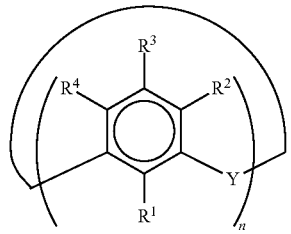

in which Y is a divalent bridge group; $R_3$ is a group containing carbon and hydrogen, or a group containing in addition to carbon and hydrogen also a heteroatom; n is an integer between 3 and 9, and alternatively:

$R_1$ is hydroxyl and $R_2$ and $R_4$ are independently hydrogen, or a group containing carbon and hydrogen, or a group containing in addition to carbon and hydrogen also a heteroatom; or $R_2$ and $R_4$ are hydroxyl groups and $R_1$ is independently hydrogen, or a group containing carbon and hydrogen, or a group containing in addition to carbon and hydrogen also a heteroatom.

34. The process according to claim 16 wherein the reaction solvent or the mixture of reaction solvents is selected from an alcohol with an acyclic or cyclic alkyl chain, or alkaryl, containing a number of carbon atoms between 1 and 16; a poly-hydroxylated hydrocarbon having a number of carbon atoms comprised between 2 and 4; a dialkylene glycol or a trialkylene glycol in which the alkylene group contains from 2 to 4 carbon atoms; a monoalkylene glycol alkyl ether, or a polyalkylene glycol alkyl ether in which the alkylene group contains from 2 to 4 carbon atoms and the alkyl group contains from 1 to 6 carbon atoms; water; a ketone with alkyl, or alkaryl, or an aromatic group, each containing a number of carbon atoms between 1 and 10; an ester of an aliphatic or aromatic carboxylic acid with a number of carbon atoms between 1 and 10; an aliphatic or aromatic ether containing a number of carbon atoms comprised between 2 and 20; or an aromatic or aliphatic hydrocarbon containing a number of carbon atoms between 5 and 16.

* * * * *